United States Patent
Clark et al.

(10) Patent No.: US 10,093,882 B2
(45) Date of Patent: Oct. 9, 2018

(54) PROCESSES FOR RECOVERING OIL FROM FERMENTATION PRODUCT PROCESSES AND PROCESSES FOR PRODUCING FERMENTATION PRODUCTS

(71) Applicant: Novozymes A/S, Bagsvaerd (DK)

(72) Inventors: Suzanne Clark, Youngsville, NC (US); John Matthews, Louisburg, NC (US); Joseph Jump, Raleigh, NC (US); Nathaniel Kreel, Louisburg, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 14/901,508

(22) PCT Filed: Jun. 20, 2014

(86) PCT No.: PCT/US2014/043444
§ 371 (c)(1),
(2) Date: Dec. 28, 2015

(87) PCT Pub. No.: WO2014/209800
PCT Pub. Date: Dec. 31, 2014

(65) Prior Publication Data
US 2016/0152923 A1    Jun. 2, 2016

Related U.S. Application Data

(60) Provisional application No. 61/838,650, filed on Jun. 24, 2013, provisional application No. 61/863,727, filed on Aug. 8, 2013, provisional application No. 61/943,794, filed on Feb. 24, 2014, provisional application No. 61/991,866, filed on May 12, 2014.

(51) Int. Cl.
| | |
|---|---|
| *C11B 13/00* | (2006.01) |
| *C11B 3/00* | (2006.01) |
| *C12N 9/28* | (2006.01) |
| *C12N 9/34* | (2006.01) |
| *C12P 7/10* | (2006.01) |
| *C12N 9/50* | (2006.01) |
| *C12P 7/64* | (2006.01) |
| *C12N 9/52* | (2006.01) |
| *C12N 9/58* | (2006.01) |
| *B01D 3/00* | (2006.01) |

(52) U.S. Cl.
CPC ............. *C11B 13/00* (2013.01); *C11B 3/003* (2013.01); *C12N 9/2417* (2013.01); *C12N 9/2428* (2013.01); *C12N 9/50* (2013.01); *C12N 9/52* (2013.01); *C12N 9/58* (2013.01); *C12P 7/10* (2013.01); *C12P 7/64* (2013.01); *B01D 3/002* (2013.01); *C12Y 302/01001* (2013.01); *C12Y 302/01003* (2013.01); *C12Y 304/00* (2013.01); *Y02E 50/13* (2013.01); *Y02E 50/16* (2013.01)

(58) Field of Classification Search
None
See application file for complete search history.

(56) References Cited

U.S. PATENT DOCUMENTS

| | | | |
|---|---|---|---|
| 6,358,726 | B1 | 3/2002 | Takahura |
| 8,008,517 | B2 | 8/2011 | Cantrell |
| 2009/0227004 | A1 | 9/2009 | Dale |

FOREIGN PATENT DOCUMENTS

| | | |
|---|---|---|
| WO | 02/074895 A1 | 9/2002 |
| WO | 04/080923 A1 | 9/2004 |
| WO | 2007/056321 A1 | 5/2007 |
| WO | 2009/052101 A1 | 4/2009 |
| WO | 2011/126897 A2 | 10/2011 |
| WO | 2012/088303 A2 | 6/2012 |
| WO | 2012084225 A1 | 6/2012 |
| WO | 2013/082486 A2 | 6/2013 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession Q8U0C9. Jun. 1, 2002.*
Gray et al, 1986, Uniprot access No. P00799.
Lao et al, 1998, Uniprot access No. O86984.
Silva et al, 1998, Uniprot access No. O31193.
Singh et al, 2017, Curr Protein and Peptide Science 18, 1-11.
WO 2003-048353—Access No. ABR62336.

* cited by examiner

*Primary Examiner* — Christian L Fronda
(74) *Attorney, Agent, or Firm* — David Fazzolare

(57) ABSTRACT

The present invention relates to processes for recovering/extracting oil from fermentation product production processes based on starch-containing material, wherein an alpha-amylase, a high dosage of protease, and optionally a glucoamylase, are present and/or added in liquefaction. The invention also relates to processes for producing fermentation products and to enzyme compositions suitable for use in processes of the invention.

20 Claims, 11 Drawing Sheets
Specification includes a Sequence Listing.

US 10,093,882 B2

PROCESSES FOR RECOVERING OIL FROM FERMENTATION PRODUCT PROCESSES AND PROCESSES FOR PRODUCING FERMENTATION PRODUCTS

CROSS-REFERENCE TO RELATED APPLICATIONS

This application is a 35 U.S.C. 371 national application of PCT/US2014/043444 filed Jun. 20, 2014, which claims priority or the benefit under 35 U.S.C. 119 of U.S. provisional application Nos. 61/838,650, 61/863,727, 61/943,794 and 61/991,866 filed Jun. 24, 2013, Aug. 8, 2013, Feb. 24, 2014 and May 12, 2014, respectively, the contents of which are fully incorporated herein by reference.

REFERENCE TO A SEQUENCE LISTING

This application contains a Sequence Listing in computer readable form. The computer readable form is incorporated herein by reference.

FIELD OF THE INVENTION

The present invention relates to processes of recovering oil from a fermentation product production process and well as processes for producing fermentation products from starch-containing material. The invention also relates to compositions suitable for use in a process of the invention.

BACKGROUND OF THE INVENTION

Fermentation products, such as ethanol, are typically produced by first grinding starch-containing material in a dry-grind or wet-milling process, then degrading the material into fermentable sugars using enzymes and finally converting the sugars directly or indirectly into the desired fermentation product using a fermenting organism. Liquid fermentation products are recovered from the fermented mash (often referred to as "beer mash"), e.g., by distillation, which separate the desired fermentation product from other liquids and/or solids. The remaining faction is referred to as "whole stillage". The whole stillage is dewatered and separated into a solid and a liquid phase, e.g., by centrifugation. The solid phase is referred to as "wet cake" (or "wet grains") and the liquid phase (supernatant) is referred to as "thin stillage". Wet cake and thin stillage contain about 35 and 7% solids, respectively. Dewatered wet cake is dried to provide "Distillers Dried Grains" (DDG) used as nutrient in animal feed. Thin stillage is typically evaporated to provide condensate and syrup or may alternatively be recycled directly to the slurry tank as "backset". Condensate may either be forwarded to a methanator before being discharged or may be recycled to the slurry tank. The syrup may be blended into DDG or added to the wet cake before drying to produce DDGS (Distillers Dried Grain with Solubles).

WO 2012/088303 (Novozymes) discloses processes for producing fermentation products by liquefying starch-containing material at a pH in the range from 4.5-5.0 at a temperature in the range from 80-90° C. using a combination of alpha-amylase having a T½ (min) at pH 4.5, 85° C., 0.12 mM CaCl2) of at least 10 and a protease having a thermostability value of more than 20% determined as Relative Activity at 80° C./70° C.; followed by saccharification and fermentation.

WO 2013/082486 (Novozymes) discloses processes for producing fermentation products by liquefying starch-containing material at a pH in the range between from above 5.0-7.0 at a temperature above the initial gelatinization temperature using an alpha-amylase; a protease having a thermostability value of more than 20% determined as Relative Activity at 80° C./70° C.; and optionally a carbohydrate-source generating enzyme followed by saccharification and fermentation.

An increasing number of ethanol plants extract oil from the thin stillage and/or syrup as a by-product for use in biodiesel production or other biorenewable products. Much of the work in oil recovery/extraction from fermentation product production processes has focused on improving the extractability of the oil from the thin stillage. Effective removal of oil is often accomplished by hexane extraction. However, the utilization of hexane extraction has not seen widespread application due to the high capital investment required. Therefore, other processes that improve oil extraction from fermentation product production processes have been explored.

WO 2011/126897 (Novozymes) discloses processes of recovering oil by converting starch-containing materials into dextrins with alpha-amylase; saccharifying with a carbohydrate source generating enzyme to form sugars; fermenting the sugars using fermenting organism; wherein the fermentation medium comprises a hemicellulase; distilling the fermentation prodct to form whole stillage; separating the whole stillage into thin stillage and wet cake; and recovering oil from the thin stillage. The fermentation medium may further comprise a protease.

It is an object of the present invention to provide improved processes for increasing the amount of recoverable oil from fermentation product production processes and to provide processes for producing fermentation products, such as ethanol, from starch-containing material that can provide a higher fermentation product yield, or other advantages, compared to a conventional process.

SUMMARY OF THE INVENTION

The present invention relates to processes of recovering/extracting oil from fermentation product production processes. The invention also related to producing fermentation products, such as ethanol, from starch-containing material in a process including liquefying starch-containing material, saccharifying and fermenting the liquefied material. The invention also relates to compositions suitable for use in a process of the invention.

In the first aspect the invention relates to processes of recovering/extracting oil from a fermentation product production process comprising the steps of:
  a) liquefying starch-containing material at a temperature above the initial gelatinization temperature using:
    an alpha-amylase;
    more than 0.5 micro gram *Pyrococcus furiosus* protease per gram dry solids (DS);
  b) saccharifying using a glucoamylase;
  c) fermenting using a fermenting organism.
  d) recovering the fermentation product to form whole stillage;
  e) separating the whole stillage into thin stillage and wet cake;
  f) optionally concentrating the thin stillage into syrup;
wherein oil is recovered from the:
    liquefied starch-containing material during and/or after step a); and/or
    downstream from fermentation step c).

In an embodiment between 0.5-100 micro gram *Pyrococcus furiosus* protease per gram DS (dry solids) DS is present and/or added in liquefaction step a). In an embodiment between 0.5-10 micro gram *Pyrococcus furiosus* protease per gram DS (dry solids) is present and/or added in liquefaction step a). In an embodiment between 1-50 micro gram *Pyrococcus furiosus* protease per gram DS is present and/or added in liquefaction step a). In an embodiment between 1-10 micro gram *Pyrococcus furiosus* protease per gram DS is present and/or added in liquefaction step a). In an embodiment between 1.5-5 micro gram *Pyrococcus furiosus* protease per gram DS is present and/or added in liquefaction step a). In an embodiment around or more than 1.5 micro gram *Pyrococcus furiosus* protease per gram DS is present and/or added in liquefaction step a). In an embodiment around or more than 2 micro gram *Pyrococcus furiosus* protease per gram DS is present and/or added in liquefaction step a). In an embodiment around or more than 3 micro gram *Pyrococcus furiosus* protease per gram DS is present and/or added in liquefaction step a).

In a preferred embodiment the *Pyrococcus furiosus* protease is the mature sequence shown in SEQ ID NO: 13 herein or one having at least 90% or 95% identity thereof.

Examples of alpha-amylase can be found below in the "Alpha-Amylases Present and/or Added In Liquefaction"-section below.

Preferred alpha-amylases are *Bacillus* sp. alpha-amylases or variants thereof, especially derived from *Bacillus stearothermophilus* or *Bacillus licheniformis*.

In a preferred embodiment the alpha-amylase is a *Bacillus stearothermophilus* alpha-amylase variant comprising a double deletion in positions I181*+G182* (using SEQ ID NO: 1 for numbering).

Preferred alpha-amylases include *Bacillus stearothermophilus* alpha-amylase variants, such as one shown in SEQ ID NO: 1 herein with the following mutations:
 I181*+G182*+N193F+E129V+K177L+R179E;
 I181*+G182*+N193F+V59A+Q89R+E129V+K177L+R179E+H208Y+K220P+N224L+Q254S
 I181*+G182*+N193F+V59A Q89R+E129V+K177L+R179E+Q254S+M284V; and
 I181*+G182*+N193F+E129V+K177L+R179E+K220P+N224L+S242Q+Q254S (using SEQ ID NO: 1 for numbering).

In an embodiment a glucoamylase is present and/or added in liquefaction. Examples of suitable glucoamylase can be found in the "Glucoamylase Present And/Or Added In Liquefaction" section below.

In an embodiment the glucoamylase has a thermostability of at least 80° C., preferably at least 82° C., such as at least 84° C., such as at least 86° C., such as at least 88° C. at pH 4.0 determined as Differential Scanning calorimitry (DSC) as described in Example 3 below.

In an embodiment the glucoamylase has a thermostability of at least 80° C., preferably at least 82° C., such as at least 84° C., such as at least 86° C., such as at least 88° C., such as at least 90° C. at pH 4.8 determined as Differential Scanning calorimitry (DSC) as described in Example 3 below.

Examples of specifically contemplated glucoamylases can be found in Example 3 (Table 6) below.

Preferred glucoamylases include *Penicillium oxalicum* glucoamylases, such as one shown in SEQ ID NO: 14 herein having a K79V substitution and preferably further one of the following:

P11F+T65A+Q327F;
 P2N+P4S+P11F+T65A+Q327F (using SEQ ID NO: 14 for numbering).

In a preferred embodiment liquefaction is carried out at a temperature between 80-90° C., such as around 85° C. In a preferred embodiment liquefaction is carried out at a pH in the range pH above 5.0 to 6.0.

A glucoamylase is present and/or added in saccharification and/or fermentation. Examples of suitable glucoamylases can be found in the "Glucoamylase Present And/Or Added In Saccharification And/Or Fermentation" section below.

In a second aspect the invention relates to processes for producing fermentation products from starch-containing material comprising the steps of:
 a) liquefying the starch-containing material at a temperature above the initial gelatinization temperature using:
  an alpha-amylase;
  more than 2 micro gram *Pyrococcus furiosus* protease per gram dry solids (DS);
 b) saccharifying using a glucoamylase;
 c) fermenting using a fermenting organism.

In a preferred embodiment between 2-100 micro gram *Pyrococcus furiosus* protease per gram DS is present and/or added in liquefaction step a). In a preferred embodiment between 2-10 micro gram *Pyrococcus furiosus* protease per gram DS is present and/or added in liquefaction step a). In a preferred embodiment between 2.5-50 micro gram *Pyrococcus furiosus* protease per gram DS is present and/or added in liquefaction step a). In a preferred embodiment between 2.5-10 micro gram per gram DS is present and/or added in liquefaction step a). In a preferred embodiment between 2.5-5 micro gram *Pyrococcus furiosus* protease per gram DS is present and/or added in liquefaction step a). In a preferred embodiment around or more than 3 micro gram *Pyrococcus furiosus* protease per gram DS is present and/or added in liquefaction step a).

In a preferred embodiment the *Pyrococcus furiosus* protease is the mature one shown in SEQ ID NO: 13 herein or one having at least 90% or at least 95% identity thereof.

Examples of alpha-amylase can be found below in the "Alpha-Amylases Present and/or Added In Liquefaction"-section below.

Preferred alpha-amylases are *Bacillus* sp. alpha-amylases or variants thereof, especially derived from *Bacillus stearothermophilus* or *Bacillus licheniformis*.

In a preferred embodiment the alpha-amylase is a *Bacillus stearothermophilus* alpha-amylase variant comprising a double deletion in I181*+G182* (using SEQ ID NO: 1 for numbering).

Preferred alpha-amylases include *Bacillus stearothermophilus* alpha-amylase variants, such as one shown in SEQ ID NO: 1 herein with the following mutations:
 I181*+G182*+N193F+E129V+K177L+R179E;
 I181*+G182*+N193F+V59A+Q89R+E129V+K177L+R179E+H208Y+K220P+N224L+Q254S
 I181*+G182*+N193F+V59A Q89R+E129V+K177L+R179E+Q254S+M284V; and
 I181*+G182*+N193F+E129V+K177L+R179E+K220P+N224L+S242Q+Q254S (using SEQ ID NO: 1 for numbering).

In an embodiment glucoamylase is present and/or added in liquefaction. Examples of suitable glucoamylase can be found in the "Glucoamylase Present And/Or Added In Liquefaction" section below.

In an embodiment the glucoamylase has a thermostability of at least 80° C., preferably at least 82° C., such as at least 84° C., such as at least 86° C., such as at least 88° C. at pH 4.0 determined as Differential Scanning calorimitry (DSC) as described in Example 3 below.

In an embodiment the glucoamylase has a thermostability of at least 80° C., preferably at least 82° C., such as at least 84° C., such as at least 86° C., such as at least 88° C., such as at least 90° C. at pH 4.8 determined as Differential Scanning calorimitry (DSC) as described in Example 3 below.

Examples of specifically contemplated glucoamylases can be found in Example 3 (Table 6) below.

Preferred glucoamylases include *Penicillium oxalicum* glucoamylases, such as one shown in SEQ ID NO: 14 herein having a K79V substitution and preferably further one of the following:

P11F+T65A+Q327F;
P2N+P4S+P11F+T65A+Q327F (using SEQ ID NO: 14 for numbering).

A glucoamylase is present and/or added in saccharification and/or fermentation. Examples of suitable glucoamylases can be found in the "Glucoamylase Present And/Or Added In Saccharification And/Or Fermentation" section below.

In a third aspect the invention relates to an enzyme composition comprising:
(i) *Bacillus* sp. alpha-amylase, or a variant thereof;
(ii) *Pyrococcus furiosus* protease;
wherein the ratio between alpha-amylase and protease is in the range from 1:1 and 1:25 (micro gram alpha-amylase: micro gram protease).

Examples of alpha-amylase can be found below in the "Alpha-Amylases Present And/Or Added In Liquefaction" section below.

Preferred alpha-amylases are *Bacillus* sp. alpha-amylases or variants thereof, especially derived from *Bacillus stearothermophilus* or *Bacillus licheniformis*.

In a preferred embodiment the alpha-amylase is a *Bacillus stearothermophilus* alpha-amylase variant comprising a double deletion in I181*+G182* (using SEQ ID NO: 1 for numbering).

Preferred alpha-amylases include *Bacillus stearothermophilus* alpha-amylase variants, such as one show in SEQ ID NO: 1 herein with the following mutations:

I181*+G182*+N193F+E129V+K177L+R179E;
I181*+G182*+N193F+V59A+Q89R+E129V+K177L+R179E+H208Y+K220P+N224L+Q254S
I181*+G182*+N193F+V59A Q89R+E129V+K177L+R179E+Q254S+M284V; and
I181*+G182*+N193F+E129V+K177L+R179E+K220P+N224L+S242Q+Q254S (using SEQ ID NO: 1 for numbering).

In an embodiment a glucoamylase is present and/or added in liquefaction. Examples of suitable glucoamylase can be found in the "Glucoamylase Present And/Or Added In Liquefaction" section below.

In an embodiment the glucoamylase has a thermostability of at least 80° C., preferably at least 82° C., such as at least 84° C., such as at least 86° C., such as at least 88° C. at pH 4.0 determined as Differential Scanning calorimitry (DSC) as described in Example 3 below.

In an embodiment the glucoamylase has a thermostability of at least 80° C., preferably at least 82° C., such as at least 84° C., such as at least 86° C., such as at least 88° C., such as at least 90° C. at pH 4.8 determined as Differential Scanning calorimitry (DSC) as described in Example 3 below.

Examples of specifically contemplated glucoamylases can be found in Example 3 (Table 6) below.

Preferred glucoamylases include *Penicillium oxalicum* glucoamylases, such as one shown in SEQ ID NO: 14 herein having a K79V substitution and further one of the following:

P11F+T65A+Q327F;
P2N+P4S+P11F+T65A+Q327F (using SEQ ID NO: 14 for numbering).

In a preferred embodiment the ratio between alpha-amylase and protease is in the range between 1:1.2 and 1:10, such as around 1:1.4 (micro gram alpha-amylase:micro gram protease).

In another embodiment the enzyme composition of the invention comprises a glucoamylase and the ratio between alpha-amylase and glucoamylase in liquefaction is between 1:1 and 1:10, such as around 1:2 (micro gram alpha-amylase:micro gram glucoamylase).

DETAILED DESCRIPTION OF THE INVENTION

Figure 1:
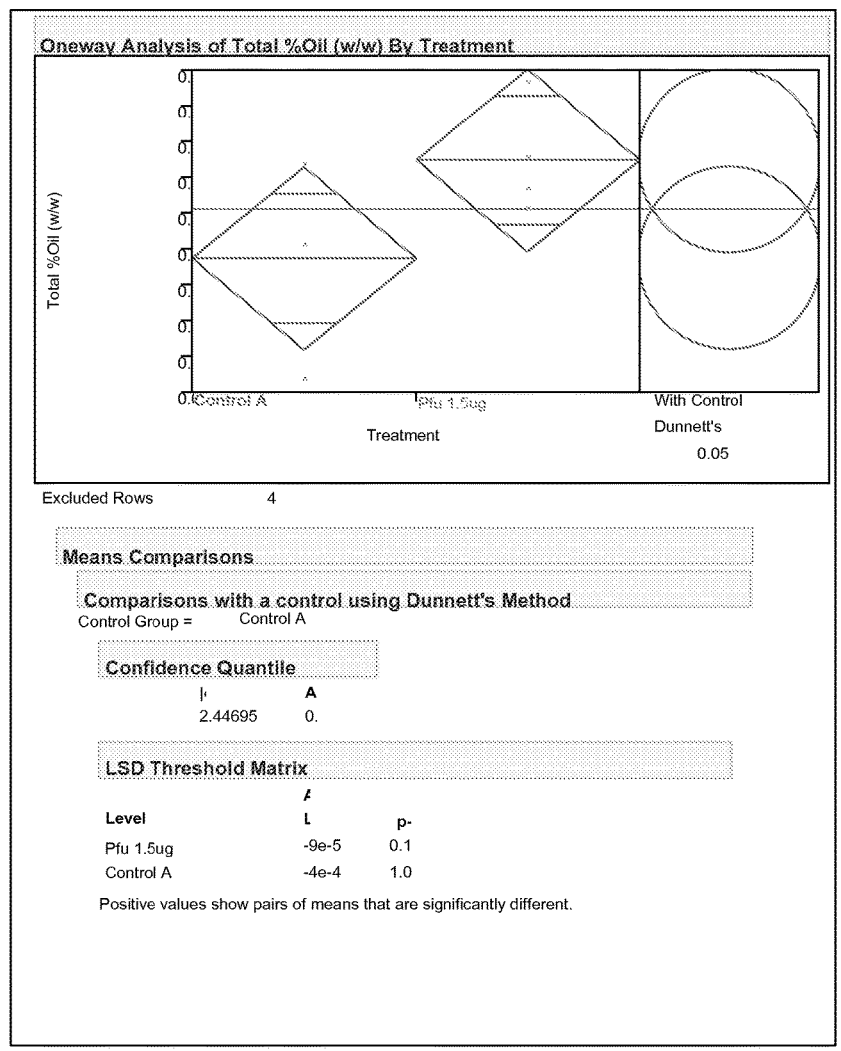
FIG. 1 shows an oil extraction comparison between Protease Pfu (1.5 μg/gDS) and Protease X (no statistical difference).

The present invention relates to processes of recovering oil from a fermentation product production process and well as processes for producing fermentation products from starch-containing material. The invention also relates to compositions suitable for use in a process of the invention.

The inventors have found that an increased amount of oil can be recovered in liquefaction or downstream from fermentation when combining an alpha-amylase, a high amount of *Pyrococcus furiosus* protease and optionally a glucoamylase compared to when adding an alpha-amylase in liquefaction and a protease during fermentation (SSF).

The inventors also found that an increased ethanol yield is obtained when combining an alpha-amylase, more than 2 micro gram *Pyrococcus furiosus* protease per gram dry solids (DS) and a glucoamylase compared to when using alpha-amylase, less than 2 micro gram *Pyrococcus furiosus* protease per gram dry solids (DS) and glucoamylase during liquefaction.

The inventors also found that the glycerol concentration is lower with Protease Pfu (5 μg/gDS) compared to adding protease in SSF.

It was also found that an ethanol process of the invention can be run efficiently with reduced or without adding a nitrogen source, such as urea, in SSF.

Processes of Recovering/Extracting Oil of the Invention

In the first aspect the invention relates to processes of recovering oil from a fermentation product production process comprising the steps of:
  a) liquefying starch-containing material at a temperature above the initial gelatinization temperature using:
    an alpha-amylase;
    more than 0.5 micro gram *Pyrococcus furiosus* protease per gram dry solids (DS);
  b) saccharifying using a glucoamylase;
  c) fermenting using a fermenting organism.
  d) recovering the fermentation product to form whole stillage;
  e) separating the whole stillage into thin stillage and wet cake;
  f) optionally concentrating the thin stillage into syrup;
wherein oil is recovered from the:
    liquefied starch-containing material after step a); and/or
    downstream from fermentation step c).

In an embodiment the oil is recovered/extracted during and/or after liquefying the starch-containing material. In an embodiment the oil is recovered from the whole stillage. In an embodiment the oil is recovered from the thin stillage. In an embodiment the oil is recovered from the syrup.

In an embodiment between 0.5-100 micro gram *Pyrococcus furiosus* protease per gram DS (dry solids) DS is present and/or added in liquefaction step a). In an embodiment between 0.5-10 micro gram *Pyrococcus furiosus* protease per gram DS (dry solids) DS is present and/or added in liquefaction step a). In an embodiment between 1-50 micro gram *Pyrococcus furiosus* protease per gram DS is present and/or added in liquefaction step a). In an embodiment between 1-10 micro gram *Pyrococcus furiosus* protease per gram DS is present and/or added in liquefaction step a). In an embodiment between 1.5-5 micro gram *Pyrococcus furiosus* protease per gram DS is present and/or added in liquefaction step a). In an embodiment around or more than 1 micro gram *Pyrococcus furiosus* protease per gram DS is present and/or added in liquefaction step a). In an embodiment around or more than 1.5 micro gram *Pyrococcus furiosus* protease per gram DS is present and/or added in liquefaction step a). In an embodiment around or more than 2 micro gram *Pyrococcus furiosus* protease per gram DS is present and/or added in liquefaction step a).

In an embodiment between 2-100 micro gram *Pyrococcus furiosus* protease per gram DS is added and/or present during liquefaction. In an embodiment between 2.5-50 micro gram *Pyrococcus furiosus* protease per gram DS is added and/or present during liquefaction. In an embodiment between 2.5-10 micro gram *Pyrococcus furiosus* protease per gram DS is added and/or present during liquefaction. In an embodiment between 2.5-5 micro gram *Pyrococcus furiosus* protease per gram DS is added and/or present during liquefaction. In an embodiment between 2.75-50 micro gram *Pyrococcus furiosus* protease per gram DS is added and/or present during liquefaction. In an embodiment between 2.75-10 micro gram *Pyrococcus furiosus* protease per gram DS is added and/or present during liquefaction. In an embodiment between 2.75-5 micro gram *Pyrococcus furiosus* protease per gram DS is added and/or present during liquefaction. In a preferred embodiment around or more than 3 micro gram *Pyrococcus furiosus* protease per gram DS are present and/or added in liquefaction step a).

In a preferred embodiment the *Pyrococcus furiosus* protease is the mature sequence shown in SEQ ID NO: 13 herein. In an embodiment the *Pyrococcus furiosus* protease is one having at least 80%, such as at least 85%, such as at least 90%, such as at least 95%, such as at least 96%, such as at least 97%, such as at least 98%, such as at least 99% identity to SEQ ID NO: 13 herein.

In an embodiment no nitrogen-compound, such as urea, is present and/or added in steps a)-c), such as during saccharification step b), fermentation step c), or simultaneous saccharification and fermentation (SSF).

In an embodiment 10-1,000 ppm, such as 50-800 ppm, such as 100-600 ppm, such as 200-500 ppm nitrogen-compound, preferably urea, is present and/or added in steps a)-c), such as in saccharification step b) or fermentation step c) or in simultaneous saccharification and fermentation (SSF).

Process of Producing a Fermentation Product of the Invention

In the second aspect the invention relates to processes for producing fermentation products from starch-containing material comprising the steps of:
  a) liquefying the starch-containing material at a temperature above the initial gelatinization temperature using:
    an alpha-amylase;
    more than 2 micro gram *Pyrococcus furiosus* protease per gram dry solids (DS);
  b) saccharifying using a glucoamylase;
  c) fermenting using a fermenting organism.

In an embodiment the fermentation product is recovered after fermentation. In a preferred embodiment the fermentation product is recovered after fermentation, such as by distillation. In an embodiment the fermentation product is an alcohol, preferably ethanol, especially fuel ethanol, potable ethanol and/or industrial ethanol.

In an embodiment from 2-100 micro gram *Pyrococcus furiosus* protease per gram DS is added and/or present during liquefaction. In an embodiment 2.5-50 micro gram *Pyrococcus furiosus* protease per gram DS is added and/or present during liquefaction. In an embodiment 2.5-10 micro gram *Pyrococcus furiosus* protease per gram DS is added and/or present during liquefaction. In an embodiment 2.5-5 micro gram *Pyrococcus furiosus* protease per gram DS is added and/or present during liquefaction. In an embodiment 2.75-50 micro gram *Pyrococcus furiosus* protease per gram DS is added and/or present during liquefaction. In an embodiment 2.75-10 micro gram *Pyrococcus furiosus* protease per gram DS is added and/or present during liquefaction. In an embodiment 2.75-5 micro gram *Pyrococcus furiosus* protease per gram DS is added and/or present during liquefaction. In a preferred embodiment around 3 micro gram *Pyrococcus furiosus* protease per gram DS is present and/or added in liquefaction step a).

In a preferred embodiment the *Pyrococcus furiosus* protease is the one shown in SEQ ID NO: 13 herein. In an embodiment the *Pyrococcus furiosus* protease is one having at least 80%, such as at least 85%, such as at least 90%, such as at least 95%, such as at least 96%, such as at least 97%, such as at least 98%, such as at least 99% identity to SEQ ID NO: 13 herein.

In a preferred embodiment no nitrogen-compound is present and/or added in steps a)-c), such as during saccharification step b) or fermentation step c) or simultaneous saccharification and fermentation (SSF).

In an embodiment 10-1,000 ppm, such as 50-800 ppm, such as 100-600 ppm, such as 200-500 ppm nitrogen-compound, preferably urea, is present and/or added in steps a)-c), such as during saccharification step b) or fermentation step c) or simultaneous saccharification and fermentation (SSF).

Alpha-Amylases Present and/or Added in Liquefaction

The alpha-amylase added during liquefaction step a) in a process of the invention (i.e., oil recovery process and fermentation product production process) may be any alpha-amylase.

Preferred are bacterial alpha-amylases, which typically are stable at a temperature used in liquefaction.

In an embodiment the alpha-amylase is from a strain of the genus Bacillus.

In a preferred embodiment the alpha-amylase is from a strain of *Bacillus stearothermophilus*, such as the sequence shown in SEQ ID NO: 1. In an embodiment the alpha-amylase is the *Bacillus stearothermophilus* alpha-amylase shown in SEQ ID NO: 1 herein, such as one having at least 80%, such as at least 85%, such as at least 90%, such as at least 95%, such as at least 96%, such as at least 97%, such as at least 98%, such as at least 99% identity to SEQ ID NO: 1 herein.

In an embodiment the *Bacillus stearothermophilus* alpha-amylase or variant thereof is truncated, preferably at the C-terminal, preferably truncated to have around 491 amino acids, such as from 480-495 amino acids.

In an embodiment the *Bacillus stearothermophilus* alpha-amylase has a double deletion at positions I181+G182, and optionally a N193F substitution (using SEQ ID NO: 1 for numbering).

In another embodiment the *Bacillus stearothermophilus* alpha-amylase has a double deletion at positions R179+G180 and optionally a N193F substitution (using SEQ ID NO: 1 for numbering).

In an embodiment the *Bacillus stearothermophilus* alpha-amylase has a substitution at position S242, preferably S242Q substitution.

In an embodiment the *Bacillus stearothermophilus* alpha-amylase has a substitution at position E188, preferably E188P substitution.

In an embodiment the alpha-amylase has a T½ (min) at pH 4.5, 85° C., 0.12 mM $CaCl_2$) of at least 10.

In embodiment the alpha-amylase has a T½ (min) at pH 4.5, 85° C., 0.12 mM $CaCl_2$) of at least 15.

In an embodiment the alpha-amylase has a T½ (min) at pH 4.5, 85° C., 0.12 mM $CaCl_2$) of at least 20.

In an embodiment the alpha-amylase has a T½ (min) at pH 4.5, 85° C., 0.12 mM $CaCl_2$) of at least 25.

In an embodiment the alpha-amylase has a T½ (min) at pH 4.5, 85° C., 0.12 mM $CaCl_2$) of at least 30.

In an embodiment the alpha-amylase has a T½ (min) at pH 4.5, 85° C., 0.12 mM $CaCl_2$) of at least 40.

In an embodiment the alpha-amylase has a T½ (min) at pH 4.5, 85° C., 0.12 mM $CaCl_2$) of at least 50.

In an embodiment the alpha-amylase has a T½ (min) at pH 4.5, 85° C., 0.12 mM $CaCl_2$) of at least 60. In embodiment the alpha-amylase has a T½ (min) at pH 4.5, 85° C., 0.12 mM $CaCl_2$) between 10-70.

In an embodiment the alpha-amylase has a T½ (min) at pH 4.5, 85° C., 0.12 mM $CaCl_2$) between 15-70.

In an embodiment the alpha-amylase has a T½ (min) at pH 4.5, 85° C., 0.12 mM $CaCl_2$) between 20-70.

In an embodiment the alpha-amylase has a T½ (min) at pH 4.5, 85° C., 0.12 mM $CaCl_2$) between 25-70.

In an embodiment the alpha-amylase has a T½ (min) at pH 4.5, 85° C., 0.12 mM $CaCl_2$) between 30-70.

In an embodiment the alpha-amylase has a T½ (min) at pH 4.5, 85° C., 0.12 mM $CaCl_2$) between 40-70.

In an embodiment the alpha-amylase has a T½ (min) at pH 4.5, 85° C., 0.12 mM $CaCl_2$) between 50-70.

In an embodiment the alpha-amylase has a T½ (min) at pH 4.5, 85° C., 0.12 mM $CaCl_2$) between 60-70.

In an embodiment the alpha-amylase is selected from the group of *Bacillus stearothermophilus* alpha-amylase variants with the following mutations in addition to I181*+G182*, and optionally N193F:

V59A + Q89R + G112D + E129V + K177L + R179E + K220P + N224L + Q254S;
V59A + Q89R + E129V + K177L + R179E + H208Y + K220P + N224L + Q254S;
V59A + Q89R + E129V + K177L + R179E + K220P + N224L + Q254S + D269E + D281N;
V59A + Q89R + E129V + K177L + R179E + K220P + N224L + Q254S + I270L;
V59A + Q89R + E129V + K177L + R179E + K220P + N224L + Q254S + H274K;
V59A + Q89R + E129V + K177L + R179E + K220P + N224L + Q254S + Y276F;
V59A + E129V + R157Y + K177L + R179E + K220P + N224L + S242Q + Q254S;
V59A + E129V + K177L + R179E + H208Y + K220P + N224L + S242Q + Q254S;
59A + E129V + K177L + R179E + K220P + N224L + S242Q + Q254S;
V59A + E129V + K177L + R179E + K220P + N224L + S242Q + Q254S + H274K;
V59A + E129V + K177L + R179E + K220P + N224L + S242Q + Q254S + Y276F;
V59A + E129V + K177L + R179E + K220P + N224L + S242Q + Q254S + D281N;
V59A + E129V + K177L + R179E + K220P + N224L + S242Q + Q254S + M284T;
V59A + E129V + K177L + R179E + K220P + N224L + S242Q + Q254S + G416V;
V59A + E129V + K177L + R179E + K220P + N224L + Q254S;
V59A + E129V + K177L + R179E + K220P + N224L + Q254S + M284T;
A91L + M96I + E129V + K177L + R179E + K220P + N224L + S242Q + Q254S;
E129V + K177L + R179E;
E129V + K177L + R179E + K220P + N224L + S242Q + Q254S;
E129V + K177L + R179E + K220P + N224L + S242Q + Q254S + Y276F + L427M;
E129V + K177L + R179E + K220P + N224L + S242Q + Q254S + M284T;
E129V + K177L + R179E + K220P + N224L + S242Q + Q254S + N376* + I377*;
E129V + K177L + R179E + K220P + N224L + Q254S;
E129V + K177L + R179E + K220P + N224L + Q254S + M284T;
E129V + K177L + R179E + S242Q;
E129V + K177L + R179V + K220P + N224L + S242Q + Q254S;

K220P + N224L + S242Q + Q254S;
M284V;
V59A Q89R + E129V + K177L + R179E + Q254S + M284V.

In a preferred embodiment the alpha-amylase is selected from the group of *Bacillus stearothermophilus* alpha-amylase variants:

I181*+G182*+N193F+E129V+K177L+R179E;

I181*+G182*+N193F+V59A+Q89R+E129V+K177L+ R179E+H208Y+K220P+N224L+Q254S

I181*+G182*+N193F+V59A   Q89R+E129V+K177L+ R179E+Q254S+M284V; and

I181*+G182*+N193F+E129V+K177L+R179E+K220P+ N224L+S242Q+Q254S (using SEQ ID NO: 1 for numbering).

According to the invention the alpha-amylase variant has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 1 herein.

In another embodiment the alpha-amylase is a *Bacillus licheniformis* alpha-amylase, or a variant thereof. In an embodiment the *Bacillus licheniformis* alpha-amylase is the one shown in SEQ ID NO: 21 herein. According to the invention the alpha-amylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% identity to the mature part of the polypeptide of SEQ ID NO: 21 herein.

The alpha-amylase may according to the invention be present and/or added in a concentration of 0.1-100 micro gram per gram DS, such as 0.5-50 micro gram per gram DS, such as 1-25 micro gram per gram DS, such as 1-10 micro gram per gram DS, such as 2-5 micro gram per gram DS.

In an embodiment from 1-10 micro gram *Pyrococcus furiosus* protease and 1-10 micro gram *Bacillus stearothermophilus* alpha-amylase are present and/or added in liquefaction.

Glucoamylase Present and/or Added in Liquefaction

In an embodiment a glucoamylase is present and/or added in liquefaction step a) in a process of the invention (i.e., oil recovery process and fermentation product production process).

In a preferred embodiment the glucoamylase present and/or added in liquefaction has a heat stability at 85° C., pH 5.3, of at least 20%, such as at least 30%, preferably at least 35% determined as disclosed in Example 2 herein or Example 8 in WO 2011/127802

In an embodiment the glucoamylase has a relative activity pH optimum at pH 5.0 of at least 90%, preferably at least 95%, preferably at least 97% determined as disclosed in Example 2 herein or Example 8 in WO 2011/127802.

In an embodiment the glucoamylase has a pH stability at pH 5.0 of at least at least 80%, at least 85%, at least 90% determined as disclosed in Example 2 herein or Example 8 in WO 2011/127802.

In a preferred embodiment the glucoamylase present and/or added in liquefaction step a) is derived from a strain of the genus *Penicillium*, especially a strain of *Penicillium oxalicum* disclosed as SEQ ID NO: 2 in WO 2011/127802 or SEQ ID NOs: 9 or 14 herein.

In an embodiment the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 9 or 14 herein.

In an embodiment the glucoamylase has a thermostability of at least 80° C., preferably at least 82° C., such as at least 84° C., such as at least 86° C., such as at least 88° C. at pH 4.0 determined as Differential Scanning calorimitry (DSC) as described in Example 3 below.

In an embodiment the glucoamylase has a thermostability of at least 80° C., preferably at least 82° C., such as at least 84° C., such as at least 86° C., such as at least 88° C., such as at least 90° C. at pH 4.8 determined as Differential Scanning calorimitry (DSC) as described in Example 3 below.

Examples of specifically contemplated glucoamylases can be found in Example 3 (Table 6) below.

In a preferred embodiment the glucoamylase is a variant of the *Penicillium oxalicum* glucoamylase shown in SEQ ID NO: 2 in WO 2011/127802 or SEQ ID NO: 14 herein having a K79V substitution (using the mature sequence shown in SEQ ID NO: 14 for numbering), such as a variant disclosed in WO 2013/053801 (hereby incorporated by reference).

In an embodiment the *Penicillium oxalicum* glucoamylase has a K79V substitution (using SEQ ID NO: 14 for numbering) and preferably further one of the following substitutions:

T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or

T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+I172V+Q327F+E501V+Y504T; or
P2N+P4S+P11F+T65A+Q327F+S377T+E501V+Y504T; or
P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or
P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or
P2N+P4S+P11F+T65A+Q327F+E501V+Y504T+T568N; or
P2N+P4S+P11F+T65A+Q327F+E501V+Y504T+K524T+G526A; or
P2N+P4S+P11F+K34Y+T65A+Q327F+D445N+V447S+E501V+Y504T; or
P2N+P4S+P11F+R31 S+K33V+T65A+Q327F+D445N+V447S+E501V+Y504T; or
P2N+P4S+P11F+D26N+K34Y+T65A+Q327F+E501V+Y504T; or
P2N+P4S+P11F+T65A+F80*+Q327F+E501V+Y504T; or
P2N+P4S+P11F+T65A+K112S+Q327F+E501V+Y504T; or
P2N+P4S+P11F+T65A+Q327F+E501V+Y504T+T516P+K524T+G526A; or
P2N+P4S+P11F+T65A+Q327F+E501V+N502T+Y504*; or
P2N+P4S+P11F+T65A+Q327F+E501V+Y504T; or
P2N+P4S+P11F+T65A+S103N+Q327F+E501V+Y504T; or
K5A+P11F+T65A+Q327F+E501V+Y504T; or
P2N+P4S+P11F+T65A+Q327F+E501V+Y504T+T516P+K524T+G526A; or
P2N+P4S+P11F+T65A+K79A+Q327F+E501V+Y504T; or
P2N+P4S+P11F+T65A+K79G+Q327F+E501V+Y504T; or
P2N+P4S+P11F+T65A+K79I+Q327F+E501V+Y504T; or
P2N+P4S+P11F+T65A+K79L+Q327F+E501V+Y504T; or
P2N+P4S+P11F+T65A+K79S+Q327F+E501V+Y504T; or
P2N+P4S+P11F+T65A+L72V+Q327F+E501V+Y504T; or
S255N+Q327F+E501V+Y504T; or
P2N+P4S+P11F+T65A+E74N+V79K+Q327F+E501V+Y504T; or
P2N+P4S+P11F+T65A+G220N+Q327F+E501V+Y504T; or
P2N+P4S+P11F+T65A+Y245N+Q327F+E501V+Y504T; or
P2N+P4S+P11F+T65A+Q253N+Q327F+E501V+Y504T; or
P2N+P4S+P11F+T65A+D279N+Q327F+E501V+Y504T; or
P2N+P4S+P11F+T65A+Q327F+S359N+E501V+Y504T; or
P2N+P4S+P11F+T65A+Q327F+D370N+E501V+Y504T; or
P2N+P4S+P11F+T65A+Q327F+V460S+E501V+Y504T; or
P2N+P4S+P11F+T65A+Q327F+V460T+P468T+E501V+Y504T; or
P2N+P4S+P11F+T65A+Q327F+T463N+E501V+Y504T; or
P2N+P4S+P11F+T65A+Q327F+S465N+E501V+Y504T; or
P2N+P4S+P11F+T65A+Q327F+T477N+E501V+Y504T.

In a preferred embodiment the glucoamylase present and/or added in liquefaction is the *Penicillium oxalicum* glucoamylase having a K79V substitution and preferably further one of the following substitutions:
P11F+T65A+Q327F;
P2N+P4S+P11F+T65A+Q327F (using SEQ ID NO: 14 for numbering).

In an embodiment the glucoamylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 14 herein.

The glucoamylase may be added in amounts from 0.1-100 micro grams EP/g, such as 0.5-50 micro grams EP/g, such as 1-25 micrograms EP/g, such as 2-12 micrograms EP/g DS.

Glucoamylase Present and/or Added in Saccharification and/or Fermentation

A glucoamylase is present and/or added in saccharification and/or fermentation, preferably simultaneous saccharification and fermentation (SSF), in a process of the invention (i.e., oil recovery process and fermentation product production process).

In an embodiment the glucoamylase present and/or added in saccharification and/or fermentation is of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii*.

In an embodiment the glucoamylase is derived from *Talaromyces*, such as a strain of *Talaromyces emersonii*, such as the one shown in SEQ ID NO: 19 herein, In an embodiment the glucoamylase is selected from the group consisting of:
(i) a glucoamylase comprising the mature polypeptide of SEQ ID NO: 19 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 19 herein.

In an embodiment the glucoamylase is derived from a strain of the genus *Pycnoporus*, in particular a strain of *Pycnoporus sanguineus* described in WO 2011/066576 (SEQ ID NOs 2, 4 or 6), such as the one shown as SEQ ID NO: 4 in WO 2011/066576 or SEQ ID NO: 18 herein.

In an embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803 or SEQ ID NO: 15 herein.

In a preferred embodiment the glucoamylase is derived from *Gloephyllum serpiarium*, such as the one shown in SEQ ID NO: 15 herein. In an embodiment the glucoamylase is selected from the group consisting of:
(i) a glucoamylase comprising the mature polypeptide of SEQ ID NO: 15 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 15 herein.

In another embodiment the glucoamylase is derived from *Gloeophyllum trabeum* such as the one shown in SEQ ID NO: 17 herein. In an embodiment the glucoamylase is selected from the group consisting of:
(i) a glucoamylase comprising the mature polypeptide of SEQ ID NO: 17 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 17 herein.

In an embodiment the glucoamylase is derived from a strain of the genus *Nigrofomes*, in particular a strain of *Nigrofomes* sp. disclosed in WO 2012/064351 (SEQ ID NO: 2) (all references hereby incorporated by reference).

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL and AMG™ E (from Novozymes NS); OPTIDEX™ 300, GC480, GC417 (from DuPont.); AMIGASE™ and AMIGASE™ PLUS (from DSM); G-ZYME™ G900, G-ZYME™ and G990 ZR (from DuPont).

According to a preferred embodiment of the invention the glucoamylase is present and/or added in saccharification and/or fermentation in combination with an alpha-amylase. Examples of suitable alpha-amylase are described below.

Alpha-Amylase Present and/or Added in Saccharification and/or Fermentation

In an embodiment an alpha-amylase is present and/or added in saccharification and/or fermentation in a process of the invention. In a preferred embodiment the alpha-amylase is of fungal or bacterial origin. In a preferred embodiment the alpha-amylase is a fungal acid stable alpha-amylase. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

In a preferred embodiment the alpha-amylase present and/or added in saccharification and/or fermentation is derived from a strain of the genus *Rhizomucor*, preferably a strain the *Rhizomucor pusillus*, such as one shown in SEQ ID NO: 3 in WO 2013/006756, such as a *Rhizomucor pusillus* alpha-amylase hybrid having an *Aspergillus niger* linker and starch-bonding domain, such as the one shown in SEQ ID NO: 16 herein, or a variant thereof.

In an embodiment the alpha-amylase present and/or added in saccharification and/or fermentation is selected from the group consisting of:
(i) an alpha-amylase comprising the mature polypeptide of SEQ ID NO: 16 herein;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 16 herein.

In a preferred embodiment the alpha-amylase is a variant of the alpha-amylase shown in SEQ ID NO: 13 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 16 for numbering).

In an embodiment the alpha-amylase is derived from a *Rhizomucor pusillus* with an *Aspergillus niger* glucoamylase linker and starch-binding domain (SBD), preferably disclosed as SEQ ID NO: 13 herein, preferably having one or more of the following substitutions: G128D, D143N, preferably G128D+D143N (using SEQ ID NO: 13 for numbering).

In an embodiment the alpha-amylase variant present and/or added in saccharification and/or fermentation has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 16 herein.

In an embodiment the alpha-amylase is derived from a strain of *Aspergillus*, such as *Aspergillus niger*, such as the one shown as SEQ ID NO: 9 in U.S. Pat. No. 8,048,657; or *Aspergillus kawachi*, such as the one shown as SEQ ID NO: 5 in U.S. Pat. No. 8,048,657.

In an embodiment the alpha-amylase is derived from a strain of *Trichoderma reesei*, such as the one shown in SEQ ID NO: 13 in U.S. Pat. No. 8,048,657.

In a preferred embodiment the ratio between glucoamylase and alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70.

Pullulanase Present and/or Added in Liquefaction and/or Saccharification and/or Fermentation.

A pullulanase may be present and/or added during liquefaction step a) and/or saccharification step b) or fermentation step c) or simultaneous saccharification and fermentation.

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

Contemplated pullulanases according to the present invention include the pullulanases from *Bacillus amyloderamificans* disclosed in U.S. Pat. No. 4,560,651 (hereby incorporated by reference), the pullulanase disclosed as SEQ ID NO: 2 in WO 01/151620 (hereby incorporated by reference), the *Bacillus deramificans* disclosed as SEQ ID NO: 4 in WO 01/151620 (hereby incorporated by reference), and the pullulanase from *Bacillus acidopullulyticus* disclosed as SEQ ID NO: 6 in WO 01/151620 (hereby incorporated by reference) and also described in FEMS Mic. Let. (1994) 115, 97-106.

Additional pullulanases contemplated according to the present invention included the pullulanases from *Pyrococcus woesei*, specifically from *Pyrococcus woesei* DSM No. 3773 disclosed in WO92/02614.

In an embodiment the pullulanase is a family GH57 pullulanase, wherein the pullulanase preferably includes an X47 domain as disclosed in WO 2011/087836. More specifically the the pullulanase may be derived from a strain from the genus *Thermococcus*, including *Thermococcus litoralis* and *Thermococcus hydrothermalis* or a hybrid thereof. In an embodiment the pullulanase is the truncated *Thermococcus hydrothermalis* pullulanase at site X4 or a *T. hydrothermalis/T. litoralis* hybrid enzyme with truncation at site X4 disclosed in WO 2011/087836 or shown in SEQ ID NO: 12 herein.

In another embodiment the pullulanase is one comprising an X46 domain disclosed in WO 2011/076123 (Novozymes).

The pullulanase may according to the invention be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullulanase activity may be determined as NPUN. An Assay for determination of NPUN is described in the "Materials & Methods"-section below.

Suitable commercially available pullulanase products include PROMOZYME D, PROMOZYME™ D2 (Novozymes NS, Denmark), OPTIMAX L-300 (Genencor Int., USA), and AMANO 8 (Amano, Japan).

Further Aspects of Processes of the Invention

Prior to liquefaction step a), processes of the invention, including processes of extracting/recovering oil and processes for producing fermentation products, may comprise the steps of:

i) reducing the particle size of the starch-containing material, preferably by dry milling;
ii) forming a slurry comprising the starch-containing material and water.

In an embodiment at least 50%, preferably at least 70%, more preferably at least 80%, especially at least 90% of the starch-containing material fit through a sieve with #6 screen.

In an embodiment the pH during liquefaction is between above 4.5-6.5, such as 4.5-5.0, such as around 4.8, or a pH between 5.0-6.2, such as 5.0-6.0, such as between 5.0-5.5, such as around 5.2, such as around 5.4, such as around 5.6, such as around 5.8.

In an embodiment the temperature during liquefaction is above the initial gelatinization temperature, preferably in the range from 70-100° C., such as between 75-95° C., such as between 75-90° C., preferably between 80-90° C., especially around 85° C.

In an embodiment a jet-cooking step is carried out before liquefaction in step a). In an embodiment the jet-cooking is carried out at a temperature between 110-145° C., preferably 120-140° C., such as 125-135° C., preferably around 130° C. for about 1-15 minutes, preferably for about 3-10 minutes, especially around about 5 minutes.

In a preferred embodiment saccharification and fermentation is carried out sequentially or simultaneously.

In an embodiment saccharification is carried out at a temperature from 20-75° C., preferably from 40-70° C., such as around 60° C., and at a pH between 4 and 5.

In an embodiment fermentation or simultaneous saccharification and fermentation (SSF) is carried out carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

In a preferred embodiment the fermentation product is recovered after fermentation, such as by distillation.

In an embodiment the fermentation product is an alcohol, preferably ethanol, especially fuel ethanol, potable ethanol and/or industrial ethanol.

In an embodiment the starch-containing starting material is whole grains. In an embodiment the starch-containing material is selected from the group of corn, wheat, barley, rye, milo, sago, cassava, manioc, tapioca, sorghum, rice, and potatoes.

In an embodiment the fermenting organism is yeast, preferably a strain of *Saccharomyces*, especially a strain of *Saccharomyces cerevisae*.

In an embodiment the alpha-amylase is a bacterial or fungal alpha-amylase.

In an embodiment saccharification step b) and fermentation step c) are carried out simultaneously or sequentially.

In an embodiment the temperature in step (a) is above the initial gelatinization temperature, such as at a temperature between 80-90° C., such as around 85° C.

In an embodiment a process of the invention further comprises a pre-saccharification step, before saccharification step b), carried out for 40-90 minutes at a temperature between 30-65° C. In an embodiment saccharification is carried out at a temperature from 20-75° C., preferably from 40-70° C., such as around 60° C., and at a pH between 4 and 5. In an embodiment fermentation step c) or simultaneous saccharification and fermentation (SSF) (i.e., steps b) and c)) are carried out carried out at a temperature from 25° C. to 40° C., such as from 28° C. to 35° C., such as from 30° C. to 34° C., preferably around about 32° C. In an embodiment the fermentation step c) or simultaneous saccharification and fermentation (SSF) (i.e., steps b) and c)) are ongoing for 6 to 120 hours, in particular 24 to 96 hours.

In an embodiment separation in step e) is carried out by centrifugation, preferably a decanter centrifuge, filtration, preferably using a filter press, a screw press, a plate-and-frame press, a gravity thickener or decker.

In an embodiment the fermentation product is recovered by distillation.

Examples of Specific Process Embodiments of the Invention
Oil Recovery:

In a preferred embodiment the invention concerns processes of recovering oil comprising the steps of:
a) liquefying starch-containing material at a temperature above the initial gelatinization temperature using:
   Bacillus stearothermophilus alpha-amylase comprising a double deletion at positions I181+G182 using SEQ ID NO: 1 for numbering;
   more than 0.5 micro gram Pyrococcus furiosus protease per gram dry solids (DS);
   Penicillium oxalicum shown in SEQ ID NO: 14 comprising a K79V substitution;
b) saccharifying using a glucoamylase;
c) fermenting using a fermenting organism.
d) recovering the fermentation product to form whole stillage;
e) separating the whole stillage into thin stillage and wet cake;
f) optionally concentrating the thin stillage into syrup;
wherein oil is recovered from the:
   liquefied starch-containing material after step a); and/or
   downstream from fermentation step c).

In a preferred embodiment the invention concerns processes of recovering oil comprising the steps of:
a) liquefying starch-containing material at a temperature above the initial gelatinization temperature using:
   Bacillus stearothermophilus alpha-amylase comprising a double deletion at positions:
   I181+G182 and the following substitutions N193F+V59A+Q89R+E129V+K177L+R179E+Q254S+M284V truncated to 491 amino acids (using SEQ ID NO: 1 for numbering).
   more than 0.5 micro gram Pyrococcus furiosus protease per gram dry solids (DS);
   Penicillium oxalicum glucoamylase having the following mutations: K79V+P2N+P4S+P11F+T65A+Q327F (using SEQ ID NO: 14 for numbering);
b) saccharifying using a glucoamylase;
c) fermenting using a fermenting organism.
d) recovering the fermentation product to form whole stillage;
e) separating the whole stillage into thin stillage and wet cake;
f) optionally concentrating the thin stillage into syrup;
wherein oil is recovered from the:
   liquefied starch-containing material after step a); and/or
   downstream from fermentation step c).

In a preferred embodiment the ratio between alpha-amylase and glucoamylase in liquefaction is between 1:1 and 1:10, such as around 1:2 (micro gram alpha-amylase per g DS: micro gram glucoamylase per gram DS).

In a preferred embodiment the ratio between alpha-amylase and protease in liquefaction is in the range between 1:1 and 1:25, such between 1:1.2 and as 1:10, such as around 1:1.4 (micro gram alpha-amylase per gram DS: micro gram protease per gram DS).

Producing Fermentation Products:

In a preferred embodiment the invention relates to processes for producing fermentation products from starch-containing material comprising the steps of:
a) liquefying the starch-containing material at a temperature above the initial gelatinization temperature using:
   an alpha-amylase derived from Bacillus stearothermophilus;
   more than 2 micro gram Pyrococcus furiosus protease per gram dry solids (DS); and
   optionally a Penicillium oxalicum glucoamylase;
b) saccharifying using a glucoamylase enzyme;
c) fermenting using a fermenting organism.

In a preferred embodiment the invention relates to processes for producing fermentation products from starch-containing material comprising the steps of:
a) liquefying the starch-containing material at a temperature above the initial gelatinization temperature using:
   an alpha-amylase, preferably derived from Bacillus stearothermophilus, having a T % (min) at pH 4.5, 85° C., 0.12 mM CaCl$_2$ of at least 10;
   more than 2 micro gram Pyrococcus furiosus protease per gram dry solids (DS); and
   optionally a glucoamylase;
b) saccharifying using a glucoamylase enzyme;
c) fermenting using a fermenting organism.

In a preferred embodiment the invention relates to processes for producing fermentation products from starch-containing material comprising the steps of:
a) liquefying the starch-containing material at a temperature above the initial gelatinization temperature using:
   an alpha-amylase, preferably derived from Bacillus stearothermophilus, having a T % (min) at pH 4.5, 85° C., 0.12 mM CaCl$_2$ of at least 10;
   more than 2 micro gram Pyrococcus furiosus protease per gram dry solids (DS); and
   a Penicillium oxalicum glucoamylasea;
b) saccharifying using a glucoamylase enzyme;
c) fermenting using a fermenting organism.

In a preferred embodiment the invention relates to processes for producing fermentation products from starch-containing material comprising the steps of:
a) liquefying the starch-containing material at a temperature above the initial gelatinization temperature using:
   an alpha-amylase derived from Bacillus stearothermophilus having a double deletion at positions I181+G182, and optional substitution N193F; further one of the following set of substitutions:
   E129V+K177L+R179E;
   V59A+Q89R+E129V+K177L+R179E+H208Y+K220P+N224L+Q254S;
   V59A+Q89R+E129V+K177L+R179E+Q254S+M284V;
   E129V+K177L+R179E+K220P+N224L+S242Q+Q254S (using SEQ ID NO: 1 herein for numbering);
   more than 2 micro gram Pyrococcus furiosus protease per gram dry solids (DS);
   a Penicillium oxalicum glucoamylase in SEQ ID NO: 14 having substitutions selected from the group of:
   K79V;
   K79V+P11F+T65A+Q327F; or
   K79V+P2N+P4S+P11F+T65A+Q327F; or
   K79V+P11F+D26C+K33C+T65A+Q327F; or
   K79V+P2N+P4S+P11F+T65A+Q327W+E501V+Y504T; or K79V+P2N+P4S+P11F+T65A+Q327F+E501V+
  Y504T; or
K79V+P11F+T65A+Q327W+E501V+Y504T (using
  SEQ ID NO: 14 for numbering);
  b) saccharifying using a glucoamylase enzyme;
  c) fermenting using a fermenting organism.

In a preferred embodiment the invention relates to processes for producing fermentation products from starch-containing material comprising the steps of:
  a) liquefying the starch-containing material at a pH in the range between from above 4.5-6.5 at a temperature between 80-90° C. using:
    an alpha-amylase derived from *Bacillus stearothermophilus* having a double deletion I181+G182 and optional substitution N193F; and further one of the following set of substitutions:
      E129V+K177L+R179E;
      V59A+Q89R+E129V+K177L+R179E+H208Y+
        K220P+N224L+Q254S;
      V59A+Q89R+E129V+K177L+R179E+Q254S+
        M284V;
      E129V+K177L+R179E+K220P+N224L+S242Q+
        Q254S (using SEQ ID NO: 1 herein for numbering);
    more than 2 micro gram, such as between 2-5 micro gram, preferably around or more than 3 micro gram *Pyrococcus furiosus* protease per gram DS dry solids (DS);
    a *Penicillium oxalicum* glucoamylase in SEQ ID NO: 14 having substitutions selected from the group of:
      K79V;
      K79V+P11F+T65A+Q327F; or
      K79V+P2N+P4S+P11F+T65A+Q327F; or
      K79V+P11F+D26C+K33C+T65A+Q327F; or
      K79V+P2N+P4S+P11F+T65A+Q327W+E501V+
        Y504T; or
      K79V+P2N+P4S+P11F+T65A+Q327F+E501V+
        Y504T; or
      K79V+P11F+T65A+Q327W+E501V+Y504T (using
        SEQ ID NO: 14 for numbering);
  b) saccharifying using a glucoamylase enzyme;
  c) fermenting using a fermenting organism.

In a preferred embodiment the invention relates to processes for producing fermentation products from starch-containing material comprising the steps of:
  a) liquefying the starch-containing material at a pH in the range between from above 4.5-6.5 at a temperature between 80-90° C. using:
    an alpha-amylase derived from *Bacillus stearothermophilus* having a double deletion I181+G182 and substitution N193F; and further one of the following set of substitutions:
      E129V+K177L+R179E;
      V59A+Q89R+E129V+K177L+R179E+H208Y+
        K220P+N224L+Q254S;
      V59A+Q89R+E129V+K177L+R179E+Q254S+
        M284V;
      E129V+K177L+R179E+K220P+N224L+S242Q+
        Q254S (using SEQ ID NO: 1 herein for numbering);
    more than 2 micro gram, such as between 2-5 micro gram, preferably around or more than 3 micro gram *Pyrococcus furiosus* protease per gram DS dry solids (DS)
    a *Penicillium oxalicum* glucoamylase in SEQ ID NO: 14 having substitutions selected from the group of:
      K79V;
      K79V+P11F+T65A+Q327F; or
      K79V+P2N+P4S+P11F+T65A+Q327F; or
      K79V+P11F+D26C+K33C+T65A+Q327F; or
      K79V+P2N+P4S+P11F+T65A+Q327W+E501V+
        Y504T; or
      K79V+P2N+P4S+P11F+T65A+Q327F+E501V+
        Y504T; or
      K79V+P11F+T65A+Q327W+E501V+Y504T (using
        SEQ ID NO: 14 for numbering);
  b) saccharifying using a *Rhizomucor pusillus* glucoamylase with an *Aspergillus niger* glucoamylase linker and starch-binding domain (SBD), preferably disclosed as SEQ ID NO: 13 herein, preferably having one or more of the following substitutions: G128D, D143N, preferably G128D+D143N (using SEQ ID NO: 13 for numbering);
  c) fermenting using a fermenting organism.

In an embodiment the ratio between alpha-amylase and glucoamylase in liquefaction is between 1:1 and 1:10, such as around 1:2 (micro gram alpha-amylase per g DS: micro gram glucoamylase per gram DS).

In an embodiment the ratio between alpha-amylase and protease in liquefaction is in the range between 1:1 and 1:25, such between 1:1.2 and as 1:10, such as around 1:1.4 (micro gram alpha-amylase per g DS: micro gram protease per gram DS).

Fermentation Medium

The environment in which fermentation is carried out is often referred to as the "fermentation media" or "fermentation medium". The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as ethanol. Examples of fermenting organisms include fungal organisms, such as yeast. Preferred yeast includes strains of *Saccharomyces* spp., in particular, *Saccharomyces cerevisiae*.

Suitable concentrations of the viable fermenting organism during fermentation, such as SSF, are well known in the art or can easily be determined by the skilled person in the art. In one embodiment the fermenting organism, such as ethanol fermenting yeast, (e.g., *Saccharomyces cerevisiae*) is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Examples of commercially available yeast includes, e.g., RED START™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived therefrom, or cereals. Contemplated are also waxy and non-waxy types of corn and barley. In a preferred embodiment the starch-containing material, used for ethanol production according to the invention, is corn or wheat.

Fermentation Products

The term "fermentation product" means a product produced by a process including a fermentation step using a fermenting organism. Fermentation products contemplated according to the invention include alcohols (e.g., ethanol, methanol, butanol; polyols such as glycerol, sorbitol and inositol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferably processes of the invention are used for producing an alcohol, such as ethanol. The fermentation product, such as ethanol, obtained according to the invention, may be used as fuel, which is typically blended with gasoline. However, in the case of ethanol it may also be used as potable ethanol.

Recovery of Fermentation Products

Subsequent to fermentation, or SSF, the fermentation product may be separated from the fermentation medium. The slurry may be distilled to extract the desired fermentation product (e.g., ethanol). Alternatively the desired fermentation product may be extracted from the fermentation medium by micro or membrane filtration techniques. The fermentation product may also be recovered by stripping or other method well known in the art.

Recovery of Oil

According to the invention oil is recovered during and/or after liquefying, from the whole stillage, from the thin stillage or from the syrup. Oil may be recovered by extraction. In one embodiment oil is recovered by hexane extraction. Other oil recovery technologies well-known in the art may also be used.

An Enzyme Composition of the Invention

An enzyme composition of the invention comprises an alpha-amylase and a *Pyrococcus furiosus* protease suitable for use in a liquefaction step in a process of the invention.

An enzyme composition of the invention comprises:
i) *Bacillus* sp. alpha-amylase, or a variant thereof;
ii) *Pyrococcus furiosus* protease;
wherein the ratio between alpha-amylase and protease is in the range from 1:1 and 1:25 (micro gram alpha-amylase: micro gram protease).

In a preferred embodiment the ratio between alpha-amylase and protease is in the range between 1:1.2 and 1:10, such as around 1:1.4 (micro gram alpha-amylase:micro gram protease).

In a preferred embodiment the enzyme composition of the invention comprises a glucoamylase and the ratio between alpha-amylase and glucoamylase in liquefaction is between 1:1 and 1:10, such as around 1:2 (micro gram alpha-amylase:micro gram glucoamylase).

In an embodiment the alpha-amylase in the enzyme composition of the invention is a bacterial or fungal alpha-amylase.

In an embodiment the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein.

In an embodiment the *Bacillus stearothermophilus* alpha-amylase or variant thereof is truncated, preferably to have around 491 amino acids, such as from 480-495 amino acids.

In an embodiment the *Bacillus stearothermophilus* alpha-amylase has a double deletion, preferably at positions I181+G182 and optionally a N193F substitution, or double deletion of R179 and G180 (using SEQ ID NO: 1 for numbering).

In an embodiment the *Bacillus stearothermophilus* alpha-amylase has a substitution at position S242, preferably S242Q substitution.

In an embodiment the *Bacillus stearothermophilus* alpha-amylase has a substitution at position E188, preferably E188P substitution.

In an embodiment the alpha-amylase has a T½ (min) at pH 4.5, 85° C., 0.12 mM $CaCl_2$) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

In an embodiment the alpha-amylase is selected from the group of *Bacillus stearothermphilus* alpha-amylase variants with the following mutations:
I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A Q89R+E129V+K177L+R179E+Q254S+M284V; and
I181*+G182*+N193F+E129V+K177L+R179E+K220P+N224L+S242Q+Q254S (using SEQ ID NO: 1 herein for numbering).

In an embodiment the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 1 herein.

In another embodiment the alpha-amylase is a *Bacillus licheniformis* alpha-amylase, or a variant thereof.

In an embodiment the *Bacillus licheniformis* alpha-amylase is the one shown in SEQ ID NO: 21 herein.

In an embodiment the alpha-amylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% identity to the mature part of the polypeptide of SEQ ID NO: 21 herein.

In an embodiment the enzyme composition comprises a *Bacillus licheniformis* alpha-amylase and a *Pyrococcus furiosus* protease.

In an embodiment the enzyme composition further comprises a glucoamylase.

In an embodiment the *Pyrococcus furiosus* is the one shown in SEQ ID NO: 13 herein.

In an embodiment the *Pyrococcus furiosus* protease is one having at least 80%, such as at least 85%, such as at least 90%, such as at least 95%, such as at least 96%, such as at least 97%, such as at least 98%, such as at least 99% identity to SEQ ID NO: 13 herein.

In an embodiment the enzyme composition further comprises a glucoamylase shown in SEQ ID NO: 14, or a variant thereof.

In an embodiment the glucoamylase has a heat stability at 85° C., pH 5.3, of at least 20%, such as at least 30%, preferably at least 35% determined as disclosed in Example 2 herein or Example 8 in WO 2011/127802.

In an embodiment the glucoamylase has a relative activity pH optimum at pH 5.0 of at least 90%, preferably at least 95%, preferably at least 97% determined as disclosed in Example 2 herein or Example 8 in WO 2011/127802.

In an embodiment the glucoamylase has a pH stability at pH 5.0 of at least at least 80%, at least 85%, at least 90% determined as disclosed in Example 2 herein or Example 8 in WO 2011/127802.

In an embodiment the glucoamylase is derived from a strain of the genus *Penicillium*, especially a strain of *Penicillium oxalicum* disclosed as SEQ ID NO: 2 in WO 2011/127802 or SEQ ID NOs: 9 or 14 herein.

In an embodiment the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 9 or 14 herein.

In an embodiment the glucoamylase has a thermostability of at least 80° C., preferably at least 82° C., such as at least 84° C., such as at least 86° C., such as at least 88° C. at pH 4.0 determined as Differential Scanning calorimitry (DSC) as described in Example 3 below.

In an embodiment the glucoamylase has a thermostability of at least 80° C., preferably at least 82° C., such as at least 84° C., such as at least 86° C., such as at least 88° C., such as at least 90° C. at pH 4.8 determined as Differential Scanning calorimitry (DSC) as described in Example 3 below.

Examples of specifically contemplated glucoamylases can be found in Example 3 (Table 6) below.

In an embodiment the glucoamylase is a variant of the *Penicillium oxalicum* glucoamylase disclosed as SEQ ID NO: 2 in WO 2011/127802 or SEQ ID NO: 14 herein having a K79V substitution (using the mature sequence shown in SEQ ID NO: 14 for numbering) such as a variant disclosed in WO 2013/053801.

In an embodiment the *Penicillium oxalicum* glucoamylase has a K79V substitution (using SEQ ID NO: 14 for numbering) and preferably further one of the following substitutions:

T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+I172V+Q327F+E501V+Y504T; or
P2N+P4S+P11F+T65A+Q327F+S377T+E501V+Y504T; or
P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or

P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or
P2N+P4S+P11F+T65A+Q327F+E501V+Y504T+T568N; or
P2N+P4S+P11F+T65A+Q327F+E501V+Y504T+K524T+G526A; or
P2N+P4S+P11F+K34Y+T65A+Q327F+D445N+V447S+E501V+Y504T; or
P2N+P4S+P11F+R31 S+K33V+T65A+Q327F+D445N+V447S+E501V+Y504T; or
P2N+P4S+P11F+D26N+K34Y+T65A+Q327F+E501V+Y504T; or
P2N+P4S+P11F+T65A+F80*+Q327F+E501V+Y504T; or
P2N+P4S+P11F+T65A+K112S+Q327F+E501V+Y504T; or
P2N+P4S+P11F+T65A+Q327F+E501V+Y504T+T516P+K524T+G526A; or
P2N+P4S+P11F+T65A+Q327F+E501V+N502T+Y504*; or
P2N+P4S+P11F+T65A+Q327F+E501V+Y504T; or
P2N+P4S+P11F+T65A+S103N+Q327F+E501V+Y504T; or
K5A+P11F+T65A+Q327F+E501V+Y504T; or
P2N+P4S+P11F+T65A+Q327F+E501V+Y504T+T516P+K524T+G526A; or
P2N+P4S+P11F+T65A+K79A+Q327F+E501V+Y504T; or
P2N+P4S+P11F+T65A+K79G+Q327F+E501V+Y504T; or
P2N+P4S+P11F+T65A+K79I+Q327F+E501V+Y504T; or
P2N+P4S+P11F+T65A+K79L+Q327F+E501V+Y504T; or
P2N+P4S+P11F+T65A+K79S+Q327F+E501V+Y504T; or
P2N+P4S+P11F+T65A+L72V+Q327F+E501V+Y504T; or
S255N+Q327F+E501V+Y504T; or
P2N+P4S+P11F+T65A+E74N+V79K+Q327F+E501V+Y504T; or
P2N+P4S+P11F+T65A+G220N+Q327F+E501V+Y504T; or
P2N+P4S+P11F+T65A+Y245N+Q327F+E501V+Y504T; or
P2N+P4S+P11F+T65A+Q253N+Q327F+E501V+Y504T; or
P2N+P4S+P11F+T65A+D279N+Q327F+E501V+Y504T; or
P2N+P4S+P11F+T65A+Q327F+S359N+E501V+Y504T; or
P2N+P4S+P11F+T65A+Q327F+D370N+E501V+Y504T; or
P2N+P4S+P11F+T65A+Q327F+V460S+E501V+Y504T; or
P2N+P4S+P11F+T65A+Q327F+V460T+P468T+E501V+Y504T; or
P2N+P4S+P11F+T65A+Q327F+T463N+E501V+Y504T; or
P2N+P4S+P11F+T65A+Q327F+S465N+E501V+Y504T; or
P2N+P4S+P11F+T65A+Q327F+T477N+E501V+Y504T.

In an embodiment the glucoamylase is the *Penicillium oxalicum* glucoamylase having a K79V substitution (using SEQ ID NO: 14 for numbering) and further one of the following substitutions:
P11F+T65A+Q327F
P2N+P4S+P11F+T65A+Q327F (using SEQ ID NO: 14 for numbering).

In an embodiment the glucoamylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 14 herein.

In an embodiment the composition further comprising a pullulanase.

In an embodiment the pullulanase is a family GH57 pullulanase, wherein the pullulanase preferably includes an X47 domain as disclosed in WO 2011/087836.

In an embodiment the pullulanase is derived from a strain from the genus *Thermococcus*, including *Thermococcus litoralis* and *Thermococcus hydrothermalis* or a hybrid thereof.

In an embodiment the pullulanase is the truncated *Thermococcus hydrothermalis* pullulanase at site X4 or a *T. hydrothermalis/T. litoralis* hybrid enzyme with truncation site X4 disclosed in WO 2011/087836 or shown in SEQ ID NO: 12 herein.

In an embodiment the enzyme composition comprises
*Bacillus stearothermophilus* alpha-amylase, or a variant thereof;
*Pyrococcus furiosus* protease; and
*Penicillium oxalicum* glucoamylase,
wherein the ratio between alpha-amylase and protease is in the range from 1:1 and 1:25 (micro gram alpha-amylase: micro gram protease).

In an embodiment the enzyme composition of the invention comprises:
an alpha-amylase, preferably derived from *Bacillus stearothermophilus*, having a T½ (min) at pH 4.5, 85° C., 0.12 mM $CaCl_2$ of at least 10;
*Pyrococcus furiosus* protease; and
*Penicillium oxalicum* glucoamylase,
wherein the ratio between alpha-amylase and protease is in the range from 1:1 and 1:25 (micro gram alpha-amylase: micro gram protease).

In an embodiment the enzyme composition comprises:
an alpha-amylase derived from *Bacillus stearothermophilus* having a double deletion I181+G182 and substitution N193F; and further one of the following set of substitutions:
E129V+K177L+R179E;
V59A+Q89R+E129V+K177L+R179E+H208Y+K220P+N224L+Q254S;
V59A+Q89R+E129V+K177L+R179E+Q254S+M284V;
E129V+K177L+R179E+K220P+N224L+S242Q+Q254S (using SEQ ID NO: 1 herein for numbering);
*Pyrococcus furiosus* protease; and
*Penicillium oxalicum* glucoamylase in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+Y504T; or
K79V+P2N+P4S+P11F+T65A+Q327F+E501V+Y504T; or
K79V+P11F+T65A+Q327W+E501V+Y504T (using SEQ ID NO: 14 for numbering), wherein the ratio between alpha-amylase and protease is in the range from 1:1 and 1:25 (micro gram alpha-amylase:micro gram protease).

In an embodiment the ratio between alpha-amylase and protease is in the range between 1:1.2 and 1:10, such as around 1:1.4 (micro gram alpha-amylase:micro gram protease).

In an embodiment the ratio between alpha-amylase and glucoamylase is between 1:1 and 1:10, such as around 1:2 (micro gram alpha-amylase:micro gram glucoamylase).

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Materials & Methods
Materials:
Alpha-Amylase A (AAA): *Bacillus stearothermophilus* alpha-amylase with the mutations I181*+G182*+N193F truncated to 491 amino acids (SEQ ID NO: 1)

Alpha-Amylase 1407 (AA1407): *Bacillus stearothermophilus* alpha-amylase with the mutations I181*+G182*+N193F+V59A+Q89R+E129V+K177L+R179E+H208Y+K220P+N224L+Q254S truncated to 491 amino acids (SEQ ID NO: 1)

Alpha-Amylase 369 (AA369): *Bacillus stearothermophilus* alpha-amylase with the mutations: I181*+G182*+N193F+V59A+Q89R+E129V+K177L+R179E+Q254S+M284V truncated to 491 amino acids (SEQ ID NO: 1).

Protease Pfu: Protease derived from *Pyrococcus furiosus* shown in SEQ ID NO: 13 herein.

Glucoamylase Po: Mature part of the *Penicillium oxalicum* glucoamylase disclosed as SEQ ID NO: 2 in WO 2011/127802 and shown in SEQ ID NO: 14 herein.

Glucoamylase Po PE001: Variant of *Penicillium oxalicum* glucoamylase having the following mutation: K79V (using SEQ ID NO: 14 for numbering).

Glucoamylase Po 498 (GA498): Variant of *Penicillium oxalicum* glucoamylase having the following mutations: K79V+P2N+P4S+P11F+T65A+Q327F (using SEQ ID NO: 14 for numbering).

Glucoamylase A: Blend comprising *Talaromyces emersonii* glucoamylase disclosed as SEQ ID NO: 34 in WO99/28448, *Trametes cingulata* glucoamylase disclosed as SEQ ID NO: 2 in WO 06/69289, and *Rhizomucor pusillus* alpha-amylase with *Aspergillus niger* glucoamylase linker and starch binding domain (SBD) disclosed in SEQ ID NO: 16 herein having the following substitutions G128D+D143N (activity ratio in AGU:AGU:FAU-F is about 20:5:1).

Glucoamylase U: Blend comprising *Talaromyces emersonii* glucoamylase disclosed as SEQ ID NO: 34 in WO99/28448, *Trametes cingulata* glucoamylase disclosed as SEQ ID NO: 2 in WO 06/69289 and *Rhizomucor pusillus* alpha-amylase with *Aspergillus niger* glucoamylase linker and starch binding domain (SBD) disclosed disclosed in SEQ ID NO: 16 herein (activity ratio in AGU: AGU:FAU-F is about 65:15:1).

Protease X: Metallo protease derived from *Thermoascus aurantiacus* CGMCC No. 0670 disclosed as amino acids 1-177 in SEQ ID NO: 3 herein and amino acids 1-177 in SEQ ID NO: 2 in WO 2003/048353

Yeast:
ETHANOL RED™ from Fermentis, USA
Methods
Identity: The relatedness between two amino acid sequences or between two nucleotide sequences is described by the parameter "identity".

For purposes of the present invention the degree of identity between two amino acid sequences, as well as the degree of identity between two nucleotide sequences, may be determined by the program "align" which is a Needleman-Wunsch alignment (i.e. a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotides.

"Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183:63-98). FASTA protein alignments use the Smith-Waterman algorithm with no limitation on gap size (see "Smith-Waterman algorithm", T. F. Smith and M. S. Waterman (1981) J. Mol. Biol. 147:195-197).

Protease Assays
AZCL-casein Assay
A solution of 0.2% of the blue substrate AZCL-casein is suspended in Borax/NaH$_2$PO$_4$ buffer pH9 while stirring. The solution is distributed while stirring to microtiter plate (100 microL to each well), 30 microL enzyme sample is added and the plates are incubated in an Eppendorf Thermomixer for 30 minutes at 45° C. and 600 rpm. Denatured enzyme sample (100° C. boiling for 20 min) is used as a blank. After incubation the reaction is stopped by transferring the microtiter plate onto ice and the colored solution is separated from the solid by centrifugation at 3000 rpm for 5 minutes at 4° C. 60 microL of supernatant is transferred to a microtiter plate and the absorbance at 595 nm is measured using a BioRad Microplate Reader.

pNA-assay
50 microL protease-containing sample is added to a microtiter plate and the assay is started by adding 100 microL 1 mM pNA substrate (5 mg dissolved in 100 microL DMSO and further diluted to 10 mL with Borax/NaH$_2$PO$_4$ buffer pH 9.0). The increase in OD$_{405}$ at room temperature is monitored as a measure of the protease activity.

Glucoamylase Activity (AGU)
Glucoamylase activity may be measured in Glucoamylase Units (AGU).

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes NS, Denmark, which folder is hereby included by reference.

Acid Alpha-Amylase Activity

When used according to the present invention the activity of an acid alpha-amylase may be measured in AFAU (Acid Fungal Alpha-amylase Units) or FAU-F.

Acid Alpha-amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

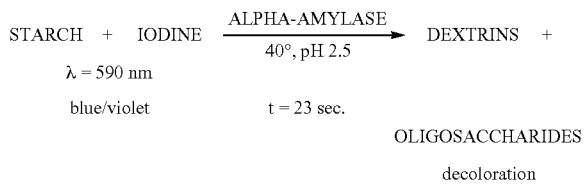

Standard Conditions/Reaction Conditions:
Substrate: Soluble starch, approx. 0.17 g/L
Buffer: Citrate, approx. 0.03 M
Iodine (12): 0.03 g/L
$CaCl_2$: 1.85 mM
pH: 2.50±0.05
Incubation temperature: 40° C.
Reaction time: 23 seconds
Wavelength: 590 nm
Enzyme concentration: 0.025 AFAU/mL
Enzyme working range: 0.01-0.04 AFAU/mL
A folder EB-SM-0259.02/01 describing this analytical method in more detail is available upon request to Novozymes NS, Denmark, which folder is hereby included by reference.

Determination of FAU-F

FAU-F Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes NS, Denmark, which folder is hereby included by reference.

Alpha-amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum soluble.

A folder EB-SM-0009.02/01 describing this analytical method in more detail is available upon request to Novozymes NS, Denmark, which folder is hereby included by reference.

Determination of Pullulanase Activity (NPUN)

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan.

1 mL diluted sample or standard is incubated at 40° C. for 2 minutes. 0.5 mL 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

The present invention is described in further detail in the following examples which are offered to illustrate the present invention, but not in any way intended to limit the scope of the invention as claimed. All references cited herein are specifically incorporated by reference for that which is described therein.

EXAMPLES

Example 1

Stability of Alpha-Amylase Variants

The stability of a reference alpha-amylase (Bacillus stearothermophilus alpha-amylase with the mutations I181*+G182*+N193F truncated to 491 amino acids (SEQ ID NO: 1 numbering)) and alpha-amylase variants thereof was determined by incubating the reference alpha-amylase and variants at pH 4.5 and 5.5 and temperatures of 75° C. and 85° C. with 0.12 mM CaCl$_2$ followed by residual activity determination using the EnzChek® substrate (EnzChek® Ultra Amylase assay kit, E33651, Molecular Probes).

Purified enzyme samples were diluted to working concentrations of 0.5 and 1 or 5 and 10 ppm (micrograms/ml) in enzyme dilution buffer (10 mM acetate, 0.01% Triton X100, 0.12 mM CaCl$_2$, pH 5.0). Twenty microliters enzyme sample was transferred to 48-well PCR MTP and 180 microliters stability buffer (150 mM acetate, 150 mM MES, 0.01% Triton X100, 0.12 mM CaCl$_2$, pH 4.5 or 5.5) was added to each well and mixed. The assay was performed using two concentrations of enzyme in duplicates. Before incubation at 75° C. or 85° C., 20 microliters was withdrawn and stored on ice as control samples. Incubation was performed in a PCR machine at 75° C. and 85° C. After incubation samples were diluted to 15 ng/mL in residual activity buffer (100 mM Acetate, 0.01% Triton X100, 0.12 mM CaCl$_2$, pH 5.5) and 25 microliters diluted enzyme was transferred to black 384-MTP. Residual activity was determined using the EnzChek substrate by adding 25 microliters substrate solution (100 micrograms/ml) to each well. Fluorescence was determined every minute for 15 minutes using excitation filter at 485-P nm and emission filter at 555 nm (fluorescence reader is Polarstar, BMG). The residual activity was normalized to control samples for each setup.

Assuming logarithmic decay half life time (T½ (min)) was calculated using the equation: T % (min)=T(min)*LN (0.5)/LN (% RA/100), where T is assay incubation time in minutes, and % RA is % residual activity determined in assay.

Using this assay setup the half life time was determined for the reference alpha-amylase and variant thereof as shown in Table 1.

TABLE 1

| Mutations | T½ (min) (pH 4.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|
| Reference Alpha-Amylase A | 21 | 4 | 111 |
| Reference Alpha-Amylase A with the substitution V59A | 32 | 6 | 301 |
| Reference Alpha-Amylase A with the substitution V59E | 28 | 5 | 230 |
| Reference Alpha-Amylase A with the substitution V59I | 28 | 5 | 210 |
| Reference Alpha-Amylase A with the substitution V59Q | 30 | 6 | 250 |
| Reference Alpha-Amylase A with the substitutions V59A + Q89R + G112D + E129V + K177L + R179E + K220P + N224L + Q254S | 149 | 22 | ND |
| Reference Alpha-Amylase A with the substitutions V59A + Q89R + E129V + K177L + R179E + H208Y + K220P + N224L + Q254S | >180 | 28 | ND |
| Reference Alpha-Amylase A with the substitutions V59A + Q89R + E129V + K177L + R179E + K220P + N224L + Q254S + D269E + D281N | 112 | 16 | ND |
| Reference Alpha-Amylase A with the substitutions V59A + Q89R + E129V + K177L + R179E + K220P + N224L + Q254S + I270L | 168 | 21 | ND |
| Reference Alpha-Amylase A with the substitutions V59A + Q89R + E129V + K177L + R179E + K220P + N224L + Q254S + H274K | >180 | 24 | ND |
| Reference Alpha-Amylase A with the substitutions V59A + Q89R + E129V + K177L + R179E + K220P + N224L + Q254S + Y276F | 91 | 15 | ND |
| Reference Alpha-Amylase A with the substitutions V59A + E129V + R157Y + K177L + R179E + K220P + N224L + S242Q + Q254S | 141 | 41 | ND |
| Reference Alpha-Amylase A with the substitutions V59A + E129V + K177L + R179E + H208Y + K220P + N224L + S242Q + Q254S | >180 | 62 | ND |
| Reference Alpha-Amylase A with the substitutions V59A + E129V + K177L + R179E + K220P + N224L + S242Q + Q254S | >180 | 49 | >480 |

TABLE 1-continued

| Mutations | T½ (min) (pH 4.5, 75° C., 0.12 mM CaCl₂) | T½ (min) (pH 4.5, 85° C., 0.12 mM CaCl₂) | T½ (min) (pH 5.5, 85° C., 0.12 mM CaCl₂) |
|---|---|---|---|
| Reference Alpha-Amylase A with the substitutions V59A + E129V + K177L + R179E + K220P + N224L + S242Q + Q254S + H274K | >180 | 53 | ND |
| Reference Alpha-Amylase A with the substitutions V59A + E129V + K177L + R179E + K220P + N224L + S242Q + Q254S + Y276F | >180 | 57 | ND |
| Reference Alpha-Amylase A with the substitutions V59A + E129V + K177L + R179E + K220P + N224L + S242Q + Q254S + D281N | >180 | 37 | ND |
| Reference Alpha-Amylase A with the substitutions V59A + E129V + K177L + R179E + K220P + N224L + S242Q + Q254S + M284T | >180 | 51 | ND |
| Reference Alpha-Amylase A with the substitutions V59A + E129V + K177L + R179E + K220P + N224L + S242Q + Q254S + G416V | >180 | 45 | ND |
| Reference Alpha-Amylase A with the substitutions V59A + E129V + K177L + R179E + K220P + N224L + Q254S | 143 | 21 | >480 |
| Reference Alpha-Amylase A with the substitutions V59A + E129V + K177L + R179E + K220P + N224L + Q254S + M284T | >180 | 22 | ND |
| Reference Alpha-Amylase A with the substitutions A91L + M96I + E129V + K177L + R179E + K220P + N224L + S242Q + Q254S | >180 | 38 | ND |
| Reference Alpha-Amylase A with the substitutions E129V + K177L + R179E | 57 | 11 | 402 |
| Reference Alpha-Amylase A with the substitutions E129V + K177L + R179E + K220P + N224L + S242Q + Q254S | 174 | 44 | >480 |
| Reference Alpha-Amylase A with the substitutions E129V + K177L + R179E + K220P + N224L + S242Q + Q254S + Y276F + L427M | >180 | 49 | >480 |
| Reference Alpha-Amylase A with the substitutions E129V + K177L + R179E + K220P + N224L + S242Q + Q254S + M284T | >180 | 49 | >480 |
| Reference Alpha-Amylase A with the substitutions E129V + K177L + R179E + K220P + N224L + S242Q + Q254S + N376* + I377* | 177 | 36 | >480 |
| Reference Alpha-Amylase A with the substitutions E129V + K177L + R179E + K220P + N224L + Q254S | 94 | 13 | >480 |
| Reference Alpha-Amylase A with the substitutions E129V + K177L + R179E + K220P + N224L + Q254S + M284T | 129 | 24 | >480 |
| Reference Alpha-Amylase A with the substitutions E129V + K177L + R179E + S242Q | 148 | 30 | >480 |
| Reference Alpha-Amylase A with the substitutions E129V + K177L + R179V | 78 | 9 | >480 |
| Reference Alpha-Amylase A with the substitutions E129V + K177L + R179V + K220P + N224L + S242Q + Q254S | 178 | 31 | >480 |
| Reference Alpha-Amylase A with the substitutions K220P + N224L + S242Q + Q254S | 66 | 17 | >480 |
| Reference Alpha-Amylase A with the substitutions K220P + N224L + Q254S | 30 | 6 | 159 |

TABLE 1-continued

| Mutations | T½ (min) (pH 4.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|
| Reference Alpha-Amylase A with the substitution M284T | 35 | 7 | 278 |
| Reference Alpha-Amylase A with the substitutions M284V | 59 | 13 | ND |

ND not determined

The results demonstrate that the alpha-amylase variants have a significantly greater half-life and stability than the reference alpha-amylase.

Example 2

Characterization of *Penicillium oxalicum* Glucoamylase

The *Penicillium oxalicum* glucoamylase is disclosed in SEQ ID NO: 9 herein.

Substrate. Substrate: 1% soluble starch (Sigma S-9765) in deionized water

Reaction buffer: 0.1 M Acetate buffer at pH 5.3

Glucose concentration determination kit: Wako glucose assay kit (LabAssay glucose, WAKO, Cat#298-65701).

Reaction condition. 20 microL soluble starch and 50 microL acetate buffer at pH 5.3 were mixed. 30 microL enzyme solution (50 micro g enzyme protein/ml) was added to a final volume of 100 microL followed by incubation at 37° C. for 15 min.

The glucose concentration was determined by Wako kits. All the work carried out in parallel.

Temperature optimum. To assess the temperature optimum of the *Penicillium oxalicum* glucoamylase the "Reaction condition"-assay described above was performed at 20, 30, 40, 50, 60, 70, 80, 85, 90 and 95° C. The results are shown in Table 2.

TABLE 2

| Temperature optimum | | | | | | | | | | |
|---|---|---|---|---|---|---|---|---|---|---|
| | Temperature (° C.) | | | | | | | | | |
| | 20 | 30 | 40 | 50 | 60 | 70 | 80 | 85 | 90 | 95 |
| Relative activity (%) | 63.6 | 71.7 | 86.4 | 99.4 | 94.6 | 100.0 | 92.9 | 92.5 | 82.7 | 82.8 |

From the results it can be seen that the optimal temperature for *Penicillium oxalicum* glucoamylase at the given conditions is between 50° C. and 70° C. and the glucoamylase maintains more than 80% activity at 95° C.

Heat stability. To assess the heat stability of the *Penicillium oxalicum* glucoamylase the Reaction condition assay was modified in that the the enzyme solution and acetate buffer was preincubated for 15 min at 20, 30, 40, 50, 60, 70, 75, 80, 85, 90 and 95° C. Following the incubation 20 microL of starch was added to the solution and the assay was performed as described above.

The results are shown in Table 3.

TABLE 3

| Heat stability | | | | | | | | | | |
|---|---|---|---|---|---|---|---|---|---|---|
| | Temperature (° C.) | | | | | | | | | |
| | 20 | 30 | 40 | 50 | 60 | 70 | 80 | 85 | 90 | 95 |
| Relative activity (%) | 91.0 | 92.9 | 88.1 | 100.0 | 96.9 | 86.0 | 34.8 | 36.0 | 34.2 | 34.8 |

From the results it can be seen that *Penicillium oxalicum* glucoamylase is stable up to 70° C. after preincubation for 15 min in that it maintains more than 80% activity.

pH optimum. To assess the pH optimum of the *Penicillium oxalicum* glucoamylase the Reaction condition assay described above was performed at pH 2.0, 3.0, 3.5, 4.0, 4.5, 5.0, 6.0 7.0, 8.0, 9.0, 10.0 and 11.0. Instead of using the acetate buffer described in the Reaction condition assay the following buffer was used 100 mM Succinic acid, HEPES, CHES, CAPSO, 1 mM CaCl$_2$, 150 mM KCl, 0.01% Triton X-100, pH adjusted to 2.0, 3.0, 3.5, 4.0, 4.5, 5.0, 6.0 7.0, 8.0, 9.0, 10.0 or 11.0 with HCl or NaOH.

The results are shown in Table 4.

TABLE 4

| pH optimum | | | | | | | | | | | | |
|---|---|---|---|---|---|---|---|---|---|---|---|---|
| | pH | | | | | | | | | | | |
| | 2.0 | 3.0 | 3.5 | 4.0 | 4.5 | 5.0 | 6.0 | 7.0 | 8.0 | 9.0 | 10.0 | 11.0 |
| Relative activity (%) | 71.4 | 78.6 | 77.0 | 91.2 | 84.2 | 100.0 | 55.5 | 66.7 | 30.9 | 17.8 | 15.9 | 16.1 |

From the results it can be seen that *Penicillium oxalicum* glucoamylase at the given conditions has the highest activity at pH 5.0. The *Penicillium oxalicum* glucoamylase is active in a broad pH range in the it maintains more than 50% activity from pH 2 to 7.

pH stability. To assess the heat stability of the *Penicillium oxalicum* glucoamylase the Reaction condition assay was modified in that the enzyme solution (50 micro g/mL) was preincubated for 20 hours in buffers with pH 2.0, 3.0, 3.5, 4.0, 4.5, 5.0, 6.0 7.0, 8.0, 9.0, 10.0 and 11.0 using the buffers described under pH optimum. After preincubation, 20 microL soluble starch to a final volume of 100 microL was added to the solution and the assay was performed as described above.

The results are shown in Table 5.

TABLE 5

| pH stability | | | | | | | | | | | | |
|---|---|---|---|---|---|---|---|---|---|---|---|---|
| | pH | | | | | | | | | | | |
| | 2.0 | 3.0 | 3.5 | 4.0 | 4.5 | 5.0 | 6.0 | 7.0 | 8.0 | 9.0 | 10.0 | 11.0 |
| Relative activity (%) | 17.4 | 98.0 | 98.0 | 103.2 | 100.0 | 93.4 | 71.2 | 90.7 | 58.7 | 17.4 | 17.0 | 17.2 |

From the results it can be seen that *Penicillium oxalicum* glucoamylase, is stable from pH 3 to pH 7 after preincubation for 20 hours and it decreases its activity at pH 8.

Example 3

*Penicillium oxalicum* Glucoamylase Variants (PoAMG)—Thermostability Analysis by Differential Scanning Calorimitry (DSC)

Site specific *Penicillium oxalicum* glucoamylase (PoAMG) variants having substitutions and/or deletions at specific positions were constructed basically as described in Example 3 and purified as described in Example 4 in WO2013/053801 (hereby incorporated by reference).

The thermostability of the purified Glucoamylase Po PE001 (SEQ ID NO: 14 with K79V) derived variants were determined at pH 4.0 or 4.8 (50 mM Sodium Acetate) by Differential Scanning calorimetry (DSC) using a VP-Capillary Differential Scanning calorimeter (MicroCal Inc., Piscataway, N.J., USA). The thermal denaturation temperature, Td (° C.), was taken as the top of the denaturation peak (major endothermic peak) in thermograms (Cp vs. T) obtained after heating enzyme solutions in selected buffers (50 mM Sodium Acetate, pH 4.0 or 4.8) at a constant programmed heating rate of 200 K/hr.

Sample- and reference-solutions (approximately 0.3 ml) were loaded into the calorimeter (reference: buffer without enzyme) from storage conditions at 10° C. and thermally pre-equilibrated for 10 minutes at 20° C. prior to DSC scan from 20° C. to 110° C. Denaturation temperatures were determined with an accuracy of approximately +/−1° C.

The isolated variants and the DSC data are disclosed in Table 6 below.

TABLE 6

| Po-AMG name | Mutations (+K79V) | DSC Td (° C.) @ pH 4.0 | DSC Td (° C.) @ pH 4.8 |
|---|---|---|---|
| Glucoamylase Po PE001 SEQ ID NO: 14 with K79V | | 82.1 | 83.4 |
| PE167 | E501V Y504T | 82.1 | |

TABLE 6-continued

| Po-AMG name | Mutations (+K79V) | DSC Td (° C.) @ pH 4.0 | DSC Td (° C.) @ pH 4.8 |
|---|---|---|---|
| PE481 | T65A K161S | 84.1 | 86.0 |
| PE487 | T65A Q405T | 83.2 | |
| PE490 | T65A Q327W | 87.3 | |
| PE491 | T65A Q327F | 87.7 | |
| PE492 | T65A Q327Y | 87.3 | |
| PE493 | P11F T65A Q327F | 87.8 | 88.5 |
| PE497 | R1K D3W K5Q G7V N8S T10K P11S T65A Q327F | 87.8 | 88.0 |
| PE498 | P2N P4S P11F T65A Q327F | 88.3 | 88.4 |
| PE003 | P11F D26C K33C T65A Q327F | 83.3 | 84.0 |
| PE009 | P2N P4S P11F T65A Q327W E501V Y504T | 88.8 | |
| PE002 | R1E D3N P4G G6R G7A N8A T10D P11D T65A Q327F | 87.5 | 88.2 |
| PE005 | P11F T65A Q327W | 87.4 | 88.0 |
| PE008 | P2N P4S P11F T65A Q327F E501V Y504T | 89.4 | 90.2 |
| PE010 | P11F T65A Q327W E501V Y504T | | 89.7 |
| PE507 | T65A Q327F E501V Y504T | | 89.3 |
| PE513 | T65A S105P Q327W | | 87.0 |
| PE514 | T65A S105P Q327F | | 87.4 |
| PE515 | T65A Q327W S364P | | 87.8 |
| PE516 | T65A Q327F S364P | | 88.0 |
| PE517 | T65A S103N Q327F | | 88.9 |
| PE022 | P2N P4S P11F K34Y T65A Q327F | | 89.7 |
| PE023 | P2N P4S P11F T65A Q327F D445N V447S | | 89.9 |
| PE032 | P2N P4S P11F T65A I172V Q327F | | 88.7 |
| PE049 | P2N P4S P11F T65A Q327F N502* | | 88.4 |
| PE055 | P2N P4S P11F T65A Q327F N502T P563S K571E | | 88.0 |
| PE057 | P2N P4S P11F R31S K33V T65A Q327F N564D K571S | | 89.5 |
| PE058 | P2N P4S P11F T65A Q327F S377T | | 88.6 |
| PE064 | P2N P4S P11F T65A V325T Q327W | | 88.0 |
| PE068 | P2N P4S P11F T65A Q327F D445N V447S E501V Y504T | | 90.2 |
| PE069 | P2N P4S P11F T65A I172V Q327F E501V Y504T | | 90.2 |
| PE073 | P2N P4S P11F T65A Q327F S377T E501V Y504T | | 90.1 |
| PE074 | P2N P4S P11F D26N K34Y T65A Q327F | | 89.1 |
| PE076 | P2N P4S P11F T65A Q327F I375A E501V Y504T | | 90.2 |
| PE079 | P2N P4S P11F T65A K218A K221D Q327F E501V Y504T | | 90.9 |
| PE085 | P2N P4S P11F T65A S103N Q327F E501V Y504T | | 91.3 |
| PE086 | P2N P4S P11F T10D T65A Q327F E501V Y504T | | 90.4 |
| PE088 | P2N P4S F12Y T65A Q327F E501V Y504T | | 90.4 |
| PE097 | K5A P11F T65A Q327F E501V Y504T | | 90.0 |
| PE101 | P2N P4S T10E E18N T65A Q327F E501V Y504T | | 89.9 |
| PE102 | P2N T10E E18N T65A Q327F E501V Y504T | | 89.8 |
| PE084 | P2N P4S P11F T65A Q327F E501V Y504T T568N | | 90.5 |
| PE108 | P2N P4S P11F T65A Q327F E501V Y504T K524T G526A | | 88.6 |
| PE126 | P2N P4S P11F K34Y T65A Q327F D445N V447S E501V Y504T | | 91.8 |
| PE129 | P2N P4S P11F R31S K33V T65A Q327F D445N V447S E501V Y504T | | 91.7 |
| PE087 | P2N P4S P11F D26N K34Y T65A Q327F E501V Y504T | | 89.8 |
| PE091 | P2N P4S P11F T65A F80* Q327F E501V Y504T | | 89.9 |
| PE100 | P2N P4S P11F T65A K112S Q327F E501V Y504T | | 89.8 |
| PE107 | P2N P4S P11F T65A Q327F E501V Y504T T516P K524T G526A | | 90.3 |

TABLE 6-continued

| Po-AMG name | Mutations (+K79V) | DSC Td (° C.) @ pH 4.0 | DSC Td (° C.) @ pH 4.8 |
|---|---|---|---|
| PE110 | P2N P4S P11F T65A Q327F E501V N502T Y504* | | 90.6 |

Example 4

Use of High Dosage of Protease Pfu for Oil Extraction and Ethanol

Liquefaction: Nine slurries of whole ground corn, backset and tap water were prepared to a total weight of 150 g targeting 32.50% Dry Solids (DS); backset was blended at 30% weight of backset per weight of slurry. Slurry pH was 5.0 and no further adjustments were made before applying the following treatments:

- 3 mashes were controls, meaning that they only received Alpha-Amylase 369 (AA369) during liquefaction and will be the baseline. AA369 was applied at a fixed dose of 2.1 µg/gDS in all cases when applied.
- 2 mashes were treated with AA369 and 1.5 µg/gDS Protease Pfu.
- 2 mashes were treated with AA369 and 3 µg/gDS Protease Pfu.
- 2 mashes were treated with AA369 and 5 µg/gDS Protease Pfu.

Water and enzymes were added to each canister, and then each canister was sealed and mixed well prior to loading into the Labomat. All samples were incubated in the Labomat set to the following conditions: 5° C./min. Ramp, 15 minute Ramp to 80° C., hold for 1 min, Ramp to 85° C. at 1° C./min and holding for 103 min., 40 rpm for 30 seconds to the left and 30 seconds to the right. Once liquefaction was complete, all canisters were cooled in an ice bath for approximately 20 minutes before proceeding to fermentation.

Simultaneous Saccharification and Fermentation (SSF): Penicillin was added to each mash to a final concentration of 3 ppm and adjusted to pH 5.0 with either 40% sulfuric acid or 45% potassium hydroxide as needed. Next, a portion of this mash was transferred to test tubes and represents "urea-free" fermentations, or ones which are considered to be nitrogen limited. Once the "urea-free" mashes were processed, the remaining mashes were dosed with urea up to a final concentration of 200 ppm and transferred to test tubes for fermentation. All test tubes were drilled with a 1/64" bit to allow $CO_2$ release. Furthermore, equivalent solids were maintained across all treatments through the addition of water as required to ensure that the urea versus urea-free mashes contained equal solids. Fermentation was initiated through the addition of Glucoamylase A (0.60 AGU/gDS), water and rehydrated yeast. Yeast rehydration took place by mixing 5.5 g of Fermentis' ETHANOL RED™ into 100 mL of 32° C. tap water for at least 15 minutes and dosing 100 µl per test tube.

Distillation: A Büchi Multivapor evaporation system was used for all distillations. The unit distilled 12 samples at a time. The parameters used are shown in Table 7. Tubes were weighed after distillation and weight lost during distillation was replaced with DI water. Tubes were weighed again after water addition. Three separate distillations were performed for this experiment which included a control each run.

TABLE 7

| Distillation parameters for corn oil assay. | |
|---|---|
| Time | 80 min |
| Temperature | 75° C. |
| Vacuum | 200-153 mBar (40 min) |
| | 153-148 mBar (40 min) |
| RPM | 8 |

Oil Extraction: Hexane was added to each sample at a dose of 0.125 mL hexane/1 g starting material. Each tube was covered in Dura-seal to prevent sample leakage, and mixed thoroughly. Tubes were centrifuged at 3,000×g for 10 minutes in an Avanti JE Series centrifuge with JS-5.3 rotor. After centrifugation, the oil/hexane layer (supernatant) was removed using a positive displacement pipette, transferred to a pre-weighed 5 mL flip-top tube, and reweighed. The density of the sample was measured using a Rudolph Research Analytical density meter. The density of the supernatant was then calculated using the standard curve equation to find the % oil in the supernatant. From this value the total % oil in the starting material was derived.

HPLC analysis: HPLC analysis used an Agilent 1100/1200 combined with a Bio-Rad HPX-87H Ion Exclusion column (300 mm×7.8 mm) and a Bio-Rad Cation H guard cartridge. The mobile phase was 0.005 M sulfuric acid and processed samples at a flow rate of 0.6 ml/min, with column and RI detector temperatures of 65 and 55° C., respectively. Fermentation sampling took place after 54 hours by sacrificing 3 tubes per treatment. Each tube was processed by deactivation with 50 µL of 40% v/v $H_2SO_4$, vortexing, centrifuging at 1460×g for 10 minutes, and filtering through a 0.45 µm Whatman PP filter. Samples were stored at 4° C. prior to and during HPLC analysis. The method quantified analytes using calibration standards for DP4+, DP3, DP2, glucose, fructose, acetic acid, lactic acid, glycerol and ethanol (% w/v). A four point calibration including the origin is used for quantification.

Figure 2:
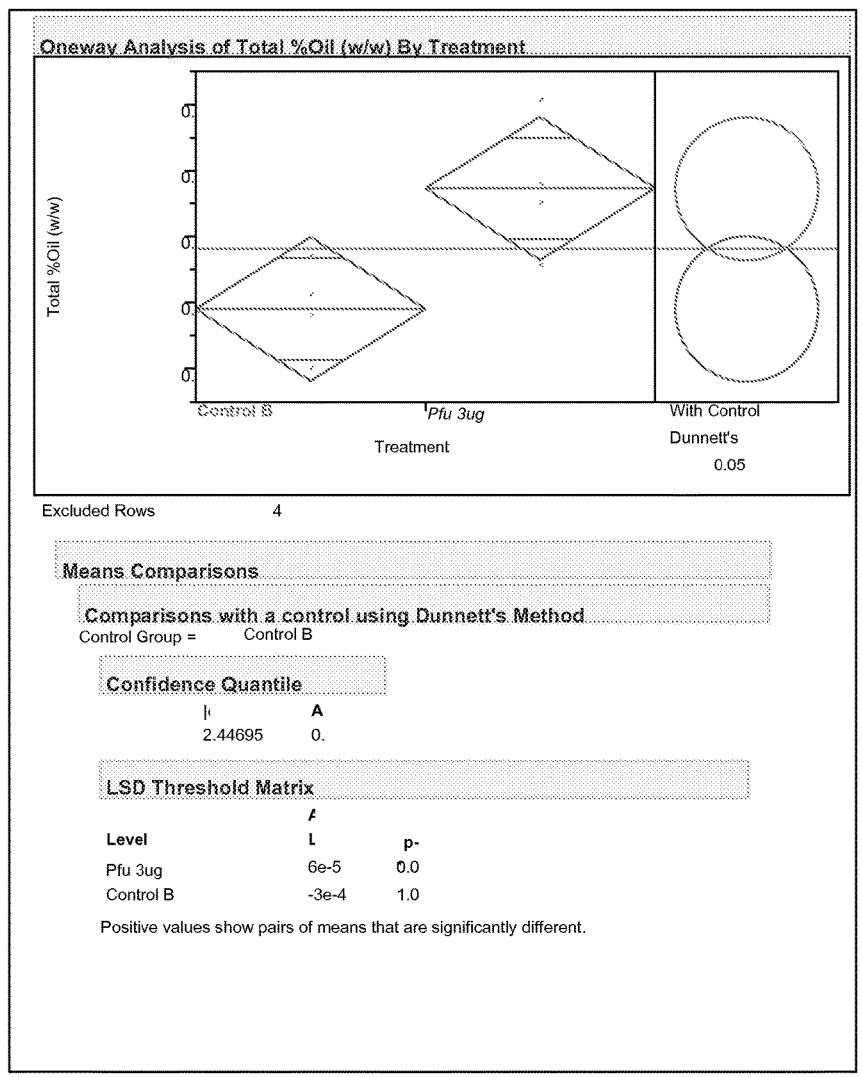
FIG. 2 shows an oil extraction comparison between Protease Pfu (3 μg/gDS) and Protease X (statistical difference).
Figure 3:
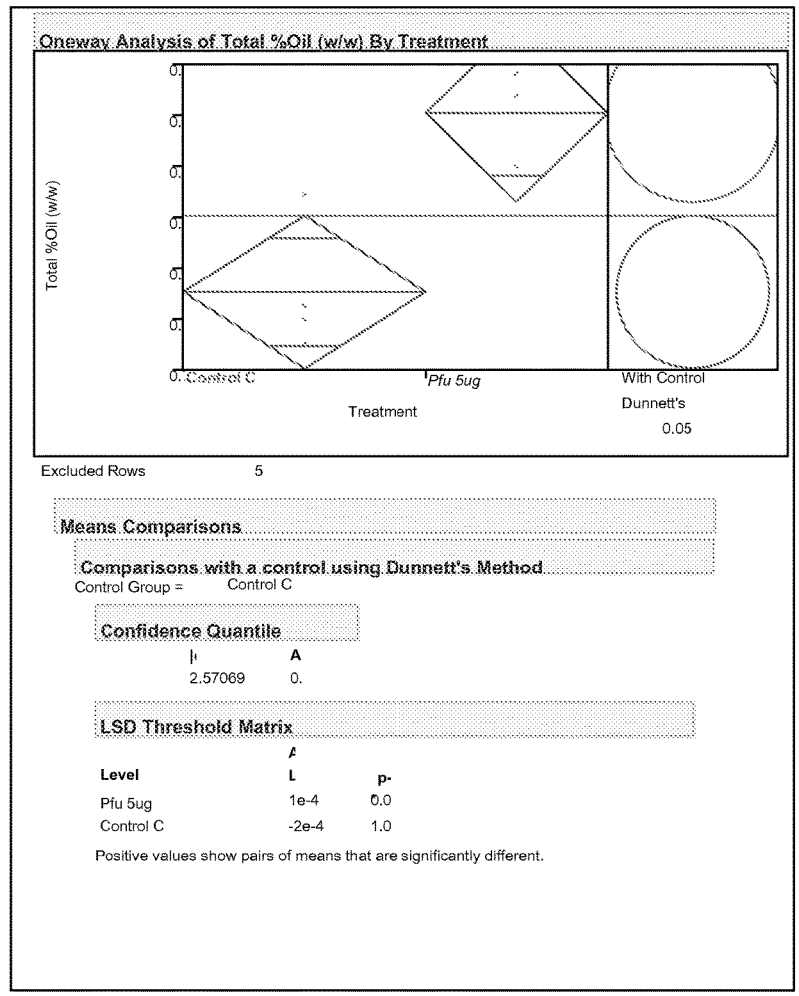
FIG. 3 shows an oil extraction comparison between Protease Pfu (5 μg/gDS) and Protease X (statistical difference).

Results (corn oil extraction): Terminology used in the example: For corn oil extraction, there are three separate controls (Control A, B and C) because each distillation processed a control for each run. However, each control was processed the same during liquefaction and fermentation: no protease during fermentation with Protease X addition to fermentation. Extraction of corn oil showed that the lowest dose of Protease Pfu added to liquefaction matched the dose of Protease X (0.025% w/w) to fermentation (FIG. 1). Moreover, increasing Protease Pfu to 3 and 5 µg/gDS surpassed the oil recovered with Protease X alone, and there was no additional benefit from combining both Protease Pfu and Protease X at this dose, suggesting little to no synergy between these two proteases (FIGS. 2 & 3).

Ethanol: Performance of Various Proteases on Limited Dosage of Exogenous Nitrogen Addition The performance of various proteases using limiting dosage of exogenous nitrogen was also tested. It is investigates how the substrates produced from these proteases affect fermentation rate, carbohydrate consumption and glycerol formation.

Figure 4:
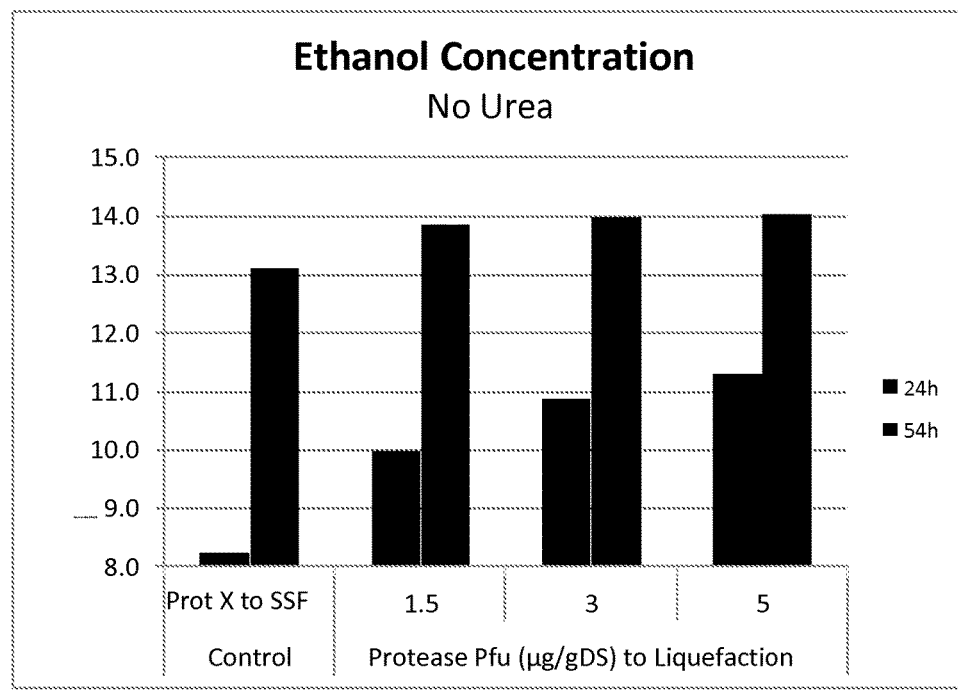
FIG. 4 shows the ethanol concentrations (% w/v) for no-urea fermentations.
Figure 5:
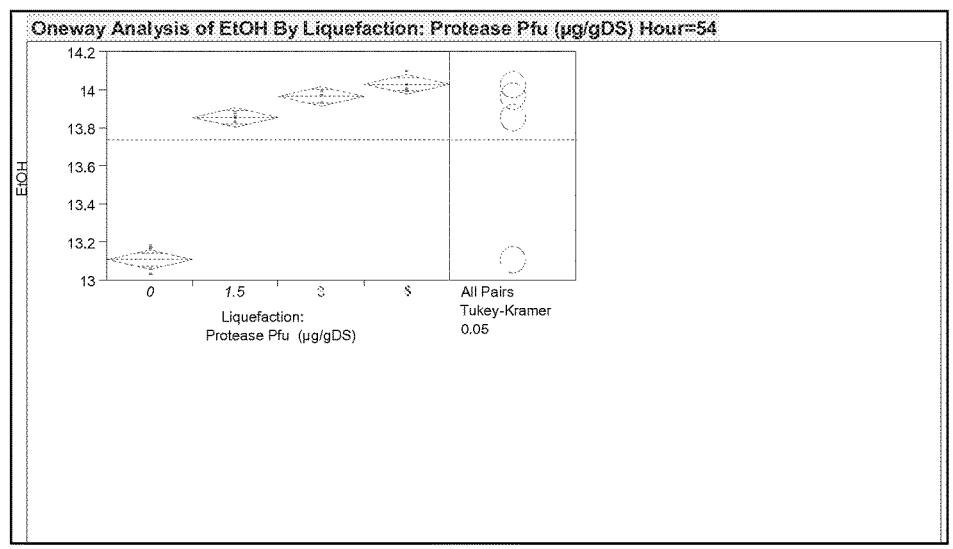
FIG. 5 shows an Oneway Analysis of the ethanol concentration (% w/v) comparison for 0, 1.5, 3 and 5 μg/gDS Protease Pfu comparison urea-free fermentations.

Treating fermentation with Protease X and operating without supplemental nitrogen from urea did not lead to dryness, whereas delivered dryness by the 54 hour mark at all dosages (FIG. 4). Furthermore, increasing Protease Pfu to 3 or 5 µg/gDS from 1.5 µg/gDS led to a significant increase in final ethanol concentration (% w/v) (FIGS. 4 & 5). These various protease treatments also demonstrate an effect on fermentation rate as the 24 hour ethanol concentrations are highest with the highest treatment of Protease Pfu.

Figure 6:
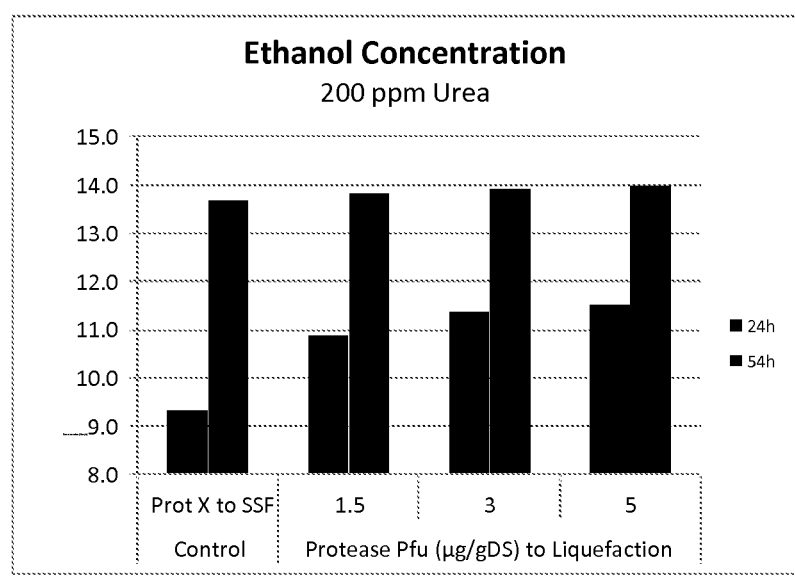
FIG. 6 shows the ethanol concentrations (% w/v) for fermentations operating with 200 ppm urea for Protease X added in SSF and Protease Pfu (1.5, 3 and 5 μg/gDS.
Figure 7:
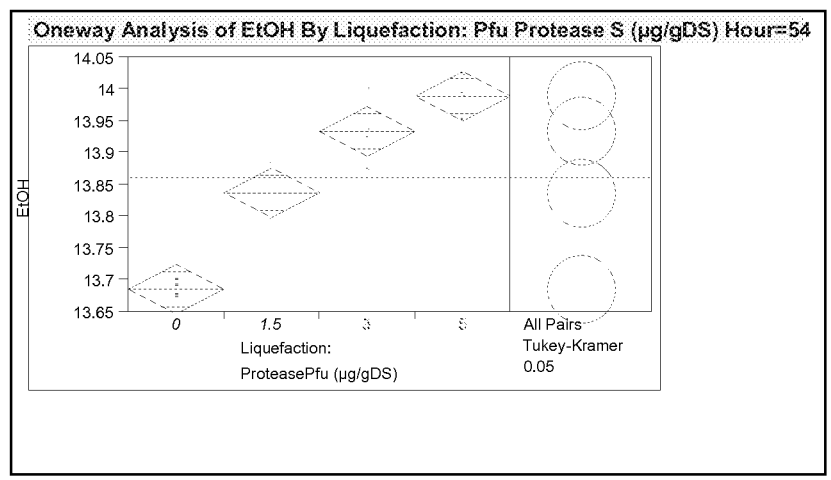
FIG. 7 shows an Oneway Analysis of the ethanol concentration (% w/v) comparison for 0, 1.5, 3 and 5 μg/gDS Protease Pfu for 200 ppm urea based fermentations.
Figure 8:
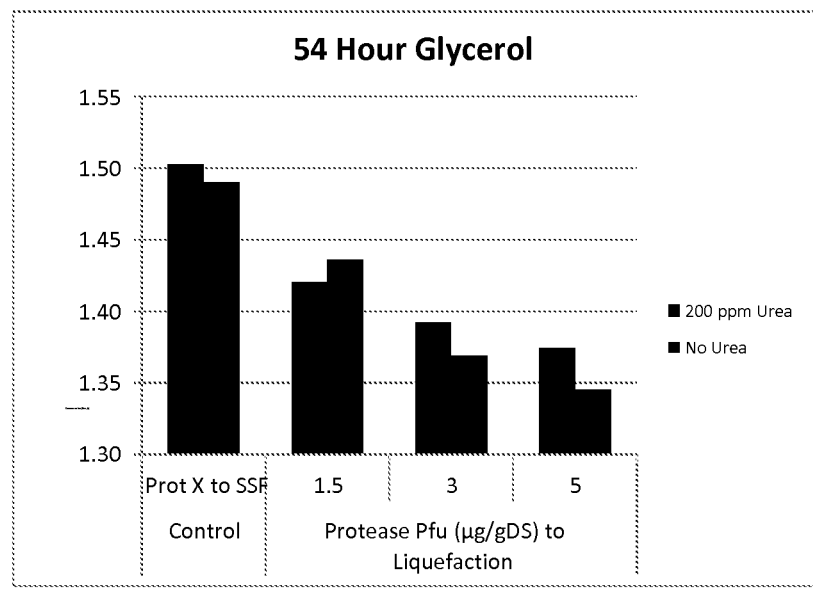
FIG. 8 shows the 54 hour glycerol concentrations (% w/v). The highest dose of Protease Pfu (5 μg/gDS) was approximately 10% lower than the control of Protease X.

Similar trends were observed when incorporating 200 ppm urea into fermentation, but Protease Pfu activity during liquefaction remained superior relative to Protease X by delivering the lowest residual glucose and yielding the highest final ethanol. Here, the lowest dose of Protease Pfu (1.5 µg/gDS) outperformed Protease X by supporting a faster fermentation through the first 24 hours, combined with statistically higher final ethanol concentrations (% w/v) (FIGS. 6 & 7). In general, more Protease Pfu led to more ethanol production by the 54 hour mark, though the two highest doses were statistically equivalent in this example. All fermentations reached a state of dryness by the 54 hour mark. Higher doses of Protease Pfu also reduced the formation of glycerol during fermentation, and this shift in metabolism is part of the reason why the increase in ethanol is being observed (FIG. 8—% w/v).

Conclusions

Oil Extraction:
- 1.5 µg/gDS of Protease Pfu action during a conventional corn based liquefaction (85° C., pH 5.0, 2 hours) working in combination with 2.1 µg EP/gDS Alpha-Amylase 369 matched the increase in oil extracted from fermentation treatment with Protease X (5 µg/gDS).
- An even higher Protease Pfu dose of 3 µg/gDS led to approximately 5% more oil versus Protease X alone and similar results were seen with 5 µg/gDS dose as well.
- There was no apparent synergy in oil recovery when combining Protease Pfu with Protease X, and there seems to be no improvement in running protease during liquefaction versus fermentation.

Ethanol Yield: Protease Pfu showed superior performance over Protease X

No Urea:
- 24 hour data showed Protease Pfu (1.5 µg/gDS) delivered a much more efficient fermentation than Protease X by having lower residual glucose and higher ethanol concentrations, where increasing to 3 or 5 µg/gDS led to even more ethanol production.
- 54 hour data showed Protease Pfu (1.5 µg/gDS) outperformed Protease X by delivering low residual glucose and much higher ethanol concentrations. Fermentations reached dryness with all dosages of Protease Pfu, whereas Protease X finished with just over 1% w/v.
- Glycerol concentrations were 10% lower than Protease X with Protease Pfu (5 µg/gDS).

200 ppm Urea:
- 24 hour data showed that Protease Pfu (1.5 µg/gDS) outperformed Protease X by having lower residual glucose and higher ethanol concentrations with 200 ppm urea. In general, more Protease Pfu led to more ethanol by this time point, though the two highest doses (3 and 5 µg/gDS) were very similar.
- 54 hour HPLC showed that Protease Pfu (1.5 µg/gDS) outperformed Protease X by delivering the lowest residual glucose while yielding the highest final ethanol. All fermentations reached dryness. Even the lowest dose of Protease Pfu (1.5 µg/gDS) yielded 1% more ethanol than Protease X. While 3 and 5 µg/gDS Protease Pfu were statistically equivalent in final ethanol, they were both higher than the lowest Protease Pfu dose.
- Glycerol concentrations were approximately 9% lower than Protease X with Protease Pfu (5 µg/gDS). Protease Pfu delivered the best final ethanol concentrations while also delivering the lowest final glycerol concentrations.

Example 5

Use of High Protease Pfu Dose in Liquefaction in Ethanol Production Process

Liquefaction: Thirteen slurries of whole ground corn and tap water were prepared to a total weight of 125 g targeting 32.50% Dry Solids (DS); backset was blended at 30% weight of backset per weight of slurry. Initial slurry pH was approximately 6.0 and was adjusted to 5.0 with either 45% w/v potassium hydroxide or 40% v/v sulfuric acid. A fixed dose of Alpha-Amylase 1407 (1.73 µg EP/gDS) was applied to all slurries and was combined with Protease Pfu as follows to evaluate the effect of high protease treatment during liquefaction:

Control: Alpha-amylase Only
Alpha-amylase 1407+0.0355 µg/gDS Protease Pfu
Alpha-amylase 1407+0.25 µg/gDS Protease Pfu
Alpha-amylase 1047+0.5 µg/gDS Protease Pfu
Alpha-amylase 1407+1 µg/gDS Protease Pfu
Alpha-amylase 1407+10 µg/gDS Protease Pfu
Alpha-amylase 1407+50 µg/gDS Protease Pfu Water and enzymes were added to each canister, and then each canister was sealed and mixed well prior to loading into the Labomat. All samples were incubated in the Labomat set to the following conditions: 5° C./min. Ramp, 15 minute Ramp to 80° C., hold for 1 min, Ramp to 85° C. at 1° C./min and holding for 103 min., 40 rpm for 30 seconds to the left and 30 seconds to the right. Once liquefaction was complete, all canisters were cooled in an ice bath for approximately 20 minutes before proceeding to fermentation.

Simultaneous Saccharification and Fermentation (SSF): Penicillin was added to each mash to a final concentration of 3 ppm and pH was adjusted to 5.0. Next, portions of this mash were transferred to test tubes to represent "urea-free" fermentations and are considered nitrogen limited. Once the "urea-free" mashes were processed, the remaining mashes were dosed with urea up to a final concentration of 800 ppm and also transferred to test tubes. All test tubes were drilled with a 1/64" bit to allow $CO_2$ release. Furthermore, equivalent solids were maintained across all treatments through the addition of water as required to ensure that the urea versus urea-free mashes contained equal solids. Fermentation was initiated through the addition of Glucoamylase U (0.50 AGU/gDS), water and rehydrated yeast. Yeast rehydration took place by mixing 5.5 g of ETHANOL RED™ into 100 mL of 32° C. tap water for at least 15 minutes and dosing 100 µl per test tube.

HPLC analysis: HPLC analysis used an Agilent 1100/1200 combined with a Bio-Rad HPX-87H Ion Exclusion column (300 mm×7.8 mm) and a Bio-Rad Cation H guard cartridge. The mobile phase was 0.005 M sulfuric acid and processed samples at a flow rate of 0.6 ml/min, with column and RI detector temperatures of 65 and 55° C., respectively. Fermentation sampling took place after 54 hours by sacrificing 3 tubes per treatment. Each tube was processed by deactivation with 50 μL of 40% v/v $H_2SO_4$, vortexing, centrifuging at 1460×g for 10 minutes, and filtering through a 0.45 μm Whatman PP filter. Samples were stored at 4° C. prior to and during HPLC analysis. The method quantified analytes using calibration standards for DP4+, DP3, DP2, glucose, fructose, acetic acid, lactic acid, glycerol and ethanol (% w/v). A four point calibration including the origin is used for quantification.

Figure 9:
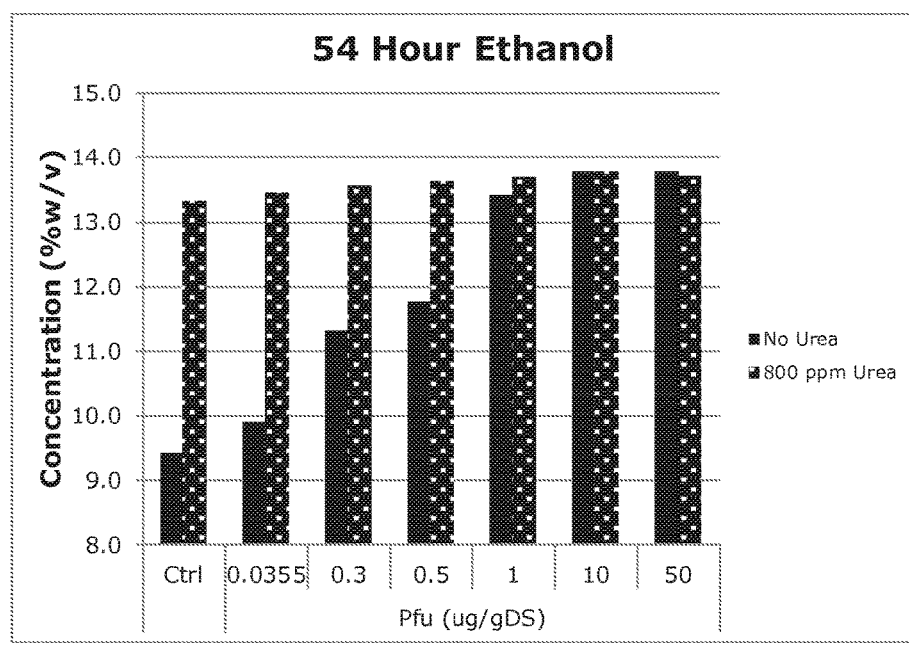
FIG. 9 shows the ethanol concentrations (% w/v) after 54 hours when from 0 (control) to 50 μg/gDS Protease Pfu was added in liquefaction.
Figure 10:
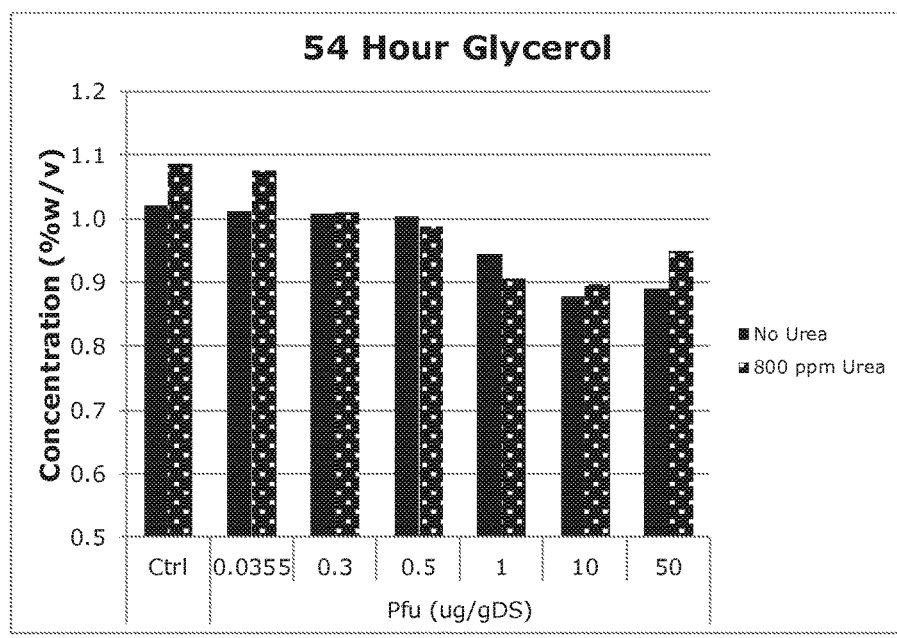
FIG. 10 shows the glycerol concentrations (% w/v) after 54 hours when from 0 (control) to 50 μg/gDS Protease Pfu was added in liquefaction.
Figure 11:
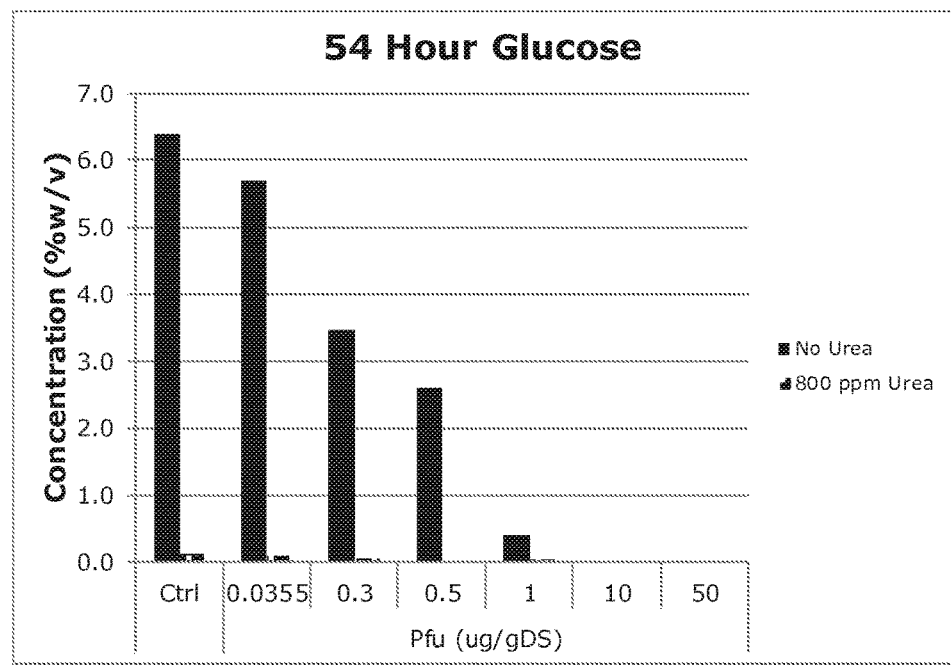
FIG. 11 shows the glucose concentrations (% w/v) after 54 hours when from 0 (control) to 50 μg/gDS Protease Pfu was added in liquefaction.

Conclusions: Comparison of 54 hour ethanol concentrations showed that more than 1 μg/gDS Protease Pfu was required to support fermentation to dryness under nitrogen limited conditions (FIGS. 9 & 10). Moreover, residual glucose was 0.4% w/v for the 1 μg/gDS dose, whereas no residual glucose was observed at Protease Pfu dosages of 10 or 50 μg/gDS. The most significant reduction in glycerol was observed at the two highest dosages of Protease Pfu, 10 and 50 μg/gDS. These results suggest that as much as 10 to 50 μg/gDS Protease Pfu may be required during liquefaction to achieve optimal performance as it relates to liquefaction and fermentation.

Summary Paragraphs

The present invention is defined in the claims and accompanying description. For convenience, other aspects of the present invention are presented herein by way of numbered paragraphs:

1. A process of recovering oil from a fermentation product production process comprising the steps of:
    a) liquefying starch-containing material at a temperature above the initial gelatinization temperature using:
        an alpha-amylase;
        more than 0.5 micro gram *Pyrococcus furiosus* protease per gram dry solids (DS);
    b) saccharifying using a glucoamylase;
    c) fermenting using a fermenting organism.
    d) recovering the fermentation product to form whole stillage;
    e) separating the whole stillage into thin stillage and wet cake;
    f) optionally concentrating the thin stillage into syrup;
    wherein oil is recovered from the:
        liquefied starch-containing material after step a); and/or
        downstream from fermentation step c).
2. The process of paragraph 1, wherein oil is recovered during and/or after liquefying the starch-containing material.
3. The process of paragraph 1, wherein oil is recovered from the whole stillage.
4. The process of any of paragraphs 1-3, wherein oil is recovered from the thin stillage.
5. The process of any of paragraphs 1-4, wherein oil is recovered from the syrup.
6. The process of any of paragraph 1-5, wherein 0.5-100 micro gram *Pyrococcus furiosus* protease per gram DS, such as 1-50 micro gram *Pyrococcus furiosus* protease per gram DS, such as 1-10 micro gram *Pyrococcus furiosus* protease per gram DS, such as 1.5-5 micro gram *Pyrococcus furiosus* protease per gram DS, such as around or more than 1.5 micro gram *Pyrococcus furiosus* protease per gram DS are present and/or added in liquefaction step a).
7. The process of any of paragraphs 1-6 wherein 2-100 micro gram *Pyrococcus furiosus* protease per gram DS, such as 2.5-50 micro gram *Pyrococcus furiosus* protease per gram DS, such as 2.5-10 micro gram *Pyrococcus furiosus* protease per gram DS, such as 2.5-5 micro gram *Pyrococcus furiosus* protease gram DS, especially around 3 micro gram *Pyrococcus furiosus* protease per gram DS are present and/or added in liquefaction step a).
8. The process of any of paragraphs 1-7, wherein the *Pyrococcus furiosus* protease is the mature sequence shown in SEQ ID NO: 13 herein.
9. The process of any of paragraphs 1-8, wherein the *Pyrococcus furiosus* protease is one having at least 80%, such as at least 85%, such as at least 90%, such as at least 95%, such as at least 96%, such as at least 97%, such as at least 98%, such as at least 99% identity to SEQ ID NO: 13 herein.
10. The process of any of paragraph 1-9, wherein no nitrogen-compound is present and/or added in steps a)-c), such as during saccharification step b), fermentation step c), or simultaneous saccharification and fermentation (SSF).
11. The process of any of paragraph 1-10, wherein 10-1,000 ppm, such as 50-800 ppm, such as 100-600 ppm, such as 200-500 ppm nitrogen-compound, preferably urea, is present and/or added in steps a)-c), such as in saccharification step b) or fermentation step c) or in simultaneous saccharification and fermentation (SSF).
12. The process of any of paragraphs 1-11, wherein the alpha-amylase is from the genus *Bacillus*, such as a strain of *Bacillus stearothermophilus*, such as the sequence shown in SEQ ID NO: 1.
13. The process of any of paragraphs 1-12, wherein the alpha-amylase a *Bacillus stearothermophilus* alpha-amylase shown in SEQ ID NO: 1 herein, such as one having at least 80%, such as at least 85%, such as at least 90%, such as at least 95%, such as at least 96%, such as at least 97%, such as at least 98%, such as at least 99% identity to SEQ ID NO: 1 herein.
14. The process of paragraph 11, wherein the *Bacillus stearothermophilus* alpha-amylase or variant thereof is truncated, preferably to have around 491 amino acids, such as from 480-495 amino acids.
15. The process of any of paragraphs 12-14, wherein the *Bacillus stearothermophilus* alpha-amylase has a double deletion at positions I181+G182, and optionally a N193F substitution (using SEQ ID NO: 1 for numbering),
16. The process of any of paragraphs 12-14, wherein the *Bacillus stearothermophilus* alpha-amylase has a double deletion at positions R179+G180 and optionally a N193F substitution (using SEQ ID NO: 1 for numbering).
17. The process of any of paragraphs 12-16, wherein the *Bacillus stearothermophilus* alpha-amylase has a substitution at position S242, preferably S242Q substitution.
18. The process of any of paragraphs 12-17, wherein the *Bacillus stearothermophilus* alpha-amylase has a substitution at position E188, preferably E188P substitution.
19. The process of any of paragraphs 1-18, wherein the alpha-amylase has a T½ (min) at pH 4.5, 85° C., 0.12 mM $CaCl_2$) of at least 10.
20. The process of any of paragraphs 1-19, wherein the alpha-amylase has a T½ (min) at pH 4.5, 85° C., 0.12 mM $CaCl_2$) of at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.
21. The process of any of paragraphs 1-20, wherein the alpha-amylase is selected from the group of *Bacillus stearothermophilus* alpha-amylase variants with the following mutations in addition to I181*+G182*, and optionally N193F:

V59A + Q89R + G112D + E129V + K177L + R179E + K220P + N224L + Q254S;
V59A + Q89R + E129V + K177L + R179E + H208Y + K220P + N224L + Q254S;
V59A + Q89R + E129V + K177L + R179E + K220P + N224L + Q254S + D269E + D281N;
V59A + Q89R + E129V + K177L + R179E + K220P + N224L + Q254S + I270L;
V59A + Q89R + E129V + K177L + R179E + K220P + N224L + Q254S + H274K;
V59A + Q89R + E129V + K177L + R179E + K220P + N224L + Q254S + Y276F;
V59A + E129V + R157Y + K177L + R179E + K220P + N224L + S242Q + Q254S;
V59A + E129V + K177L + R179E + H208Y + K220P + N224L + S242Q + Q254S;
59A + E129V + K177L + R179E + K220P + N224L + S242Q + Q254S;
V59A + E129V + K177L + R179E + K220P + N224L + S242Q + Q254S + H274K;
V59A + E129V + K177L + R179E + K220P + N224L + S242Q + Q254S + Y276F;
V59A + E129V + K177L + R179E + K220P + N224L + S242Q + Q254S + D281N;
V59A + E129V + K177L + R179E + K220P + N224L + S242Q + Q254S + M284T;
V59A + E129V + K177L + R179E + K220P + N224L + S242Q + Q254S + G416V;
V59A + E129V + K177L + R179E + K220P + N224L + Q254S;
V59A + E129V + K177L + R179E + K220P + N224L + Q254S + M284T;
A91L + M96I + E129V + K177L + R179E + K220P + N224L + S242Q + Q254S;
E129V + K177L + R179E;
E129V + K177L + R179E + K220P + N224L + S242Q + Q254S;
E129V + K177L + R179E + K220P + N224L + S242Q + Q254S + Y276F + L427M;
E129V + K177L + R179E + K220P + N224L + S242Q + Q254S + M284T;
E129V + K177L + R179E + K220P + N224L + S242Q + Q254S + N376* + I377*;
E129V + K177L + R179E + K220P + N224L + Q254S;
E129V + K177L + R179E + K220P + N224L + Q254S + M284T;
E129V + K177L + R179E + S242Q;
E129V + K177L + R179V + K220P + N224L + S242Q + Q254S;
K220P + N224L + S242Q + Q254S;
M284V;
V59A Q89R + E129V + K177L + R179E + Q254S + M284V.

22. The process of any of paragraphs 1-21, wherein the alpha-amylase is selected from the group of *Bacillus stearothermophilus* alpha-amylase variants:
I181*+G182*+N193F+E129V+K177L+R179E;
I181*+G182*+N193F+V59A+Q89R+E129V+K177L+R179E+H208Y+K220P+N224L+Q254S
I181*+G182*+N193F+V59A Q89R+E129V+K177L+R179E+Q254S+M284V; and
I181*+G182*+N193F+E129V+K177L+R179E+K220P+N224L+S242Q+Q254S (using SEQ ID NO: 1 for numbering).

23. The process of any of paragraphs 1-22, wherein the alpha-amylase variant has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 1 herein.

24. The process of any of paragraphs 1-23, wherein the alpha-amylase is a *Bacillus licheniformis* alpha-amylase, or a variant thereof.

25. The process of paragraph 24, wherein the *Bacillus licheniformis* alpha-amylase is the one shown in SEQ ID NO: 21 herein.

26. The process of any of paragraphs 1-25, wherein the alpha-amylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% identity to the mature part of the polypeptide of SEQ ID NO: 21 herein.

27. The process of any of paragraphs 1-26, wherein the alpha-amylase is present and/or added in a concentration of 0.1-100 micro gram per gram DS, such as 0.5-50 micro gram per gram DS, such as 1-25 micro gram per gram DS, such as 1-10 micro gram per gram DS, such as 2-5 micro gram per gram DS.

28. The process of any of paragraphs 1-27, wherein from 1-10 micro gram *Pyrococcus furiosus* protease and 1-10 micro gram *Bacillus stearothermophilus* alpha-amylase are present and/or added in liquefaction.

29. The process of any of paragraphs 1-28, wherein a glucoamylase is present and/or added in liquefaction step a).

30. The process of paragraph 29, wherein the glucoamylase present and/or added in liquefaction has a heat stability at 85° C., pH 5.3, of at least 20%, such as at least 30%, preferably at least 35%.

31. The process of paragraph 29 or 30, wherein the glucoamylase has a relative activity pH optimum at pH 5.0 of at least 90%, preferably at least 95%, preferably at least 97%.

32. The process of any of paragraphs 29-30, wherein the glucoamylase has a pH stability at pH 5.0 of at least at least 80%, at least 85%, at least 90%.

33. The process of any of paragraphs 29-32, wherein the glucoamylase present and/or added in liquefaction step a) is derived from a strain of the genus *Penicillium*, especially a strain of *Penicillium oxalicum* disclosed as SEQ ID NO: 2 in WO 2011/127802 or SEQ ID NOs: 9 or 14 herein.

34. The process of paragraph 29-33, wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 9 or 14 herein.

35. The process of any of paragraphs 29-34, wherein the glucoamylase is a variant of the *Penicillium oxalicum* glucoamylase shown in SEQ ID NO: 2 in WO 2011/127802 having a K79V substitution (using the mature sequence shown in SEQ ID NO: 14 for numbering), such as a variant disclosed in WO 2013/053801.

36. The process of any of paragraph 29-35, wherein the *Penicillium oxalicum* glucoamylase has a K79V substitution (using SEQ ID NO: 14 for numbering) and further one of the following:
T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+I172V+Q327F+E501V+Y504T; or
P2N+P4S+P11F+T65A+Q327F+S377T+E501V+Y504T; or
P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or
P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or
P2N+P4S+P11F+T65A+Q327F+E501V+Y504T+T568N; or
P2N+P4S+P11F+T65A+Q327F+E501V+Y504T+K524T+G526A; or
P2N+P4S+P11F+K34Y+T65A+Q327F+D445N+V447S+E501V+Y504T; or
P2N+P4S+P11F+R31 S+K33V+T65A+Q327F+D445N+V447S+E501V+Y504T; or
P2N+P4S+P11F+D26N+K34Y+T65A+Q327F+E501V+Y504T; or
P2N+P4S+P11F+T65A+F80*+Q327F+E501V+Y504T; or
P2N+P4S+P11F+T65A+K112S+Q327F+E501V+Y504T; or
P2N+P4S+P11F+T65A+Q327F+E501V+Y504T+T516P+K524T+G526A; or
P2N+P4S+P11F+T65A+Q327F+E501V+N502T+Y504*; or
P2N+P4S+P11F+T65A+Q327F+E501V+Y504T; or
P2N+P4S+P11F+T65A+S103N+Q327F+E501V+Y504T; or
K5A+P11F+T65A+Q327F+E501V+Y504T; or
P2N+P4S+P11F+T65A+Q327F+E501V+Y504T+T516P+K524T+G526A; or
P2N+P4S+P11F+T65A+K79A+Q327F+E501V+Y504T; or
P2N+P4S+P11F+T65A+K79G+Q327F+E501V+Y504T; or
P2N+P4S+P11F+T65A+K79I+Q327F+E501V+Y504T; or
P2N+P4S+P11F+T65A+K79L+Q327F+E501V+Y504T; or
P2N+P4S+P11F+T65A+K79S+Q327F+E501V+Y504T; or
P2N+P4S+P11F+T65A+L72V+Q327F+E501V+Y504T; or
S255N+Q327F+E501V+Y504T; or
P2N+P4S+P11F+T65A+E74N+V79K+Q327F+E501V+Y504T; or
P2N+P4S+P11F+T65A+G220N+Q327F+E501V+Y504T; or
P2N+P4S+P11F+T65A+Y245N+Q327F+E501V+Y504T; or
P2N+P4S+P11F+T65A+Q253N+Q327F+E501V+Y504T; or
P2N+P4S+P11F+T65A+D279N+Q327F+E501V+Y504T; or
P2N+P4S+P11F+T65A+Q327F+S359N+E501V+Y504T; or
P2N+P4S+P11F+T65A+Q327F+D370N+E501V+Y504T; or
P2N+P4S+P11F+T65A+Q327F+V460S+E501V+Y504T; or
P2N+P4S+P11F+T65A+Q327F+V460T+P468T+E501V+Y504T; or
P2N+P4S+P11F+T65A+Q327F+T463N+E501V+Y504T; or
P2N+P4S+P11F+T65A+Q327F+S465N+E501V+Y504T; or
P2N+P4S+P11F+T65A+Q327F+T477N+E501V+Y504T.
37. The process of any of paragraphs 29-36, wherein the glucoamylase present and/or added in liquefaction is the *Penicillium oxalicum* glucoamylase having a K79V substitution (using SEQ ID NO: 14 for numbering) and further one of the following:
P11F+T65A+Q327F;
P2N+P4S+P11F+T65A+Q327F (using SEQ ID NO: 14 for numbering).
38. The process of any of paragraphs 11-27, wherein the glucoamylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 14 herein.
39. The process of any of paragraphs 1-38, further wherein a glucoamylase is present and/or added in saccharification and/or fermentation.
40. The process of paragraph 39, wherein the glucoamylase present and/or added in saccharification and/or fermentation is of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii*, or a strain of *Pycnoporus*, or a strain of *Gloephyllum*, such as *G. serpiarium* or *G. trabeum*, or a strain of the *Nigrofomes*.
41. The process of any of paragraphs 39-40, wherein the glucoamylase is derived from *Talaromyces emersonii*, such as the one shown in SEQ ID NO: 19 herein,
42. The process of any of paragraphs 39-41, wherein the glucoamylase is selected from the group consisting of:
(i) a glucoamylase comprising the mature polypeptide of SEQ ID NO: 19 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 19 herein.
43. The process of any of paragraphs 39-42, wherein the glucoamylase is derived from *Gloephyllum serpiarium*, such as the one shown in SEQ ID NO: 15 herein.
44. The process of any of paragraphs 39-43, wherein the glucoamylase is selected from the group consisting of:
(i) a glucoamylase comprising the mature polypeptide of SEQ ID NO: 15 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 15 herein.
45. The process of any of paragraphs 39-44, wherein the glucoamylase is derived from *Gloeophyllum trabeum* such as the one shown in SEQ ID NO: 17 herein.
46. The process of any of paragraphs 39-45, wherein the glucoamylase is selected from the group consisting of:
(i) a glucoamylase comprising the mature polypeptide of SEQ ID NO: 17 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 17 herein.
47. The process of any of paragraphs 39-46, wherein the glucoamylase is present and/or added in saccharification and/or fermentation in combination with an alpha-amylase.
48. The process of paragraph 47, wherein the alpha-amylase present and/or added in saccharification and/or fermentation is of fungal or bacterial origin.
49. The process of paragraph 47 or 48, wherein the alpha-amylase present and/or added in saccharification and/or fermentation is derived from a strain of the genus *Rhizomucor*, preferably a strain the *Rhizomucor pusillus*, such as the one shown in SEQ ID NO: 3 in WO 2013/006756, such as a *Rhizomucor pusillus* alpha-amylase hybrid having an *Aspergillus niger* linker and starch-bonding domain, such as the one shown in SEQ ID NO: 16 herein, or a variant thereof.
50. The process of any of paragraphs 47-49, wherein the alpha-amylase present and/or added in saccharification and/or fermentation is selected from the group consisting of:
(i) an alpha-amylase comprising the mature polypeptide of SEQ ID NO: 16 herein;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 16 herein.
51. The process of any of paragraphs 47-50, wherein the alpha-amylase is a variant of the alpha-amylase shown in SEQ ID NO: 13 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 16 for numbering).
52. The process of any of paragraphs 47-51, wherein the alpha-amylase is derived from a *Rhizomucor pusillus* with an *Aspergillus niger* glucoamylase linker and starch-binding domain (SBD), preferably disclosed as SEQ ID NO: 13 herein, preferably having one or more of the following substitutions: G128D, D143N, preferably G128D+D143N (using SEQ ID NO: 13 for numbering).
53. The process of amylase of paragraphs 47-52, wherein the alpha-amylase variant present and/or added in saccharification and/or fermentation has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 16 herein.
54. The process of any of paragraphs 1-53, further wherein a pullulanase is present and/or added in liquefaction and/or saccharification and/or fermentation.

55. The process of paragraph 54, wherein the pullulanase is a family GH57 pullulanase, wherein the pullulanase preferably includes an X47 domain as disclosed in WO 2011/087836.
56. The process of paragraphs 54-55, wherein the pullulanase is derived from a strain from the genus *Thermococcus*, including *Thermococcus litoralis* and *Thermococcus hydrothermalis* or a hybrid thereof.
57. The process of any of paragraphs 54-56, wherein the pullulanase is the truncated *Thermococcus hydrothermalis* pullulanase at site X4 or a *T. hydrothermalis/T. litoralis* hybrid enzyme with truncation site X4 disclosed in WO 2011/087836 or shown in SEQ ID NO: 12 herein.
58. The process of any of paragraphs 1-57, further comprises, prior to the liquefaction step a), the steps of:
   i) reducing the particle size of the starch-containing material, preferably by dry milling;
   ii) forming a slurry comprising the starch-containing material and water.
59. The process of any of paragraphs 1-58, wherein at least 50%, preferably at least 70%, more preferably at least 80%, especially at least 90% of the starch-containing material fit through a sieve with #6 screen.
60. The process of any of paragraphs 1-59, wherein the pH during liquefaction is between above 4.5-6.5, such as around 4.8, or a pH between 5.0-6.2, such as 5.0-6.0, such as between 5.0-5.5, such as around 5.2, such as around 5.4, such as around 5.6, such as around 5.8.
61. The process of any of paragraphs 1-60, wherein the temperature during liquefaction is above the initial gelatinization temperature, preferably in the range from 70-100° C., such as between 75-95° C., such as between 75-90° C., preferably between 80-90° C., especially around 85° C.
62. The process of any of paragraphs 1-61, wherein a jet-cooking step is carried out before liquefaction in step a).
63. The process of paragraph 62, wherein the jet-cooking is carried out at a temperature between 110-145° C., preferably 120-140° C., such as 125-135° C., preferably around 130° C. for about 1-15 minutes, preferably for about 3-10 minutes, especially around about 5 minutes.
64. The process of any of paragraphs 1-63, wherein saccharification and fermentation is carried out sequentially or simultaneously.
65. The process of any of paragraphs 1-64, wherein saccharification is carried out at a temperature from 20-75° C., preferably from 40-70° C., such as around 60° C., and at a pH between 4 and 5.
66. The process of any of paragraphs 1-65, wherein fermentation or simultaneous saccharification and fermentation (SSF) is carried out carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.
67. The process of any of paragraphs 1-66, wherein the fermentation product is recovered after fermentation, such as by distillation.
68. The process of any of paragraphs 1-67, wherein the fermentation product is an alcohol, preferably ethanol, especially fuel ethanol, potable ethanol and/or industrial ethanol.
69. The process of any of paragraphs 1-68, wherein the starch-containing starting material is whole grains.
70. The process of any of paragraphs 1-69, wherein the starch-containing material is selected from the group of corn, wheat, barley, rye, milo, sago, cassava, manioc, tapioca, sorghum, rice, and potatoes.
71. The process of any of paragraphs 1-70, wherein the fermenting organism is yeast, preferably a strain of *Saccharomyces*, especially a strain of *Saccharomyces cerevisae*.
72. The process of any of paragraphs 1-71, wherein the alpha-amylase is a bacterial or fungal alpha-amylase.
73. The process of any of paragraphs 1-72, wherein saccharification step b) and fermentation step c) are carried out simultaneously or sequentially.
74. The process of any of paragraphs 1-73, wherein the temperature in step (a) is above the initial gelatinization temperature, such as at a temperature between 80-90° C., such as around 85° C.
75. The process of any of paragraphs 1-74, further comprising a pre-saccharification step, before saccharification step b), carried out for 40-90 minutes at a temperature between 30-65° C.
76. The process of any of paragraphs 1-75, wherein saccharification is carried out at a temperature from 20-75° C., preferably from 40-70° C., such as around 60° C., and at a pH between 4 and 5.
77. The process of any of paragraphs 1-76, wherein fermentation step c) or simultaneous saccharification and fermentation (SSF) (i.e., steps b) and c)) are carried out carried out at a temperature from 25° C. to 40° C., such as from 28° C. to 35° C., such as from 30° C. to 34° C., preferably around about 32° C.
78. The process of any of paragraphs 1-77, wherein fermentation step c) or simultaneous saccharification and fermentation (SSF) (i.e., steps b) and c)) are ongoing for 6 to 120 hours, in particular 24 to 96 hours.
79. The process of any of paragraphs 1-78, wherein separation in step e) is carried out by centrifugation, preferably a decanter centrifuge, filtration, preferably using a filter press, a screw press, a plate-and-frame press, a gravity thickener or decker.
80. The process of any of paragraphs 1-79, wherein the fermentation product is recovered by distillation.
81. A process of recovering oil of any of paragraphs 1-80, comprising the steps of:
a) liquefying starch-containing material at a temperature above the initial gelatinization temperature using:
   *Bacillus stearothermophilus* alpha-amylase comprising a double deletion at positions I181+G182 using SEQ ID NO: 1 for numbering;
   more than 0.5 micro gram *Pyrococcus furiosus* protease per gram dry solids (DS);
   *Penicillium oxalicum* shown in SEQ ID NO: 14 comprising a K79V substitution;
b) saccharifying using a glucoamylase;
c) fermenting using a fermenting organism.
d) recovering the fermentation product to form whole stillage;
e) separating the whole stillage into thin stillage and wet cake;
f) optionally concentrating the thin stillage into syrup;
wherein oil is recovered from the:
   liquefied starch-containing material after step a); and/or
   downstream from fermentation step c).
82. A process of recovering oil of any of paragraphs 1-81 comprising the steps of:
a) liquefying starch-containing material at a temperature above the initial gelatinization temperature using:
   *Bacillus stearothermophilus* alpha-amylase comprising a double deletion at positions I181+G182 and the following substitutions N193F+V59A+Q89R+E129V+ K177L+R179E+Q254S+M284V truncated to 491 amino acids (using SEQ ID NO: 1 for numbering).
more than 0.5 micro gram *Pyrococcus furiosus* protease per gram dry solids (DS);
*Penicillium oxalicum* glucoamylase having the following mutations: K79V+P2N+P4S+P11F+T65A+Q327F (using SEQ ID NO: 14 for numbering);
b) saccharifying using a glucoamylase;
c) fermenting using a fermenting organism.
d) recovering the fermentation product to form whole stillage;
e) separating the whole stillage into thin stillage and wet cake;
f) optionally concentrating the thin stillage into syrup;
wherein oil is recovered from the:
liquefied starch-containing material after step a); and/or
downstream from fermentation step c).

83. The process of any of paragraphs 1-82, wherein the ratio between alpha-amylase and glucoamylase in liquefaction is between 1:1 and 1:10, such as around 1:2 (micro gram alpha-amylase per gram DS: micro gram glucoamylase per gram DS).

84. The process of any of paragraphs 1-83, wherein the ratio between alpha-amylase and protease in liquefaction is in the range between 1:1 and 1:25, such between 1:1.2 and as 1:10, such as around 1:1.4 (micro gram alpha-amylase per gram DS: micro gram protease per gram DS).

85. A process for producing fermentation products from starch-containing material comprising the steps of:
a) liquefying the starch-containing material at a temperature above the initial gelatinization temperature using:
an alpha-amylase;
more than 2 micro gram *Pyrococcus furiosus* protease per gram dry solids (DS);
b) saccharifying using a glucoamylase;
c) fermenting using a fermenting organism.

86. The process of paragraph 85, wherein 2-100 micro gram per gram DS, such as 2.5-50 micro gram per gram DS, such as 2.5-10 micro gram per gram DS, such as 2.5-5 micro gram per gram DS, especially around 3 micro gram per gram DS *Pyrococcus furiosus* protease.

87. The process of any of paragraph 85 or 86, wherein the *Pyrococcus furiosus* protease is the one shown in SEQ ID NO: 13 herein.

88. The process of any of paragraphs 85-87, wherein the *Pyrococcus furiosus* protease is one having at least 80%, such as at least 85%, such as at least 90%, such as at least 95%, such as at least 96%, such as at least 97%, such as at least 98%, such as at least 99% identity to SEQ ID NO: 13 herein.

89. The process of any of paragraphs 85-88, wherein no nitrogen-compound is present and/or added in steps a)-c), such as during saccharification step b) or fermentation step c) or simultaneous saccharification and fermentation (SSF).

90. The process of any of paragraphs 85-89, wherein 10-1,000 ppm, such as 50-800 ppm, such as 100-600 ppm, such as 200-500 ppm nitrogen-compound, preferably urea, is present and/or added in steps a)-c), such as during saccharification step b) or fermentation step c) or simultaneous saccharification and fermentation (SSF).

91. The process of any of paragraphs 85-90, wherein the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein, or a variant thereof or a strain of *Bacillus licheniformis*, such as the one shown in SEQ ID NO: 21 herein.

92. The process of paragraph 91, wherein the *Bacillus stearothermophilus* alpha-amylase or variant thereof is truncated, preferably to have around 491 amino acids, such as from 480-495 amino acids.

93. The process of any of paragraphs 91 or 92, wherein the *Bacillus stearothermophilus* alpha-amylase has a double deletion at positions I181+G182 and optionally a N193F substitution, or deletion of R179 and G180 (using SEQ ID NO: 1 for numbering).

94. The process of any of paragraphs 85-93 wherein the *Bacillus stearothermophilus* alpha-amylase has a substitution at position S242, preferably S242Q substitution.

95. The process of any of paragraphs 85-94, wherein the *Bacillus stearothermophilus* alpha-amylase has a substitution at position E188, preferably E188P substitution.

96. The process of any of paragraphs 85-95, wherein the alpha-amylase has a T½ (min) at pH 4.5, 85° C., 0.12 mM CaCl$_2$) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

97. The process of any of paragraphs 85-96, wherein the alpha-amylase is selected from the group of *Bacillus stearothermophilus* alpha-amylase variants with the following mutations in addition to I181*+G182* and optionally N193F:

V59A + Q89R + G112D + E129V + K177L + R179E + K220P + N224L + Q254S;
V59A + Q89R + E129V + K177L + R179E + H208Y + K220P + N224L + Q254S;
V59A + Q89R + E129V + K177L + R179E + K220P + N224L + Q254S + D269E + D281N;
V59A + Q89R + E129V + K177L + R179E + K220P + N224L + Q254S + I270L;
V59A + Q89R + E129V + K177L + R179E + K220P + N224L + Q254S + H274K;
V59A + Q89R + E129V + K177L + R179E + K220P + N224L + Q254S + Y276F;
V59A + E129V + R157Y + K177L + R179E + K220P + N224L + S242Q + Q254S;
V59A + E129V + K177L + R179E + H208Y + K220P + N224L + S242Q + Q254S;
59A + E129V + K177L + R179E + K220P + N224L + S242Q + Q254S;
V59A + E129V + K177L + R179E + K220P + N224L + S242Q + Q254S + H274K;
V59A + E129V + K177L + R179E + K220P + N224L + S242Q + Q254S + Y276F;
V59A + E129V + K177L + R179E + K220P + N224L + S242Q + Q254S + D281N;
V59A + E129V + K177L + R179E + K220P + N224L + S242Q + Q254S + M284T;
V59A + E129V + K177L + R179E + K220P + N224L + S242Q + Q254S + G416V;
V59A + E129V + K177L + R179E + K220P + N224L + Q254S;
V59A + E129V + K177L + R179E + K220P + N224L + Q254S + M284T;

-continued

A91L + M96I + E129V + K177L + R179E + K220P + N224L + S242Q + Q254S;
E129V + K177L + R179E;
E129V + K177L + R179E + K220P + N224L + S242Q + Q254S;
E129V + K177L + R179E + K220P + N224L + S242Q + Q254S + Y276F + L427M;
E129V + K177L + R179E + K220P + N224L + S242Q + Q254S + M284T;
E129V + K177L + R179E + K220P + N224L + S242Q + Q254S + N376* + I377*;
E129V + K177L + R179E + K220P + N224L + Q254S;
E129V + K177L + R179E + K220P + N224L + Q254S + M284T;
E129V + K177L + R179E + S242Q;
E129V + K177L + R179V + K220P + N224L + S242Q + Q254S;
K220P + N224L + S242Q + Q254S;
M284V;
V59A Q89R + E129V + K177L + R179E + Q254S + M284V.

98. The process of any of paragraphs 85-97, wherein the alpha-amylase is selected from the group of *Bacillus stearothermophilus* alpha-amylase variants:
   I181*+G182*+N193F+E129V+K177L+R179E;
   I181*+G182*+N193F+V59A+Q89R+E129V+K177L+ R179E+H208Y+K220P+N224L+Q254S
   I181*+G182*+N193F+V59A Q89R+E129V+K177L+ R179E+Q254S+M284V; and
   I181*+G182*+N193F+E129V+K177L+R179E+K220P+ N224L+S242Q+Q254S (using SEQ ID NO: 1 for numbering).
99. The process of any of paragraphs 91-98, wherein the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 1 herein.
100. The process of any of paragraphs 85-98, wherein the alpha-amylase is a *Bacillus licheniformis* alpha-amylase, or a variant thereof.
101. The process of paragraph 100, wherein the *Bacillus licheniformis* alpha-amylase is the one shown in SEQ ID NO: 21 herein.
102. The process of any of paragraphs 100-101, wherein the alpha-amylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% identity to the mature part of the polypeptide of SEQ ID NO: 21 herein.
103. The process of any of paragraphs 85-102, wherein the alpha-amylase is present and/or added in a concentration of 0.1-100 micro gram per gram DS, such as 0.5-50 micro gram per gram DS, such as 1-25 micro gram per gram DS, such as 1-10 micro gram per gram DS, such as 2-5 micro gram per gram DS.
104. The process of any of paragraphs 85-103, wherein from 1-10 micro gram *Pyrococcus furiosus* protease and 1-10 micro gram *Bacillus stearothermophilus* alpha-amylase are present and/or added in liquefaction.
105. The process of any of paragraphs 85-104, wherein a glucoamylase is present and/or added in liquefaction step i).
106. The process of paragraph 105, wherein the glucoamylase present and/or added in liquefaction has a heat stability at 85° C., pH 5.3, of at least 20%, such as at least 30%, preferably at least 35%.
107. The process of paragraph 105 or 106, wherein the glucoamylase has a relative activity pH optimum at pH 5.0 of at least 90%, preferably at least 95%, preferably at least 97%.
108. The process of any of paragraphs 105-102, wherein the glucoamylase has a pH stability at pH 5.0 of at least at least 80%, at least 85%, at least 90%.
109. The process of any of paragraphs 105-103, wherein the glucoamylase present and/or added in liquefaction step i) is derived from a strain of the genus *Penicillium*, especially a strain of *Penicillium oxalicum* disclosed as SEQ ID NO: 2 in WO 2011/127802 or SEQ ID NOs: 9 or 14 herein.
110. The process of paragraph 105-109, wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 9 or 14 herein.
111. The process of any of paragraphs 105-110, wherein the glucoamylase is a variant of the *Penicillium oxalicum* glucoamylase shown in SEQ ID NO: 2 in WO 2011/127802 having a K79V substitution (using the mature sequence shown in SEQ ID NO: 14 for numbering), such as a variant disclosed in WO 2013/053801.
112. The process of any of paragraph 105-111, wherein the *Penicillium oxalicum* glucoamylase has a K79V substitution (using SEQ ID NO: 14 for numbering) and further one of the following:
T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+I172V+Q327F+E501V+Y504T; or
P2N+P4S+P11F+T65A+Q327F+S377T+E501V+Y504T; or
P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or
P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or
P2N+P4S+P11F+T65A+Q327F+E501V+Y504T+T568N; or
P2N+P4S+P11F+T65A+Q327F+E501V+Y504T+K524T+G526A; or
P2N+P4S+P11F+K34Y+T65A+Q327F+D445N+V447S+E501V+Y504T; or
P2N+P4S+P11F+R31 S+K33V+T65A+Q327F+D445N+V447S+E501V+Y504T; or
P2N+P4S+P11F+D26N+K34Y+T65A+Q327F+E501V+Y504T; or
P2N+P4S+P11F+T65A+F80*+Q327F+E501V+Y504T; or
P2N+P4S+P11F+T65A+K112S+Q327F+E501V+Y504T; or
P2N+P4S+P11F+T65A+Q327F+E501V+Y504T+T516P+K524T+G526A; or
P2N+P4S+P11F+T65A+Q327F+E501V+N502T+Y504*; or
P2N+P4S+P11F+T65A+Q327F+E501V+Y504T; or
P2N+P4S+P11F+T65A+S103N+Q327F+E501V+Y504T; or
K5A+P11F+T65A+Q327F+E501V+Y504T; or
P2N+P4S+P11F+T65A+Q327F+E501V+Y504T+T516P+K524T+G526A; or
P2N+P4S+P11F+T65A+K79A+Q327F+E501V+Y504T; or
P2N+P4S+P11F+T65A+K79G+Q327F+E501V+Y504T; or
P2N+P4S+P11F+T65A+K79I+Q327F+E501V+Y504T; or
P2N+P4S+P11F+T65A+K79L+Q327F+E501V+Y504T; or
P2N+P4S+P11F+T65A+K79S+Q327F+E501V+Y504T; or
P2N+P4S+P11F+T65A+L72V+Q327F+E501V+Y504T; or
S255N+Q327F+E501V+Y504T; or
P2N+P4S+P11F+T65A+E74N+V79K+Q327F+E501V+Y504T; or
P2N+P4S+P11F+T65A+G220N+Q327F+E501V+Y504T; or
P2N+P4S+P11F+T65A+Y245N+Q327F+E501V+Y504T; or
P2N+P4S+P11F+T65A+Q253N+Q327F+E501V+Y504T; or
P2N+P4S+P11F+T65A+D279N+Q327F+E501V+Y504T; or
P2N+P4S+P11F+T65A+Q327F+S359N+E501V+Y504T; or
P2N+P4S+P11F+T65A+Q327F+D370N+E501V+Y504T; or
P2N+P4S+P11F+T65A+Q327F+V460S+E501V+Y504T; or
P2N+P4S+P11F+T65A+Q327F+V460T+P468T+E501V+Y504T; or
P2N+P4S+P11F+T65A+Q327F+T463N+E501V+Y504T; or
P2N+P4S+P11F+T65A+Q327F+S465N+E501V+Y504T; or
P2N+P4S+P11F+T65A+Q327F+T477N+E501V+Y504T.

113. The process of any of paragraphs 105-112, wherein the glucoamylase present and/or added in liquefaction is the Penicillium oxalicum.glucoamylase having a K79V substitution (using SEQ ID NO: 14 for numbering) and further one of the following:
P11F T65A Q327F
P2N P4S P11F T65A Q327F (using SEQ ID NO: 14 for numbering).

114. The process of any of paragraphs 105-113, wherein the glucoamylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 14 herein.

115. The process of any of paragraphs 85-114, further wherein a glucoamylase is present and/or added in saccharification and/or fermentation.

116. The process of paragraph 115, wherein the glucoamylase present and/or added in saccharification and/or fermentation is of fungal origin, preferably from a stain of *Aspergillus*, preferably *A. niger*, *A. awamori*, or *A. oryzae*;

or a strain of *Trichoderma*, preferably *T. reesei*; or a strain of *Talaromyces*, preferably *T. emersonii*, or a strain of *Pycnoporus*, or a strain of *Gloephyllum*, such as *G. serpiarium* or *G. trabeum*, or a strain of the *Nigrofomes*.

117. The process of any of paragraphs 115-116, wherein the glucoamylase is derived from *Talaromyces emersonii*, such as the one shown in SEQ ID NO: 19 herein, 118. The process of any of paragraphs 115-117, wherein the glucoamylase is selected from the group consisting of:
(i) a glucoamylase comprising the mature polypeptide of SEQ ID NO: 19 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 19 herein.

119. The process of any of paragraphs 115-119, wherein the glucoamylase is derived from *Gloephyllum serpiarium*, such as the one shown in SEQ ID NO: 15 herein.

120. The process of any of paragraphs 115-119, wherein the glucoamylase is selected from the group consisting of:
(i) a glucoamylase comprising the mature polypeptide of SEQ ID NO: 15 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 15 herein.

121. The process of any of paragraphs 115-120, wherein the glucoamylase is derived from *Gloeophyllum trabeum* such as the one shown in SEQ ID NO: 17 herein.

122. The process of any of paragraphs 115-121, wherein the glucoamylase is selected from the group consisting of:
(i) a glucoamylase comprising the mature polypeptide of SEQ ID NO: 17 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 17 herein.

123. The process of any of paragraphs 115-122, wherein the glucoamylase is present in saccharification and/or fermentation in combination with an alpha-amylase.

124. The process of paragraph 123, wherein the alpha-amylase is present in saccharification and/or fermentation is of fungal or bacterial origin.

125. The process of paragraph 123 or 124, wherein the alpha-amylase present and/or added in saccharification and/or fermentation is derived from a strain of the genus *Rhizomucor*, preferably a strain the *Rhizomucor pusillus*, such as the one shown in SEQ ID NO: 3 in WO 2013/006756, such as a *Rhizomucor pusillus* alpha-amylase hybrid having an *Aspergillus niger* linker and starch-bonding domain, such as the one shown in SEQ ID NO: 16.

126. The process of any of paragraphs 123-125, wherein the alpha-amylase present in saccharification and/or fermentation is selected from the group consisting of:
(i) an alpha-amylase comprising the mature polypeptide of SEQ ID NO: 16 herein;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 16 herein.

127. The process of any of paragraphs 123-126, wherein the alpha-amylase is a variant of the alpha-amylase shown in SEQ ID NO: 13 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 16 for numbering).

128. The process of any of paragraphs 123-127, wherein the alpha-amylase is derived from a *Rhizomucor pusillus* with an *Aspergillus niger* glucoamylase linker and starch-binding domain (SBD), preferably disclosed as SEQ ID NO: 16 herein, preferably having one or more of the following substitutions: G128D, D143N, preferably G128D+D143N (using SEQ ID NO: 16 for numbering).

129. The process of any of paragraphs 123-128, wherein the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 16 herein.

130. The process of any of paragraphs 85-129, further wherein a pullulanase is present and/or added in liquefaction and/or saccharification and/or fermentation.

131. The process of paragraph 130, wherein the pullulanase is a family GH57 pullulanase, wherein the pullulanase preferably includes an X47 domain as disclosed in WO 2011/087836.

132. The process of paragraphs 130-131, wherein the pullulanase is derived from a strain from the genus *Thermococcus*, including *Thermococcus litoralis* and *Thermococcus hydrothermalis* or a hybrid thereof.

133. The process of any of paragraphs 130-132, wherein the pullulanase is the truncated *Thermococcus hydrothermalis* pullulanase at site X4 or a *T. hydrothermalis/T. litoralis* hybrid enzyme with truncation site X4 disclosed in WO 2011/087836 or shown in SEQ ID NO: 12 herein.

134. The process of any of paragraphs 85-133, further comprises, prior to the liquefaction step i), the steps of:
i) reducing the particle size of the starch-containing material, preferably by dry milling;
ii) forming a slurry comprising the starch-containing material and water.

135. The process of any of paragraphs 85-134, wherein at least 50%, preferably at least 70%, more preferably at least 80%, especially at least 90% of the starch-containing material fit through a sieve with #6 screen.

136. The process of any of paragraphs 85-135, wherein the pH in liquefaction is between above 4.5-6.5, such as around 4.8, or a pH between 5.0-6.2, such as 5.0-6.0, such as between 5.0-5.5, such as around 5.2, such as around 5.4, such as around 5.6, such as around 5.8.

137. The process of any of paragraphs 85-136, wherein the temperature in liquefaction is above the initial gelatinization temperature, such as in the range from 70-100° C., such as between 75-95° C., such as between 75-90° C., preferably between 80-90° C., especially around 85° C.

138. The process of any of paragraphs 85-137, wherein a jet-cooking step is carried out before liquefaction in step a).

139. The process of paragraph 138, wherein the jet-cooking is carried out at a temperature between 110-145° C., preferably 120-140° C., such as 125-135° C., preferably around 130° C. for about 1-15 minutes, preferably for about 3-10 minutes, especially around about 5 minutes.

140. The process of any of paragraphs 85-139, wherein saccharification and fermentation is carried out sequentially or simultaneously.

141. The process of any of paragraphs 85-140, wherein saccharification is carried out at a temperature from 20-75° C., preferably from 40-70° C., such as around 60° C., and at a pH between 4 and 5.

142. The process of any of paragraphs 85-141, wherein fermentation or simultaneous saccharification and fermentation (SSF) is carried out carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

143. The process of any of paragraphs 85-142, wherein the fermentation product is recovered after fermentation, such as by distillation.

144. The process of any of paragraphs 85-143, wherein the fermentation product is an alcohol, preferably ethanol, especially fuel ethanol, potable ethanol and/or industrial ethanol.

145. The process of any of paragraphs 85-144, wherein the starch-containing starting material is whole grains.

146. The process of any of paragraphs 85-145, wherein the starch-containing material is derived from corn, wheat, barley, rye, milo, sago, cassava, manioc, tapioca, sorghum, rice or potatoes.

147. The process of any of paragraphs 85-146, wherein the fermenting organism is yeast, preferably a strain of *Saccharomyces*, especially a strain of *Saccharomyces cerevisae*.

148. The process of any of paragraphs 85-147, wherein the alpha-amylase is a bacterial or fungal alpha-amylase.

149. The process of any of paragraphs 85-148, comprising the steps of:
a) liquefying the starch-containing material at a temperature above the initial gelatinization temperature using:
  an alpha-amylase derived from *Bacillus stearothermophilus*;
  more than 2 micro gram *Pyrococcus furiosus* protease per gram dry solids (DS); and
  optionally a *Penicillium oxalicum* glucoamylase;
b) saccharifying using a glucoamylase enzyme;
c) fermenting using a fermenting organism.

150. A process of paragraphs 85-149, comprising the steps of:
a) liquefying the starch-containing material at a temperature above the initial gelatinization temperature using:
  an alpha-amylase, preferably derived from *Bacillus stearothermophilus*, having a T ½ (min) at pH 4.5, 85° C., 0.12 mM CaCl$_2$ of at least 10;
  more than 2 micro gram *Pyrococcus furiosus* protease per gram dry solids (DS); and
  optionally a glucoamylase;
b) saccharifying using a glucoamylase enzyme;
c) fermenting using a fermenting organism.

151. A process of paragraphs 85-150, comprising the steps of:
a) liquefying the starch-containing material at a temperature above the initial gelatinization temperature using:
  an alpha-amylase, preferably derived from *Bacillus stearothermophilus*, having a T ½ (min) at pH 4.5, 85° C., 0.12 mM CaCl$_2$ of at least 10;
  more than 2 micro gram *Pyrococcus furiosus* protease per gram dry solids (DS); and
  a *Penicillium oxalicum* glucoamylasea;
b) saccharifying using a glucoamylase enzyme;
c) fermenting using a fermenting organism.

152. A process of paragraphs 85-151, comprising the steps of:
a) liquefying the starch-containing material at a temperature above the initial gelatinization temperature using:
  an alpha-amylase derived from *Bacillus stearothermophilus* having a double deletion at positions I181+G182, and optional substitution N193F; further one of the following set of substitutions:
    E129V+K177L+R179E;
    V59A+Q89R+E129V+K177L+R179E+H208Y+K220P+N224L+Q254S;
    V59A+Q89R+E129V+K177L+R179E+Q254S+M284V;
    E129V+K177L+R179E+K220P+N224L+S242Q+Q254S (using SEQ ID NO: 1 herein for numbering);
  more than 2 micro gram *Pyrococcus furiosus* protease per gram dry solids (DS);
  a *Penicillium oxalicum* glucoamylase in SEQ ID NO: 14 having substitutions selected from the group of:
    K79V;
    K79V+P11F+T65A+Q327F; or
    K79V+P2N+P4S+P11F+T65A+Q327F; or
    K79V+P11F+D26C+K33C+T65A+Q327F; or
    K79V+P2N+P4S+P11F+T65A+Q327W+E501V+Y504T; or
    K79V+P2N+P4S+P11F+T65A+Q327F+E501V+Y504T; or
    K79V+P11F+T65A+Q327W+E501V+Y504T (using SEQ ID NO: 14 for
    numbering);
b) saccharifying using a glucoamylase enzyme;
c) fermenting using a fermenting organism.

153. A process of paragraphs 85-152, comprising the steps of:
a) liquefying the starch-containing material at a pH in the range between from above 4.5-6.5 at a temperature between 80-90° C. using:
  an alpha-amylase derived from *Bacillus stearothermophilus* having a double deletion I181+G182 and optional substitution N193F; and further one of the following set of substitutions:
    E129V+K177L+R179E;
    V59A+Q89R+E129V+K177L+R179E+H208Y+K220P+N224L+Q254S;
    V59A+Q89R+E129V+K177L+R179E+Q254S+M284V;
    E129V+K177L+R179E+K220P+N224L+S242Q+Q254S (using SEQ ID NO: 1 herein for numbering);
  more than 2 micro gram, such as between 2-5 micro gram, preferably around 3 micro gram *Pyrococcus furiosus* protease per gram DS dry solids (DS);
  a *Penicillium oxalicum* glucoamylase in SEQ ID NO: 14 having substitutions selected from the group of:

K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+ Y504T; or
K79V+P2N+P4S+P11F+T65A+Q327F+E501V+ Y504T; or
K79V+P11F+T65A+Q327W+E501V+Y504T (using SEQ ID NO: 14 for numbering);
b) saccharifying using a glucoamylase enzyme;
c) fermenting using a fermenting organism.

154. A process of paragraphs 85-153, comprising the steps of:
a) liquefying the starch-containing material at a pH in the range between from above 4.5-6.5 at a temperature between 80-90° C. using:
an alpha-amylase derived from *Bacillus stearothermophilus* having a double deletion I181+G182 and substitution N193F; and further one of the following set of substitutions:
E129V+K177L+R179E;
V59A+Q89R+E129V+K177L+R179E+H208Y+ K220P+N224L+Q254S;
V59A+Q89R+E129V+K177L+R179E+Q254S+ M284V;
E129V+K177L+R179E+K220P+N224L+S242Q+ Q254S (using SEQ ID NO: 1 herein for numbering);
more than 2 micro gram, such as between 2-5 micro gram, preferably around 3 micro gram *Pyrococcus furiosus* protease per gram DS dry solids (DS)
a *Penicillium oxalicum* glucoamylase in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+ Y504T; or
K79V+P2N+P4S+P11F+T65A+Q327F+E501V+ Y504T; or
K79V+P11F+T65A+Q327W+E501V+Y504T (using SEQ ID NO: 14 for numbering);
b) saccharifying using a *Rhizomucor pusillus* glucoamylase with an *Aspergillus niger* glucoamylase linker and starch-binding domain (SBD), preferably disclosed as SEQ ID NO: 13 herein, preferably having one or more of the following substitutions: G128D, D143N, preferably G128D+D143N (using SEQ ID NO: 13 for numbering);
c) fermenting using a fermenting organism.

155. A process of any of paragraphs 85-154, wherein the ratio between alpha-amylase and glucoamylase in liquefaction is between 1:1 and 1:10, such as around 1:2 (micro gram alpha-amylase per g DS: micro gram glucoamylase per gram DS).

156. A process of any of paragraphs 85-155, wherein the ratio between alpha-amylase and protease in liquefaction is in the range between 1:1 and 1:25, such between 1:1.2 and as 1:10, such as around 1:1.4 (micro gram alpha-amylase per g DS: micro gram protease per gram DS).

157. An enzyme composition comprising:
i) *Bacillus* sp. alpha-amylase, or a variant thereof;
ii) *Pyrococcus furiosus* protease;
wherein the ratio between alpha-amylase and protease is in the range from 1:1 and 1:25 (micro gram alpha-amylase: micro gram protease).

158. The enzyme composition paragraph 157, wherein the ratio between alpha-amylase and protease is in the range between 1:1.2 and 1:10, such as around 1:1.4 (micro gram alpha-amylase: micro gram protease).

159. The enzyme composition of any of paragraphs 157-158, wherein the enzyme composition comprises a glucoamylase and the ratio between alpha-amylase and glucoamylase in liquefaction is between 1:1 and 1:10, such as around 1:2 (micro gram alpha-amylase:micro gram glucoamylase).

160. The enzyme composition of any of paragraphs 157-159, wherein the alpha-amylase is a bacterial or fungal alpha-amylase.

161. The enzyme composition of any of paragraphs 157-160, wherein the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein.

162. The enzyme composition of any of paragraphs 157-161, wherein the *Bacillus stearothermophilus* alpha-amylase or variant thereof is truncated, preferably to have around 491 amino acids, such as from 480-495 amino acids.

163. The enzyme composition of any of paragraphs 157-162, wherein the *Bacillus stearothermophilus* alpha-amylase has a double deletion, preferably at positions I181+ G182 and optionally a N193F substitution, or double deletion of R179 and G180 (using SEQ ID NO: 1 for numbering).

164. The enzyme composition of any of paragraphs 157-163 wherein the *Bacillus stearothermophilus* alpha-amylase has a substitution at position S242, preferably S242Q substitution.

165. The enzyme composition of any of paragraphs 157-164, wherein the *Bacillus stearothermophilus* alpha-amylase has a substitution at position E188, preferably E188P substitution.

166. The enzyme composition of any of paragraphs 157-165, wherein the alpha-amylase has a T½ (min) at pH 4.5, 85° C., 0.12 mM $CaCl_2$) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

167. The enzyme composition of any of paragraphs 157-166, wherein the alpha-amylase is selected from the group of *Bacillus stearomthermphilus* alpha-amylase variants with the following mutations:
I181*+G182*+N193F+E129V+K177L+R179E;
I181*+G182*+N193F+V59A+Q89R+E129V+K177L+ R179E+H208Y+K220P+N224L+Q254S;
I181*+G182*+N193F+V59A Q89R+E129V+K177L+ R179E+Q254S+M284V; and
I181*+G182*+N193F+E129V+K177L+R179E+K220P+ N224L+S242Q+Q254S (using SEQ ID NO: 1 herein for numbering).

168. The enzyme composition of any of paragraphs 157-167, wherein the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 1 herein.

169. The enzyme composition of any of paragraphs 157-168, wherein the alpha-amylase is a *Bacillus licheniformis* alpha-amylase, or a variant thereof.

170. The enzyme composition of paragraph 169, wherein the *Bacillus licheniformis* alpha-amylase is the one shown in SEQ ID NO: 21 herein.

171. The enzyme composition of any of paragraphs 157-170, wherein the alpha-amylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% identity to the mature part of the polypeptide of SEQ ID NO: 21 herein.

172. The enzyme composition of any of paragraphs 157-171, wherein the enzyme composition comprises a *Bacillus licheniformis* alpha-amylase and a *Pyrococcus furiosus* protease.

173. The enzyme composition of any of paragraphs 157-172, wherein the enzyme composition further comprises a glucoamylase.

174. The composition of any of paragraphs 157-173, wherein the *Pyrococcus furiosus* is the one shown in SEQ ID NO: 13 herein.

175. The composition of any of paragraphs 157-174, wherein the *Pyrococcus furiosus* protease is one having at least 80%, such as at least 85%, such as at least 90%, such as at least 95%, such as at least 96%, such as at least 97%, such as at least 98%, such as at least 99% identity to SEQ ID NO: 13 herein.

176. The composition of any of paragraphs 157-175, wherein the enzyme composition further comprises a glucoamylase shown in SEQ ID NO: 14, or a variant thereof.

177. The composition of paragraph 152-166, wherein the glucoamylase has a heat stability at 85° C., pH 5.3, of at least 20%, such as at least 30%, preferably at least 35%.

178. The composition of any of paragraphs 176-177, wherein the glucoamylase has a relative activity pH optimum at pH 5.0 of at least 90%, preferably at least 95%, preferably at least 97%.

179. The composition of any of paragraphs 176-178, wherein the glucoamylase has a pH stability at pH 5.0 of at least at least 80%, at least 85%, at least 90%.

180. The composition of any of paragraphs 176-179, wherein the glucoamylase is derived from a strain of the genus *Penicillium*, especially a strain of *Penicillium oxalicum* disclosed as SEQ ID NO: 2 in WO 2011/127802 or SEQ ID NOs: 9 or 14 herein.

181. The composition of paragraph 176-170, wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 9 or 14 herein.

182. The composition of any of paragraphs 176-181, wherein the glucoamylase is a variant of the *Penicillium oxalicum* glucoamylase disclosed as SEQ ID NO: 2 in WO 2011/127802 or SEQ ID NO: 14 herein having a K79V substitution (using the mature sequence shown in SEQ ID NO: 14 for numbering) such as a variant disclosed in WO 2013/053801.

183. The composition of any of paragraph 176-182, wherein the *Penicillium oxalicum* glucoamylase has a K79V substitution (using SEQ ID NO: 14 for numbering) and further one of the following:

T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+I172V+Q327F+E501V+Y504T; or

P2N+P4S+P11F+T65A+Q327F+S377T+E501V+Y504T; or
P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or
P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or
P2N+P4S+P11F+T65A+Q327F+E501V+Y504T+T568N; or
P2N+P4S+P11F+T65A+Q327F+E501V+Y504T+K524T+G526A; or
P2N+P4S+P11F+K34Y+T65A+Q327F+D445N+V447S+E501V+Y504T; or
P2N+P4S+P11F+R31 S+K33V+T65A+Q327F+D445N+V447S+E501V+Y504T; or
P2N+P4S+P11F+D26N+K34Y+T65A+Q327F+E501V+Y504T; or
P2N+P4S+P11F+T65A+F80*+Q327F+E501V+Y504T; or
P2N+P4S+P11F+T65A+K112S+Q327F+E501V+Y504T; or
P2N+P4S+P11F+T65A+Q327F+E501V+Y504T+T516P+K524T+G526A; or
P2N+P4S+P11F+T65A+Q327F+E501V+N502T+Y504*; or
P2N+P4S+P11F+T65A+Q327F+E501V+Y504T; or
P2N+P4S+P11F+T65A+S103N+Q327F+E501V+Y504T; or
K5A+P11F+T65A+Q327F+E501V+Y504T; or
P2N+P4S+P11F+T65A+Q327F+E501V+Y504T+T516P+K524T+G526A; or
P2N+P4S+P11F+T65A+K79A+Q327F+E501V+Y504T; or
P2N+P4S+P11F+T65A+K79G+Q327F+E501V+Y504T; or
P2N+P4S+P11F+T65A+K79I+Q327F+E501V+Y504T; or
P2N+P4S+P11F+T65A+K79L+Q327F+E501V+Y504T; or
P2N+P4S+P11F+T65A+K79S+Q327F+E501V+Y504T; or
P2N+P4S+P11F+T65A+L72V+Q327F+E501V+Y504T; or
S255N+Q327F+E501V+Y504T; or
P2N+P4S+P11F+T65A+E74N+V79K+Q327F+E501V+Y504T; or
P2N+P4S+P11F+T65A+G220N+Q327F+E501V+Y504T; or
P2N+P4S+P11F+T65A+Y245N+Q327F+E501V+Y504T; or
P2N+P4S+P11F+T65A+Q253N+Q327F+E501V+Y504T; or
P2N+P4S+P11F+T65A+D279N+Q327F+E501V+Y504T; or
P2N+P4S+P11F+T65A+Q327F+S359N+E501V+Y504T; or
P2N+P4S+P11F+T65A+Q327F+D370N+E501V+Y504T; or
P2N+P4S+P11F+T65A+Q327F+V460S+E501V+Y504T; or
P2N+P4S+P11F+T65A+Q327F+V460T+P468T+E501V+Y504T; or
P2N+P4S+P11F+T65A+Q327F+T463N+E501V+Y504T; or
P2N+P4S+P11F+T65A+Q327F+S465N+E501V+Y504T; or
P2N+P4S+P11F+T65A+Q327F+T477N+E501V+Y504T.

184. The composition of any of paragraphs 176-183, wherein the glucoamylase is the *Penicillium oxalicum* glucoamylase having a K79V substitution (using SEQ ID NO: 14 for numbering) and further one of the following substitutions:
P11F+T65A+Q327F
P2N+P4S+P11F+T65A+Q327F (using SEQ ID NO: 14 for numbering).

185. The composition of any of paragraphs 182-184, wherein the glucoamylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 14 herein.

186. The composition of any of paragraphs 157-185, further comprising a pullulanase.

187. The composition of paragraph 186, wherein the pullulanase is a family GH57 pullulanase, wherein the pullulanase preferably includes an X47 domain as disclosed in WO 2011/087836.

188. The composition of paragraphs 186-187, wherein the pullulanase is derived from a strain from the genus *Thermococcus*, including *Thermococcus litoralis* and *Thermococcus hydrothermalis* or a hybrid thereof.

189. The composition of any of paragraphs 186-188, wherein the pullulanase is the truncated *Thermococcus hydrothermalis* pullulanase at site X4 or a *T. hydrothermalis/T. litoralis* hybrid enzyme with truncation site X4 disclosed in WO 2011/087836 or shown in SEQ ID NO: 12 herein.

190. The composition of any of paragraphs 157-189 comprising
*Bacillus stearothermophilus* alpha-amylase, or a variant thereof;
*Pyrococcus furiosus* protease; and
*Penicillium oxalicum* glucoamylase,
wherein the ratio between alpha-amylase and protease is in the range from 1:1 and 1:25 (micro gram alpha-amylase: micro gram protease).

191. The composition of any of paragraphs 157-190, comprising
an alpha-amylase, preferably derived from *Bacillus stearothermophilus*, having a T½ (min) at pH 4.5, 85° C., 0.12 mM CaCl$_2$ of at least 10;
*Pyrococcus furiosus* protease; and
*Penicillium oxalicum* glucoamylase,
wherein the ratio between alpha-amylase and protease is in the range from 1:1 and 1:25 (micro gram alpha-amylase: micro gram protease).

192. The composition of any of paragraphs 157-191, comprising
an alpha-amylase derived from *Bacillus stearothermophilus* having a double deletion I181+G182 and substitution N193F; and further one of the following set of substitutions:
E129V+K177L+R179E;
V59A+Q89R+E129V+K177L+R179E+H208Y+K220P+N224L+Q254S;
V59A+Q89R+E129V+K177L+R179E+Q254S+M284V;
E129V+K177L+R179E+K220P+N224L+S242Q+Q254S (using SEQ ID NO: 1 herein for numbering);

*Pyrococcus furiosus* protease; and
*Penicillium oxalicum* glucoamylase in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+Y504T; or
K79V+P2N+P4S+P11F+T65A+Q327F+E501V+Y504T; or
K79V+P11F+T65A+Q327W+E501V+Y504T (using SEQ ID NO: 14 for numbering), wherein the ratio between alpha-amylase and protease is in the range from 1:1 and 1:25 (micro gram alpha-amylase: micro gram protease).

193. The enzyme composition of any of paragraphs 190-192, wherein the ratio between alpha-amylase and protease is in the range between 1:1.2 and 1:10, such as around 1:1.4 (micro gram alpha-amylase:micro gram protease).

194. The enzyme composition of any of paragraphs 190-193, wherein the ratio between alpha-amylase and glucoamylase is between 1:1 and 1:10, such as around 1:2 (micro gram alpha-amylase: micro gram glucoamylase).

The invention claimed is:

1. A process for producing fermentation products from starch-containing material comprising the steps of:
   a) liquefying the starch-containing material at a temperature above the initial gelatinization temperature using:
      an alpha-amylase; and
      at least 2.5 micro gram *Pyrococcus furiosus* protease per gram dry solids (DS), wherein the protease is the one shown in SEQ ID NO: 13 or a protease having at least 90% sequence identity thereto;
   b) saccharifying using a glucoamylase; and
   c) fermenting using a fermenting organism.

2. The process of claim 1, wherein 2.5-100 micro gram per gram DS *Pyrococcus furiosus* protease is present and/or added in liquefaction step a).

3. The process of claim 1, wherein the *Pyrococcus furiosus* protease is one having at least 95% sequence identity to SEQ ID NO: 13.

4. The process of claim 1, wherein no nitrogen-compound is added in during liquefaction step a), saccharification step b) or fermentation step c) or simultaneous saccharification and fermentation (SSF).

5. The process of claim 1, wherein the protease has at least 96% sequence identity to SEQ ID NO: 13.

6. The process of claim 1, wherein the protease has at least 97% sequence identity to SEQ ID NO: 13.

7. The process of claim 1, wherein the protease has at least 98% sequence identity to SEQ ID NO: 13.

8. The process of claim 1, wherein the protease has at least 99% sequence identity to SEQ ID NO: 13.

9. The process of claim 1, wherein the alpha-amylase is a *Bacillus* amylase.

10. The process of claim 1, wherein the alpha-amylase is a *Bacillus stearothermophilus* alpha-amylase.

11. The process of claim 1, wherein the alpha-amylase is a *Bacillus stearothermophilus* alpha-amylase having a double deletion of positions I181+G182 or R179+G180 using SEQ ID NO: 1 for numbering.

12. The process of claim 1, wherein the alpha-amylase has the amino acid sequence of SEQ ID NO: 1 or is a variant thereof having at least 85% sequence identity thereto.

13. The process of claim 1, wherein the alpha-amylase has at least 90% sequence identity to the amino acid sequence of SEQ ID NO: 1.

14. The process of claim 1, wherein the alpha amylase has at least 95% sequence identity to the amino acid sequence of SEQ ID NO: 1.

15. The process of claim 1, further comprising using a glucoamylase in liquefying step (a).

16. The process of claim 1, further comprising using a glucoamylase in liquefying step (a), wherein the glucoamylase is a *Penicillum oxalicum* glucoamylase.

17. The process of claim 1, further comprising using a glucoamylase in liquefying step (a), wherein the glucoamylase has the amino acid sequence of SEQ ID NO: 14 or is a variant thereof having at least 85% sequence identity thereto.

18. The process of claim 17, wherein the glucoamylase has at least 90% sequence identity to the amino acid sequence of SEQ ID NO: 14.

19. The process of claim 17, wherein the glucoamylase has at least 95% sequence identity to the amino acid sequence of SEQ ID NO: 14.

20. The process of claim 1, further comprising using a pullulanase in liquefying step (a).

* * * * *

```
                       SEQUENCE LISTING

<160> NUMBER OF SEQ ID NOS: 21

<210> SEQ ID NO 1
<211> LENGTH: 515
<212> TYPE: PRT
<213> ORGANISM: Bacillus stearothermophilus
<220> FEATURE:
<221> NAME/KEY: mat_peptide
<222> LOCATION: (1)..(515)

<400> SEQUENCE: 1

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
```

```
                         260                 265                 270
Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 2
<211> LENGTH: 1068
<212> TYPE: DNA
<213> ORGANISM: Thermoascus aurantiacus
<220> FEATURE:
<221> NAME/KEY: CDS
<222> LOCATION: (1)..(1065)
<220> FEATURE:
<221> NAME/KEY: misc_signal
<222> LOCATION: (1)..(57)
<220> FEATURE:
<221> NAME/KEY: misc_feature
<222> LOCATION: (58)..(534)
<220> FEATURE:
<221> NAME/KEY: mat_peptide
<222> LOCATION: (535)..(1068)

<400> SEQUENCE: 2 atg cgg ctc gtt  gct tcc cta acg gcc  ttg gtg gcc ttg tcc  gta       45
Met Arg Leu Val  Ala Ser Leu Thr Ala  Leu Val Ala Leu Ser  Val
        -175                 -170                 -165 cct gtc ttt ccc  gct gct gtc aac gtg  aag cgt gct tcg tcc  tac       90
Pro Val Phe Pro  Ala Ala Val Asn Val  Lys Arg Ala Ser Ser  Tyr
        -160                 -155                 -150 ctg gag atc act  ctg agc cag gtc agc  aac act ctg atc aag  gcc      135
```

-continued

```
                Leu Glu Ile Thr     Leu Ser Gln Val Ser     Asn Thr Leu Ile Lys Ala
                        -145                -140                    -135
gtg gtc cag aac act ggt agc gac gag ttg tcc ttc gtt cac ctg                       180
Val Val Gln Asn Thr Gly Ser Asp Glu Leu Ser Phe Val His Leu
            -130                -125                -120 aac ttc ttc aag gac ccc gct cct gtc aaa aag gta tcg gtc tat                       225
Asn Phe Phe Lys Asp Pro Ala Pro Val Lys Lys Val Ser Val Tyr
            -115                -110                -105 cgc gat ggg tct gaa gtg cag ttc gag ggc att ttg agc cgc tac aaa                   273
Arg Asp Gly Ser Glu Val Gln Phe Glu Gly Ile Leu Ser Arg Tyr Lys
        -100                -95                    -90 tcg act ggc ctc tct cgt gac gcc ttt act tat ctg gct ccc gga gag                   321
Ser Thr Gly Leu Ser Arg Asp Ala Phe Thr Tyr Leu Ala Pro Gly Glu
        -85                -80                    -75 tcc gtc gag gac gtt ttt gat att gct tcg act tac gat ctg acc agc                   369
Ser Val Glu Asp Val Phe Asp Ile Ala Ser Thr Tyr Asp Leu Thr Ser
    -70                -65                    -60 ggc ggc cct gta act atc cgt act gag gga gtt gtt ccc tac gcc acg                   417
Gly Gly Pro Val Thr Ile Arg Thr Glu Gly Val Val Pro Tyr Ala Thr
-55                -50                    -45                -40 gct aac agc act gat att gcc ggc tac atc tca tac tcg tct aat gtg                   465
Ala Asn Ser Thr Asp Ile Ala Gly Tyr Ile Ser Tyr Ser Ser Asn Val
            -35                    -30                    -25 ttg acc att gat gtc gat ggc gcc gct gct gcc act gtc tcc aag gca                   513
Leu Thr Ile Asp Val Asp Gly Ala Ala Ala Ala Thr Val Ser Lys Ala
        -20                    -15                    -10 atc act cct ttg gac cgc cgc act agg atc agt tcc tgc tcc ggc agc                   561
Ile Thr Pro Leu Asp Arg Arg Thr Arg Ile Ser Ser Cys Ser Gly Ser
        -5                -1   1                    5 aga cag agc gct ctt act acg gct ctc aga aac gct gct tct ctt gcc                   609
Arg Gln Ser Ala Leu Thr Thr Ala Leu Arg Asn Ala Ala Ser Leu Ala
10                    15                    20                    25 aac gca gct gcc gac gcg gct cag tct gga tca gct tca aag ttc agc                   657
Asn Ala Ala Ala Asp Ala Ala Gln Ser Gly Ser Ala Ser Lys Phe Ser
                    30                    35                    40 gag tac ttc aag act act tct agc tct acc cgc cag acc gtg gct gcg                   705
Glu Tyr Phe Lys Thr Thr Ser Ser Ser Thr Arg Gln Thr Val Ala Ala
            45                    50                    55 cgt ctt cgg gct gtt gcg cgg gag gca tct tcg tct tct tcg gga gcc                   753
Arg Leu Arg Ala Val Ala Arg Glu Ala Ser Ser Ser Ser Ser Gly Ala
            60                    65                    70 acc acg tac tac tgc gac gat ccc tac ggc tac tgt tcc tcc aac gtc                   801
Thr Thr Tyr Tyr Cys Asp Asp Pro Tyr Gly Tyr Cys Ser Ser Asn Val
        75                    80                    85 ctg gct tac acc ctg cct tca tac aac ata atc gcc aac tgt gac att                   849
Leu Ala Tyr Thr Leu Pro Ser Tyr Asn Ile Ile Ala Asn Cys Asp Ile
90                    95                    100                    105 ttc tat act tac ctg ccg gct ctg acc agt acc tgt cac gct cag gat                   897
Phe Tyr Thr Tyr Leu Pro Ala Leu Thr Ser Thr Cys His Ala Gln Asp
                    110                    115                    120 caa gcg acc act gcc ctt cac gag ttc acc cat gcg cct ggc gtc tac                   945
Gln Ala Thr Thr Ala Leu His Glu Phe Thr His Ala Pro Gly Val Tyr
                125                    130                    135 agc cct ggc acg gac gac ctg gcg tat ggc tac cag gct gcg atg ggt                   993
Ser Pro Gly Thr Asp Asp Leu Ala Tyr Gly Tyr Gln Ala Ala Met Gly
            140                    145                    150 ctc agc agc agc cag gct gtc atg aac gct gac acc tac gct ctc tat                  1041
Leu Ser Ser Ser Gln Ala Val Met Asn Ala Asp Thr Tyr Ala Leu Tyr
    155                    160                    165
```

-continued

```
gcg aat gcc ata tac ctt ggt tgc taa                                  1068
Ala Asn Ala Ile Tyr Leu Gly Cys
170             175
```

<210> SEQ ID NO 3
<211> LENGTH: 355
<212> TYPE: PRT
<213> ORGANISM: Thermoascus aurantiacus

<400> SEQUENCE: 3

```
Met Arg Leu Val  Ala Ser Leu Thr  Ala Leu Val Ala  Leu Ser  Val
    -175              -170             -165

Pro Val Phe Pro  Ala Ala Val Asn  Val Lys Arg Ala  Ser Ser  Tyr
    -160              -155             -150

Leu Glu Ile Thr  Leu Ser Gln Val  Ser Asn Thr Leu  Ile Lys  Ala
    -145              -140             -135

Val Val Gln Asn  Thr Gly Ser Asp  Glu Leu Ser Phe  Val His  Leu
    -130              -125             -120

Asn Phe Phe Lys  Asp Pro Ala Pro  Val Lys Lys Val  Ser Val  Tyr
    -115              -110             -105

Arg Asp Gly Ser  Glu Val Gln Phe  Glu Gly Ile Leu  Ser Arg Tyr Lys
    -100               -95              -90

Ser Thr Gly Leu Ser Arg Asp Ala Phe Thr Tyr Leu Ala Pro Gly Glu
         -85              -80              -75

Ser Val Glu Asp Val Phe Asp Ile Ala Ser Thr Tyr Asp Leu Thr Ser
    -70              -65              -60

Gly Gly Pro Val Thr Ile Arg Thr Glu Gly Val Val Pro Tyr Ala Thr
-55              -50              -45              -40

Ala Asn Ser Thr  Asp Ile Ala Gly  Tyr Ile Ser Tyr  Ser Ser Asn Val
                 -35              -30              -25

Leu Thr Ile Asp  Val Asp Gly Ala  Ala Ala Thr Val  Ser Lys  Ala
    -20              -15              -10

Ile Thr Pro Leu  Asp Arg Arg Thr  Arg Ile Ser Ser  Cys Ser Gly Ser
    -5               -1   1                5

Arg Gln Ser Ala Leu Thr Thr Ala Leu Arg Asn Ala Ala Ser Leu Ala
10              15              20              25

Asn Ala Ala Ala Asp Ala Ala Gln Ser Gly Ser Ala Ser Lys Phe Ser
                30              35              40

Glu Tyr Phe Lys Thr Thr Ser Ser Thr Arg Gln Thr Val Ala Ala
                45              50              55

Arg Leu Arg Ala Val Ala Arg Glu Ala Ser Ser Ser Ser Gly Ala
60              65              70

Thr Thr Tyr Tyr Cys Asp Asp Pro Tyr Gly Tyr Cys Ser Ser Asn Val
    75              80              85

Leu Ala Tyr Thr Leu Pro Ser Tyr Asn Ile Ile Ala Asn Cys Asp Ile
90              95              100             105

Phe Tyr Tyr Tyr Leu Pro Ala Leu Thr Ser Thr Cys His Ala Gln Asp
                110             115             120

Gln Ala Thr Thr Ala Leu His Glu Phe Thr His Ala Pro Gly Val Tyr
                125             130             135

Ser Pro Gly Thr Asp Asp Leu Ala Tyr Gly Tyr Gln Ala Met Gly
            140             145             150

Leu Ser Ser Ser Gln Ala Val Met Asn Ala Asp Thr Tyr Ala Leu Tyr
    155             160             165

Ala Asn Ala Ile Tyr Leu Gly Cys
```

<210> SEQ ID NO 4
<211> LENGTH: 49
<212> TYPE: DNA
<213> ORGANISM: Artificial Sequence
<220> FEATURE:
<223> OTHER INFORMATION: Synthetic Construct

<400> SEQUENCE: 4
aacgacggta cccggggatc ggatccatgc ggctcgttgc ttccctaac          49

<210> SEQ ID NO 5
<211> LENGTH: 48
<212> TYPE: DNA
<213> ORGANISM: Artificial Sequence
<220> FEATURE:
<223> OTHER INFORMATION: Artificial Construct

<400> SEQUENCE: 5
ctaattacat gatgcggccc ttaattaatt agcaaccaag gtatatgg           48

<210> SEQ ID NO 6
<211> LENGTH: 20
<212> TYPE: DNA
<213> ORGANISM: Artificial Sequence
<220> FEATURE:
<223> OTHER INFORMATION: Artificial Construct

<400> SEQUENCE: 6
taggagttta gtgaacttgc                                          20

<210> SEQ ID NO 7
<211> LENGTH: 18
<212> TYPE: DNA
<213> ORGANISM: Artificial Sequence
<220> FEATURE:
<223> OTHER INFORMATION: Artificial Construct

<400> SEQUENCE: 7
ttcgagcgtc ccaaaacc                                            18

<210> SEQ ID NO 8
<211> LENGTH: 1851
<212> TYPE: DNA
<213> ORGANISM: Penicillium oxalicum
<220> FEATURE:
<221> NAME/KEY: CDS
<222> LOCATION: (1)..(1851)
<220> FEATURE:
<221> NAME/KEY: misc_signal
<222> LOCATION: (1)..(63)

<400> SEQUENCE: 8

```
atg cgt ctc act cta tta tca ggt gta gcc ggc gtt ctc tgc gca gga      48
Met Arg Leu Thr Leu Leu Ser Gly Val Ala Gly Val Leu Cys Ala Gly
1               5                   10                  15 cag ctg acg gcg gcg cgt cct gat ccc aag ggt ggg aat ctg acg ccg      96
Gln Leu Thr Ala Ala Arg Pro Asp Pro Lys Gly Gly Asn Leu Thr Pro
            20                  25                  30 ttc atc cac aaa gag ggc gag cgg tcg ctc caa ggc atc ttg gac aat     144
Phe Ile His Lys Glu Gly Glu Arg Ser Leu Gln Gly Ile Leu Asp Asn
        35                  40                  45 ctc ggt ggg cga ggt aag aaa aca ccc ggc act gcc gca ggg ttg ttt     192
Leu Gly Gly Arg Gly Lys Lys Thr Pro Gly Thr Ala Ala Gly Leu Phe
    50                  55                  60
```

```
att gcc agt cca aac aca gag aat cca aac tat tat tat aca tgg act      240
Ile Ala Ser Pro Asn Thr Glu Asn Pro Asn Tyr Tyr Tyr Thr Trp Thr
65              70                  75                  80 cgt gac tca gct ttg act gcc aag tgc ttg atc gac ctg ttc gaa gac      288
Arg Asp Ser Ala Leu Thr Ala Lys Cys Leu Ile Asp Leu Phe Glu Asp
                    85                  90                  95 tct cgg gca aag ttt cca att gac cgc aaa tac ttg gaa aca gga att      336
Ser Arg Ala Lys Phe Pro Ile Asp Arg Lys Tyr Leu Glu Thr Gly Ile
                100                 105                 110 cgg gac tac gtg tcg tcc caa gca atc ctc cag agt gtg tct aat cct      384
Arg Asp Tyr Val Ser Ser Gln Ala Ile Leu Gln Ser Val Ser Asn Pro
            115                 120                 125 tct gga acc ctg aag gat ggc tct ggt ctg ggt gaa ccc aag ttt gag      432
Ser Gly Thr Leu Lys Asp Gly Ser Gly Leu Gly Glu Pro Lys Phe Glu
130                 135                 140 att gac ctg aat ccc ttt tcg ggt gcc tgg ggt cgg cct cag cgg gat      480
Ile Asp Leu Asn Pro Phe Ser Gly Ala Trp Gly Arg Pro Gln Arg Asp
145                 150                 155                 160 ggc cca gcg ctg cga gcg acc gct atg atc acc tac gcc aac tac ctg      528
Gly Pro Ala Leu Arg Ala Thr Ala Met Ile Thr Tyr Ala Asn Tyr Leu
                165                 170                 175 ata tcc cat ggt cag aaa tcg gat gtg tca cag gtc atg tgg ccg att      576
Ile Ser His Gly Gln Lys Ser Asp Val Ser Gln Val Met Trp Pro Ile
            180                 185                 190 att gcc aat gat cta gca tat gtt ggt caa tac tgg aat aat acc gga      624
Ile Ala Asn Asp Leu Ala Tyr Val Gly Gln Tyr Trp Asn Asn Thr Gly
        195                 200                 205 ttt gac ctg tgg gaa gag gtg gat ggg tca agc ttt ttc acg att gcg      672
Phe Asp Leu Trp Glu Glu Val Asp Gly Ser Ser Phe Phe Thr Ile Ala
210                 215                 220 gtc cag cac cga gcc ctt gtt gaa ggc tcg caa ctg gcg aaa aag ctc      720
Val Gln His Arg Ala Leu Val Glu Gly Ser Gln Leu Ala Lys Lys Leu
225                 230                 235                 240 ggc aag tcc tgc gat gcc tgt gat tct cag cct ccc cag ata ttg tgt      768
Gly Lys Ser Cys Asp Ala Cys Asp Ser Gln Pro Pro Gln Ile Leu Cys
                245                 250                 255 ttc ctg cag agt ttc tgg aac gga aag tac atc acc tcc aac atc aac      816
Phe Leu Gln Ser Phe Trp Asn Gly Lys Tyr Ile Thr Ser Asn Ile Asn
            260                 265                 270 acg caa gca agc cgc tct ggt atc gac ctg gac tct gtc ctg gga agc      864
Thr Gln Ala Ser Arg Ser Gly Ile Asp Leu Asp Ser Val Leu Gly Ser
        275                 280                 285 att cat acc ttt gat ccc gaa gca gcc tgt gac gat gca act ttc cag      912
Ile His Thr Phe Asp Pro Glu Ala Ala Cys Asp Asp Ala Thr Phe Gln
290                 295                 300 cct tgt tct gcc cgc gct ctg gcg aac cac aag gtc tat gtg gat tcc      960
Pro Cys Ser Ala Arg Ala Leu Ala Asn His Lys Val Tyr Val Asp Ser
305                 310                 315                 320 ttc cgc tct atc tac aag att aat gcg ggt ctt gca gag gga tcg gct     1008
Phe Arg Ser Ile Tyr Lys Ile Asn Ala Gly Leu Ala Glu Gly Ser Ala
                325                 330                 335 gcc aac gtt ggc cgc tac ccc gag gat gtt tac caa gga ggc aat cca     1056
Ala Asn Val Gly Arg Tyr Pro Glu Asp Val Tyr Gln Gly Gly Asn Pro
            340                 345                 350 tgg tat ctc gcc acc cta ggc gca tct gaa ttg ctt tac gac gcc ttg     1104
Trp Tyr Leu Ala Thr Leu Gly Ala Ser Glu Leu Leu Tyr Asp Ala Leu
        355                 360                 365 tac cag tgg gac aga ctt ggc aaa ctt gaa gtc tcg gag acc tcg ttg     1152
Tyr Gln Trp Asp Arg Leu Gly Lys Leu Glu Val Ser Glu Thr Ser Leu
```

```
                    370                 375                 380
tca ttc ttc aaa gac ttt gac gcg acc gtg aaa att ggc tcg tac tcg    1200
Ser Phe Phe Lys Asp Phe Asp Ala Thr Val Lys Ile Gly Ser Tyr Ser
385                 390                 395                 400 agg aac agc aag acc tac aag aaa ttg acc cag tcc atc aag tcg tac    1248
Arg Asn Ser Lys Thr Tyr Lys Lys Leu Thr Gln Ser Ile Lys Ser Tyr
                405                 410                 415 gcg gac ggg ttc atc cag tta gtg cag cag tac act cct tct aat gga    1296
Ala Asp Gly Phe Ile Gln Leu Val Gln Gln Tyr Thr Pro Ser Asn Gly
            420                 425                 430 tct ctg gcc gag caa tac gat cgc aat acg gct gct cct ctc tct gca    1344
Ser Leu Ala Glu Gln Tyr Asp Arg Asn Thr Ala Ala Pro Leu Ser Ala
        435                 440                 445 aac gat ctg act tgg tca ttt gcc tct ttc ttg acg gct acg caa cgc    1392
Asn Asp Leu Thr Trp Ser Phe Ala Ser Phe Leu Thr Ala Thr Gln Arg
450                 455                 460 cgc gat gcc gtg gtt cct ccc tcc tgg ggc gca aag tcg gca aac aaa    1440
Arg Asp Ala Val Val Pro Pro Ser Trp Gly Ala Lys Ser Ala Asn Lys
465                 470                 475                 480 gtc cca acc act tgt tca gcc tcc cct gtt gtg ggt act tat aag gcg    1488
Val Pro Thr Thr Cys Ser Ala Ser Pro Val Val Gly Thr Tyr Lys Ala
                485                 490                 495 ccc acg gca act ttc tca tcc aag act aag tgc gtc ccc gct aaa gat    1536
Pro Thr Ala Thr Phe Ser Ser Lys Thr Lys Cys Val Pro Ala Lys Asp
            500                 505                 510 att gtg cct atc acg ttc tac ctg att gag aac act tac tat gga gag    1584
Ile Val Pro Ile Thr Phe Tyr Leu Ile Glu Asn Thr Tyr Tyr Gly Glu
        515                 520                 525 aac gtc ttc atg agt ggc aac att act gcg ctg ggt aac tgg gac gcc    1632
Asn Val Phe Met Ser Gly Asn Ile Thr Ala Leu Gly Asn Trp Asp Ala
530                 535                 540 aag aaa ggc ttc cca ctc acc gca aac ctc tac acg caa gat caa aac    1680
Lys Lys Gly Phe Pro Leu Thr Ala Asn Leu Tyr Thr Gln Asp Gln Asn
545                 550                 555                 560 ttg tgg ttc gcc agt gtc gag ttc atc cca gca ggc aca ccc ttt gag    1728
Leu Trp Phe Ala Ser Val Glu Phe Ile Pro Ala Gly Thr Pro Phe Glu
                565                 570                 575 tac aag tac tac aag gtc gag ccc aat ggc gat att act tgg gag aag    1776
Tyr Lys Tyr Tyr Lys Val Glu Pro Asn Gly Asp Ile Thr Trp Glu Lys
            580                 585                 590 ggt ccc aac cgg gtg ttc gtc gct ccc acg gga tgc cca gtt cag cct    1824
Gly Pro Asn Arg Val Phe Val Ala Pro Thr Gly Cys Pro Val Gln Pro
        595                 600                 605 cac tcc aac gac gtg tgg cag ttt tga                                1851
His Ser Asn Asp Val Trp Gln Phe
610                 615
```

<210> SEQ ID NO 9
<211> LENGTH: 616
<212> TYPE: PRT
<213> ORGANISM: Penicillium oxalicum

<400> SEQUENCE: 9

```
Met Arg Leu Thr Leu Leu Ser Gly Val Ala Gly Val Leu Cys Ala Gly
1               5                   10                  15

Gln Leu Thr Ala Ala Arg Pro Asp Pro Lys Gly Gly Asn Leu Thr Pro
            20                  25                  30

Phe Ile His Lys Glu Gly Glu Arg Ser Leu Gln Gly Ile Leu Asp Asn
        35                  40                  45
```

-continued

Leu Gly Gly Arg Gly Lys Lys Thr Pro Gly Thr Ala Ala Gly Leu Phe
    50              55                  60

Ile Ala Ser Pro Asn Thr Glu Asn Pro Asn Tyr Tyr Tyr Thr Trp Thr
65              70                  75                  80

Arg Asp Ser Ala Leu Thr Ala Lys Cys Leu Ile Asp Leu Phe Glu Asp
                85                  90                  95

Ser Arg Ala Lys Phe Pro Ile Asp Arg Lys Tyr Leu Glu Thr Gly Ile
            100                 105                 110

Arg Asp Tyr Val Ser Ser Gln Ala Ile Leu Gln Ser Val Ser Asn Pro
        115                 120                 125

Ser Gly Thr Leu Lys Asp Gly Ser Gly Leu Gly Glu Pro Lys Phe Glu
    130                 135                 140

Ile Asp Leu Asn Pro Phe Ser Gly Ala Trp Gly Arg Pro Gln Arg Asp
145             150                 155                 160

Gly Pro Ala Leu Arg Ala Thr Ala Met Ile Thr Tyr Ala Asn Tyr Leu
                165                 170                 175

Ile Ser His Gly Gln Lys Ser Asp Val Ser Gln Val Met Trp Pro Ile
            180                 185                 190

Ile Ala Asn Asp Leu Ala Tyr Val Gly Gln Tyr Trp Asn Asn Thr Gly
        195                 200                 205

Phe Asp Leu Trp Glu Glu Val Asp Gly Ser Ser Phe Phe Thr Ile Ala
    210                 215                 220

Val Gln His Arg Ala Leu Val Glu Gly Ser Gln Leu Ala Lys Lys Leu
225             230                 235                 240

Gly Lys Ser Cys Asp Ala Cys Asp Ser Gln Pro Gln Ile Leu Cys
                245                 250                 255

Phe Leu Gln Ser Phe Trp Asn Gly Lys Tyr Ile Thr Ser Asn Ile Asn
            260                 265                 270

Thr Gln Ala Ser Arg Ser Gly Ile Asp Leu Asp Ser Val Leu Gly Ser
        275                 280                 285

Ile His Thr Phe Asp Pro Glu Ala Ala Cys Asp Asp Ala Thr Phe Gln
    290                 295                 300

Pro Cys Ser Ala Arg Ala Leu Ala Asn His Lys Val Tyr Val Asp Ser
305             310                 315                 320

Phe Arg Ser Ile Tyr Lys Ile Asn Ala Gly Leu Ala Glu Gly Ser Ala
                325                 330                 335

Ala Asn Val Gly Arg Tyr Pro Glu Asp Val Tyr Gln Gly Gly Asn Pro
            340                 345                 350

Trp Tyr Leu Ala Thr Leu Gly Ala Ser Glu Leu Leu Tyr Asp Ala Leu
        355                 360                 365

Tyr Gln Trp Asp Arg Leu Gly Lys Leu Glu Val Ser Glu Thr Ser Leu
    370                 375                 380

Ser Phe Phe Lys Asp Phe Asp Ala Thr Val Lys Ile Gly Ser Tyr Ser
385             390                 395                 400

Arg Asn Ser Lys Thr Tyr Lys Lys Leu Thr Gln Ser Ile Lys Ser Tyr
                405                 410                 415

Ala Asp Gly Phe Ile Gln Leu Val Gln Gln Tyr Thr Pro Ser Asn Gly
            420                 425                 430

Ser Leu Ala Glu Gln Tyr Asp Arg Asn Thr Ala Ala Pro Leu Ser Ala
        435                 440                 445

Asn Asp Leu Thr Trp Ser Phe Ala Ser Phe Leu Thr Ala Thr Gln Arg
    450                 455                 460

Arg Asp Ala Val Val Pro Pro Ser Trp Gly Ala Lys Ser Ala Asn Lys

```
                        465                 470                 475                 480
Val Pro Thr Thr Cys Ser Ala Ser Pro Val Val Gly Thr Tyr Lys Ala
                            485                 490                 495

Pro Thr Ala Thr Phe Ser Ser Lys Thr Lys Cys Val Pro Ala Lys Asp
                500                 505                 510

Ile Val Pro Ile Thr Phe Tyr Leu Ile Glu Asn Thr Tyr Tyr Gly Glu
                515                 520                 525

Asn Val Phe Met Ser Gly Asn Ile Thr Ala Leu Gly Asn Trp Asp Ala
            530                 535                 540

Lys Lys Gly Phe Pro Leu Thr Ala Asn Leu Tyr Thr Gln Asp Gln Asn
545                 550                 555                 560

Leu Trp Phe Ala Ser Val Glu Phe Ile Pro Ala Gly Thr Pro Phe Glu
                565                 570                 575

Tyr Lys Tyr Tyr Lys Val Glu Pro Asn Gly Asp Ile Thr Trp Glu Lys
                580                 585                 590

Gly Pro Asn Arg Val Phe Val Ala Pro Thr Gly Cys Pro Val Gln Pro
            595                 600                 605

His Ser Asn Asp Val Trp Gln Phe
610                 615

<210> SEQ ID NO 10
<211> LENGTH: 4014
<212> TYPE: DNA
<213> ORGANISM: Thermococcus hydrothermalis
<220> FEATURE:
<221> NAME/KEY: CDS
<222> LOCATION: (1)..(4011)
<220> FEATURE:
<221> NAME/KEY: misc_signal
<222> LOCATION: (1)..(81)
<220> FEATURE:
<221> NAME/KEY: mat_peptide
<222> LOCATION: (82)..(4014)

<400> SEQUENCE: 10 atg agg cgg gtg gtt gcc ctc ttc att gca att ttg atg ctt gga agc    48
Met Arg Arg Val Val Ala Leu Phe Ile Ala Ile Leu Met Leu Gly Ser
        -25                 -20                 -15 atc gtt gga gcg aac gtt aag agc gtt ggc gcg gcg gag ccg aag ccg    96
Ile Val Gly Ala Asn Val Lys Ser Val Gly Ala Ala Glu Pro Lys Pro
    -10                 -5              -1  1                   5 ctc aac gtc ata ata gtc tgg cac cag cac cag ccc tac tac tac gac   144
Leu Asn Val Ile Ile Val Trp His Gln His Gln Pro Tyr Tyr Tyr Asp
                10                  15                  20 cct gtc cag gac gtc tac acc agg ccc tgg gtc agg ctc cac gcg gcg   192
Pro Val Gln Asp Val Tyr Thr Arg Pro Trp Val Arg Leu His Ala Ala
            25                  30                  35 aac aac tac tgg aag atg gcc cac tac ctg agc cag tac ccg gag gtt   240
Asn Asn Tyr Trp Lys Met Ala His Tyr Leu Ser Gln Tyr Pro Glu Val
        40                  45                  50 cac gcc acc att gac ctc tcg ggt tcg ctg ata gcc cag ctt gcc gac   288
His Ala Thr Ile Asp Leu Ser Gly Ser Leu Ile Ala Gln Leu Ala Asp
55                  60                  65 tac atg aac ggc aag aag gac acc tac cag ata atc acc gag aag ata   336
Tyr Met Asn Gly Lys Lys Asp Thr Tyr Gln Ile Ile Thr Glu Lys Ile
70                  75                  80                  85 gcc aac ggg gaa ccc ctc acc gtc gac gag aag tgg ttc atg ctc cag   384
Ala Asn Gly Glu Pro Leu Thr Val Asp Glu Lys Trp Phe Met Leu Gln
                90                  95                 100 gca ccg gga ggg ttc ttc gac aac acc atc ccc tgg aac ggt gaa ccg   432
```

```
Ala Pro Gly Gly Phe Phe Asp Asn Thr Ile Pro Trp Asn Gly Glu Pro
                    105                 110                 115 ata acc gac ccc aac ggc aac ccg ata agg gac ttc tgg gac cgc tac       480
Ile Thr Asp Pro Asn Gly Asn Pro Ile Arg Asp Phe Trp Asp Arg Tyr
                120                 125                 130 acg gag ctg aag aac aag atg ctc agc gca aag gcc aag tac gca aac       528
Thr Glu Leu Lys Asn Lys Met Leu Ser Ala Lys Ala Lys Tyr Ala Asn
135                 140                 145 ttc gtg act gag agc cag aag gtc gct gtg acg aac gag ttc aca gag       576
Phe Val Thr Glu Ser Gln Lys Val Ala Val Thr Asn Glu Phe Thr Glu
150                 155                 160                 165 cag gac tac ata gac cta gcg gtt ctc ttc aat ctc gct tgg att gac       624
Gln Asp Tyr Ile Asp Leu Ala Val Leu Phe Asn Leu Ala Trp Ile Asp
                170                 175                 180 tac aat tac atc acg agc acg ccg gag ttc aag gcc ctc tac gac aag       672
Tyr Asn Tyr Ile Thr Ser Thr Pro Glu Phe Lys Ala Leu Tyr Asp Lys
                185                 190                 195 gtt gac gag ggc ggc tat aca agg gcg gac gtc aaa acc gtt ctc gac       720
Val Asp Glu Gly Gly Tyr Thr Arg Ala Asp Val Lys Thr Val Leu Asp
                200                 205                 210 gcc cag atc tgg ctt ctc aac cac acc ttc gag gag cac gag aag ata       768
Ala Gln Ile Trp Leu Leu Asn His Thr Phe Glu Glu His Glu Lys Ile
215                 220                 225 aac ctc ctc ctc gga aac ggc aac gtc gag gtc acg gtc gtt ccc tac       816
Asn Leu Leu Leu Gly Asn Gly Asn Val Glu Val Thr Val Val Pro Tyr
230                 235                 240                 245 gcc cac ccg ata ggc ccg ata ctc aac gac ttc ggc tgg gac agc gac       864
Ala His Pro Ile Gly Pro Ile Leu Asn Asp Phe Gly Trp Asp Ser Asp
                250                 255                 260 ttc aac gac cag gtc aag aag gcc gac gaa ctg tac aag ccg tac ctc       912
Phe Asn Asp Gln Val Lys Lys Ala Asp Glu Leu Tyr Lys Pro Tyr Leu
                265                 270                 275 ggc ggc ggc acc gcg gtt cca aaa ggc gga tgg gcg gct gag agc gcc       960
Gly Gly Gly Thr Ala Val Pro Lys Gly Gly Trp Ala Ala Glu Ser Ala
                280                 285                 290 ctc aac gac aaa act ctg gag atc ctc gcc gag aac ggc tgg gag tgg      1008
Leu Asn Asp Lys Thr Leu Glu Ile Leu Ala Glu Asn Gly Trp Glu Trp
295                 300                 305 gtc atg acc gac cag atg gtt ctc gga aag ctc ggc att gag gga acc      1056
Val Met Thr Asp Gln Met Val Leu Gly Lys Leu Gly Ile Glu Gly Thr
310                 315                 320                 325 gtc gag aac tac cac aag ccc tgg gtg gcc gag ttc aac gga aag aag      1104
Val Glu Asn Tyr His Lys Pro Trp Val Ala Glu Phe Asn Gly Lys Lys
                330                 335                 340 ata tac ctc ttc cca aga aat cac gat cta agt gac aga gtt ggc ttt      1152
Ile Tyr Leu Phe Pro Arg Asn His Asp Leu Ser Asp Arg Val Gly Phe
                345                 350                 355 acc tac agc gga atg aac cag cag cag gcc gtt gag gac ttc gtc aac      1200
Thr Tyr Ser Gly Met Asn Gln Gln Gln Ala Val Glu Asp Phe Val Asn
                360                 365                 370 gag ctc ctc aag ctc cag aag cag aac tac gat ggc tcg ctg gtt tac      1248
Glu Leu Leu Lys Leu Gln Lys Gln Asn Tyr Asp Gly Ser Leu Val Tyr
375                 380                 385 gtg gtc acg ctc gac ggc gag aac ccc gtg gag aac tac ccc tac gac      1296
Val Val Thr Leu Asp Gly Glu Asn Pro Val Glu Asn Tyr Pro Tyr Asp
390                 395                 400                 405 ggg gag ctc ttc ctc acc gaa ctc tac aag aag ctg acc gaa ctc cag      1344
Gly Glu Leu Phe Leu Thr Glu Leu Tyr Lys Lys Leu Thr Glu Leu Gln
                410                 415                 420
```

| | | |
|---|---|---|
| gag cag ggt ctc ata aga acc ctc acc ccg agc gag tac atc cag ctc<br>Glu Gln Gly Leu Ile Arg Thr Leu Thr Pro Ser Glu Tyr Ile Gln Leu<br>425 430 435 | 1392 | |
| tac ggc gac aag gcc aac aag ctc aca cct cgg atg atg gag cgc ctt<br>Tyr Gly Asp Lys Ala Asn Lys Leu Thr Pro Arg Met Met Glu Arg Leu<br>440 445 450 | 1440 | |
| gac ctc acc gga gac aac gtt aac gcc ctc ctc aag gcc cag agc ctc<br>Asp Leu Thr Gly Asp Asn Val Asn Ala Leu Leu Lys Ala Gln Ser Leu<br>455 460 465 | 1488 | |
| ggc gaa ctc tac gac atg acc ggc gtt aag gag gag atg cag tgg ccc<br>Gly Glu Leu Tyr Asp Met Thr Gly Val Lys Glu Glu Met Gln Trp Pro<br>470 475 480 485 | 1536 | |
| gag agc agc tgg ata gac gga acc ctc tcc acg tgg ata ggc gag ccc<br>Glu Ser Ser Trp Ile Asp Gly Thr Leu Ser Thr Trp Ile Gly Glu Pro<br>490 495 500 | 1584 | |
| cag gag aac tac ggc tgg tac tgg ctc tac atg gcc agg aag gcc ctt<br>Gln Glu Asn Tyr Gly Trp Tyr Trp Leu Tyr Met Ala Arg Lys Ala Leu<br>505 510 515 | 1632 | |
| atg gag aac aag gat aaa atg agc cag gcg gac tgg gag aag gcc tac<br>Met Glu Asn Lys Asp Lys Met Ser Gln Ala Asp Trp Glu Lys Ala Tyr<br>520 525 530 | 1680 | |
| gag tac ctg ctc cgc gcc gag gca agc gac tgg ttc tgg tgg tac gga<br>Glu Tyr Leu Leu Arg Ala Glu Ala Ser Asp Trp Phe Trp Trp Tyr Gly<br>535 540 545 | 1728 | |
| agc gac cag gac agc ggc cag gac tac acc ttc gac cgc tac ctg aag<br>Ser Asp Gln Asp Ser Gly Gln Asp Tyr Thr Phe Asp Arg Tyr Leu Lys<br>550 555 560 565 | 1776 | |
| acc tac ctc tac gag atg tac aag ctg gca gga gtc gag ccg ccg agc<br>Thr Tyr Leu Tyr Glu Met Tyr Lys Leu Ala Gly Val Glu Pro Pro Ser<br>570 575 580 | 1824 | |
| tac ctc ttc ggc aac tac ttc ccg gac gga gag ccc tac acc acg agg<br>Tyr Leu Phe Gly Asn Tyr Phe Pro Asp Gly Glu Pro Tyr Thr Thr Arg<br>585 590 595 | 1872 | |
| ggc ctg gtc gga ctc aag gac ggc gag atg aag aac ttc tcc agc atg<br>Gly Leu Val Gly Leu Lys Asp Gly Glu Met Lys Asn Phe Ser Ser Met<br>600 605 610 | 1920 | |
| tcc ccg ctg gca aag ggc gtg agc gtc tat ttc gac ggc gag ggg ata<br>Ser Pro Leu Ala Lys Gly Val Ser Val Tyr Phe Asp Gly Glu Gly Ile<br>615 620 625 | 1968 | |
| cac ttc ata gtg aaa ggg aac ctg gac agg ttc gag gtg agc atc tgg<br>His Phe Ile Val Lys Gly Asn Leu Asp Arg Phe Glu Val Ser Ile Trp<br>630 635 640 645 | 2016 | |
| gag aag gat gag cgc gtt ggc aac acg ttc acc cgc ctc caa gag aag<br>Glu Lys Asp Glu Arg Val Gly Asn Thr Phe Thr Arg Leu Gln Glu Lys<br>650 655 660 | 2064 | |
| ccg gac gag ttg agc tat ttc atg ttc cca ttc tca agg gac agc gtt<br>Pro Asp Glu Leu Ser Tyr Phe Met Phe Pro Phe Ser Arg Asp Ser Val<br>665 670 675 | 2112 | |
| ggt ctc ctc ata acc aag cac gtc gtg tac gag aac gga aag gcc gag<br>Gly Leu Leu Ile Thr Lys His Val Val Tyr Glu Asn Gly Lys Ala Glu<br>680 685 690 | 2160 | |
| ata tac ggc gcc acc gac tac gag aag agc gag aag ctt ggg gaa gcc<br>Ile Tyr Gly Ala Thr Asp Tyr Glu Lys Ser Glu Lys Leu Gly Glu Ala<br>695 700 705 | 2208 | |
| acc gtc aag aac acg agc gaa gga atc gaa gtc gtc ctt ccc ttt gac<br>Thr Val Lys Asn Thr Ser Glu Gly Ile Glu Val Val Leu Pro Phe Asp<br>710 715 720 725 | 2256 | |
| tac ata gaa aac ccc tcc gac ttc tac ttc gct gtc tcg acg gtc aaa<br>Tyr Ile Glu Asn Pro Ser Asp Phe Tyr Phe Ala Val Ser Thr Val Lys<br>730 735 740 | 2304 | |

```
                                                    -continued gat gga gac ctt gag gtg ata agc act cct gtg gag ctc aag ctc ccg   2352
Asp Gly Asp Leu Glu Val Ile Ser Thr Pro Val Glu Leu Lys Leu Pro
            745                 750                 755 acc gag gtc aag gga gtc gtc ata gcc gat ata acc gac cca gaa ggc   2400
Thr Glu Val Lys Gly Val Val Ile Ala Asp Ile Thr Asp Pro Glu Gly
        760                 765                 770 gac gac cat ggg ccc gga aac tac act tat ccc acg gac aag gtc ttc   2448
Asp Asp His Gly Pro Gly Asn Tyr Thr Tyr Pro Thr Asp Lys Val Phe
    775                 780                 785 aag cca ggt gtt ttc gac ctc ctc cgc ttc agg atg ctc gaa cag acg   2496
Lys Pro Gly Val Phe Asp Leu Leu Arg Phe Arg Met Leu Glu Gln Thr
790                 795                 800                 805 gag agc tac gtc atg gag ttc tac ttc aag gac cta ggt ggt aac ccg   2544
Glu Ser Tyr Val Met Glu Phe Tyr Phe Lys Asp Leu Gly Gly Asn Pro
                810                 815                 820 tgg aac gga ccc aac ggc ttc agc ctc cag ata atc gag gtc tac ctc   2592
Trp Asn Gly Pro Asn Gly Phe Ser Leu Gln Ile Ile Glu Val Tyr Leu
            825                 830                 835 gac ttc aag gac ggt gga aac agt tcg gcc att aag atg ttc ccc gac   2640
Asp Phe Lys Asp Gly Gly Asn Ser Ser Ala Ile Lys Met Phe Pro Asp
        840                 845                 850 gga ccg gga gcc aac gtc aac ctc gac ccc gag cat cca tgg gac gtt   2688
Gly Pro Gly Ala Asn Val Asn Leu Asp Pro Glu His Pro Trp Asp Val
    855                 860                 865 gcc ttc agg ata gcg ggc tgg gac tac gga aac ctc atc atc ctg ccg   2736
Ala Phe Arg Ile Ala Gly Trp Asp Tyr Gly Asn Leu Ile Ile Leu Pro
870                 875                 880                 885 aac gga acg gcc atc cag ggc gag atg cag att tcc gca gat ccg gtt   2784
Asn Gly Thr Ala Ile Gln Gly Glu Met Gln Ile Ser Ala Asp Pro Val
                890                 895                 900 aag aac gcc ata ata gtc aag gtt cca aag aag tac atc gcc ata aac   2832
Lys Asn Ala Ile Ile Val Lys Val Pro Lys Lys Tyr Ile Ala Ile Asn
            905                 910                 915 gag gac tac ggc ctc tgg gga gac gtc ctc gtc ggc tcg cag gac ggc   2880
Glu Asp Tyr Gly Leu Trp Gly Asp Val Leu Val Gly Ser Gln Asp Gly
        920                 925                 930 tac ggc ccg gac aag tgg aga acg gcg gca gtg gat gcg gag cag tgg   2928
Tyr Gly Pro Asp Lys Trp Arg Thr Ala Ala Val Asp Ala Glu Gln Trp
    935                 940                 945 aag ctt gga ggt gcg gac ccg cag gca gtc ata aac ggc gtg gcc ccg   2976
Lys Leu Gly Gly Ala Asp Pro Gln Ala Val Ile Asn Gly Val Ala Pro
950                 955                 960                 965 cgc gtc att gat gag ctg gtt ccg cag ggc ttt gaa ccg acc cag gag   3024
Arg Val Ile Asp Glu Leu Val Pro Gln Gly Phe Glu Pro Thr Gln Glu
                970                 975                 980 gag cag ctg agc agc tac gat gca aac gac atg aag ctc gcc act gtc   3072
Glu Gln Leu Ser Ser Tyr Asp Ala Asn Asp Met Lys Leu Ala Thr Val
            985                 990                 995 aag gcg ctg cta ctc ctc aag cag ggc atc gtt gtg acc gac ccg        3117
Lys Ala Leu Leu Leu Leu Lys Gln Gly Ile Val Val Thr Asp Pro
            1000                1005                1010 gag gga gac gac cac ggg ccg gga acg tac acc tat ccg acg gac        3162
Glu Gly Asp Asp His Gly Pro Gly Thr Tyr Thr Tyr Pro Thr Asp
            1015                1020                1025 aaa gtt ttc aag ccc ggt gtt ttc gac ctc ctc aag ttc aag gtg        3207
Lys Val Phe Lys Pro Gly Val Phe Asp Leu Leu Lys Phe Lys Val
            1030                1035                1040 acc gag gga agc gac gac tgg acg ctg gag ttc cac ttc aaa gac        3252
Thr Glu Gly Ser Asp Asp Trp Thr Leu Glu Phe His Phe Lys Asp
```

```
                    1045                1050                1055
ctc ggt gga aac ccg tgg aac ggg ccg aac ggc ttc agc ctg cag    3297
Leu Gly Gly Asn Pro Trp Asn Gly Pro Asn Gly Phe Ser Leu Gln
            1060                1065                1070 ata atc gag gta tac ttc gac ttc aag gag ggg aac gtc tcg        3342
Ile Ile Glu Val Tyr Phe Asp Phe Lys Glu Gly Asn Val Ser
        1075                1080                1085 gcc att aag atg ttc ccg gat ggg ccc gga agc aac gtc cgt ctt    3387
Ala Ile Lys Met Phe Pro Asp Gly Pro Gly Ser Asn Val Arg Leu
            1090                1095                1100 gat cca aat cac cca tgg gac ctg gcg ctt agg ata gcc ggc tgg    3432
Asp Pro Asn His Pro Trp Asp Leu Ala Leu Arg Ile Ala Gly Trp
            1105                1110                1115 gac tac gga aac ctg ata att ctg ccc gac gga acc gcc tac caa    3477
Asp Tyr Gly Asn Leu Ile Ile Leu Pro Asp Gly Thr Ala Tyr Gln
            1120                1125                1130 ggc gag atg cag att tcc gca gat ccg gtt aag aac gcc ata ata    3522
Gly Glu Met Gln Ile Ser Ala Asp Pro Val Lys Asn Ala Ile Ile
            1135                1140                1145 gtc aag gtt cca aag aag tac ctg aac ata tcc gac tac gga ctc    3567
Val Lys Val Pro Lys Lys Tyr Leu Asn Ile Ser Asp Tyr Gly Leu
            1150                1155                1160 tac acc gcc gtc atc gtg ggt tcc caa gac ggg tac ggc ccg gac    3612
Tyr Thr Ala Val Ile Val Gly Ser Gln Asp Gly Tyr Gly Pro Asp
            1165                1170                1175 aag tgg agg ccc gtg gcc gct gag gcc gag cag tgg aag ctc gga    3657
Lys Trp Arg Pro Val Ala Ala Glu Ala Glu Gln Trp Lys Leu Gly
            1180                1185                1190 ggc gca gac ccc cag gcg gtc ata gac aac ctc gta cca agg gtc    3702
Gly Ala Asp Pro Gln Ala Val Ile Asp Asn Leu Val Pro Arg Val
            1195                1200                1205 gtt gat gaa ctc gtg ccg gag ggc ttc aag cca acg cag gag gag    3747
Val Asp Glu Leu Val Pro Glu Gly Phe Lys Pro Thr Gln Glu Glu
            1210                1215                1220 cag ctg agc agc tac gac ctt gag aag aag acc ctg gcg acg gtg    3792
Gln Leu Ser Ser Tyr Asp Leu Glu Lys Lys Thr Leu Ala Thr Val
            1225                1230                1235 ctc atg gta ccg ctc gtc aat ggg act ggc ggc gag gaa cca acg    3837
Leu Met Val Pro Leu Val Asn Gly Thr Gly Gly Glu Glu Pro Thr
            1240                1245                1250 ccg acg gag agc cca acg gaa acg acg aca acc aca ccc agc gaa    3882
Pro Thr Glu Ser Pro Thr Glu Thr Thr Thr Thr Thr Pro Ser Glu
            1255                1260                1265 aca acc acc aca act tca acg acc acc ggc cca agc tca acg acc    3927
Thr Thr Thr Thr Thr Ser Thr Thr Thr Gly Pro Ser Ser Thr Thr
            1270                1275                1280 acc agc aca ccc ggc gga gga atc tgc ggc cca ggc att ata gcg    3972
Thr Ser Thr Pro Gly Gly Gly Ile Cys Gly Pro Gly Ile Ile Ala
            1285                1290                1295 ggc ctg gcc ctg ata ccg ctc ctc ctc aag agg agg aac tga        4014
Gly Leu Ala Leu Ile Pro Leu Leu Leu Lys Arg Arg Asn
            1300                1305                1310

<210> SEQ ID NO 11
<211> LENGTH: 1337
<212> TYPE: PRT
<213> ORGANISM: Thermococcus hydrothermalis

<400> SEQUENCE: 11

Met Arg Arg Val Val Ala Leu Phe Ile Ala Ile Leu Met Leu Gly Ser
```

```
                -25                 -20                 -15
Ile Val Gly Ala Asn Val Lys Ser Val Gly Ala Ala Glu Pro Lys Pro
    -10                 -5                  -1  1                   5

Leu Asn Val Ile Ile Val Trp His Gln His Gln Pro Tyr Tyr Tyr Asp
                    10                  15                  20

Pro Val Gln Asp Val Tyr Thr Arg Pro Trp Val Arg Leu His Ala Ala
                25                  30                  35

Asn Asn Tyr Trp Lys Met Ala His Tyr Leu Ser Gln Tyr Pro Glu Val
            40                  45                  50

His Ala Thr Ile Asp Leu Ser Gly Ser Leu Ile Ala Gln Leu Ala Asp
    55                  60                  65

Tyr Met Asn Gly Lys Lys Asp Thr Tyr Gln Ile Ile Thr Glu Lys Ile
70                  75                  80                  85

Ala Asn Gly Glu Pro Leu Thr Val Asp Glu Lys Trp Phe Met Leu Gln
                90                  95                  100

Ala Pro Gly Gly Phe Phe Asp Asn Thr Ile Pro Trp Asn Gly Glu Pro
            105                 110                 115

Ile Thr Asp Pro Asn Gly Asn Pro Ile Arg Asp Phe Trp Asp Arg Tyr
        120                 125                 130

Thr Glu Leu Lys Asn Lys Met Leu Ser Ala Lys Ala Lys Tyr Ala Asn
    135                 140                 145

Phe Val Thr Glu Ser Gln Lys Val Ala Val Thr Asn Glu Phe Thr Glu
150                 155                 160                 165

Gln Asp Tyr Ile Asp Leu Ala Val Leu Phe Asn Leu Ala Trp Ile Asp
            170                 175                 180

Tyr Asn Tyr Ile Thr Ser Thr Pro Glu Phe Lys Ala Leu Tyr Asp Lys
        185                 190                 195

Val Asp Glu Gly Gly Tyr Thr Arg Ala Asp Val Lys Thr Val Leu Asp
    200                 205                 210

Ala Gln Ile Trp Leu Leu Asn His Thr Phe Glu Glu His Glu Lys Ile
    215                 220                 225

Asn Leu Leu Leu Gly Asn Gly Asn Val Glu Val Thr Val Val Pro Tyr
230                 235                 240                 245

Ala His Pro Ile Gly Pro Ile Leu Asn Asp Phe Gly Trp Asp Ser Asp
            250                 255                 260

Phe Asn Asp Gln Val Lys Lys Ala Asp Glu Leu Tyr Lys Pro Tyr Leu
        265                 270                 275

Gly Gly Gly Thr Ala Val Pro Lys Gly Gly Trp Ala Ala Glu Ser Ala
    280                 285                 290

Leu Asn Asp Lys Thr Leu Glu Ile Leu Ala Glu Asn Gly Trp Glu Trp
    295                 300                 305

Val Met Thr Asp Gln Met Val Leu Gly Lys Leu Gly Ile Glu Gly Thr
310                 315                 320                 325

Val Glu Asn Tyr His Lys Pro Trp Val Ala Glu Phe Asn Gly Lys Lys
            330                 335                 340

Ile Tyr Leu Phe Pro Arg Asn His Asp Leu Ser Asp Arg Val Gly Phe
        345                 350                 355

Thr Tyr Ser Gly Met Asn Gln Gln Gln Ala Val Glu Asp Phe Val Asn
    360                 365                 370

Glu Leu Leu Lys Leu Gln Lys Gln Asn Tyr Asp Gly Ser Leu Val Tyr
    375                 380                 385

Val Val Thr Leu Asp Gly Glu Asn Pro Val Glu Asn Tyr Pro Tyr Asp
390                 395                 400                 405
```

```
Gly Glu Leu Phe Leu Thr Glu Leu Tyr Lys Lys Leu Thr Glu Leu Gln
                410                 415                 420

Glu Gln Gly Leu Ile Arg Thr Leu Thr Pro Ser Glu Tyr Ile Gln Leu
            425                 430                 435

Tyr Gly Asp Lys Ala Asn Lys Leu Thr Pro Arg Met Met Glu Arg Leu
        440                 445                 450

Asp Leu Thr Gly Asp Asn Val Asn Ala Leu Leu Lys Ala Gln Ser Leu
    455                 460                 465

Gly Glu Leu Tyr Asp Met Thr Gly Val Lys Glu Met Gln Trp Pro
470                 475                 480                 485

Glu Ser Ser Trp Ile Asp Gly Thr Leu Ser Thr Trp Ile Gly Glu Pro
                490                 495                 500

Gln Glu Asn Tyr Gly Trp Tyr Trp Leu Tyr Met Ala Arg Lys Ala Leu
            505                 510                 515

Met Glu Asn Lys Asp Lys Met Ser Gln Ala Asp Trp Glu Lys Ala Tyr
        520                 525                 530

Glu Tyr Leu Leu Arg Ala Glu Ala Ser Asp Trp Phe Trp Trp Tyr Gly
    535                 540                 545

Ser Asp Gln Asp Ser Gly Gln Asp Tyr Thr Phe Asp Arg Tyr Leu Lys
550                 555                 560                 565

Thr Tyr Leu Tyr Glu Met Tyr Lys Leu Ala Gly Val Glu Pro Pro Ser
                570                 575                 580

Tyr Leu Phe Gly Asn Tyr Phe Pro Asp Gly Glu Pro Tyr Thr Thr Arg
            585                 590                 595

Gly Leu Val Gly Leu Lys Asp Gly Glu Met Lys Asn Phe Ser Ser Met
        600                 605                 610

Ser Pro Leu Ala Lys Gly Val Ser Val Tyr Phe Asp Gly Glu Gly Ile
    615                 620                 625

His Phe Ile Val Lys Gly Asn Leu Asp Arg Phe Glu Val Ser Ile Trp
630                 635                 640                 645

Glu Lys Asp Glu Arg Val Gly Asn Thr Phe Thr Arg Leu Gln Glu Lys
                650                 655                 660

Pro Asp Glu Leu Ser Tyr Phe Met Phe Pro Phe Ser Arg Asp Ser Val
            665                 670                 675

Gly Leu Leu Ile Thr Lys His Val Val Tyr Glu Asn Gly Lys Ala Glu
        680                 685                 690

Ile Tyr Gly Ala Thr Asp Tyr Glu Lys Ser Glu Lys Leu Gly Glu Ala
    695                 700                 705

Thr Val Lys Asn Thr Ser Glu Gly Ile Glu Val Val Leu Pro Phe Asp
710                 715                 720                 725

Tyr Ile Glu Asn Pro Ser Asp Phe Tyr Phe Ala Val Ser Thr Val Lys
                730                 735                 740

Asp Gly Asp Leu Glu Val Ile Ser Thr Pro Val Glu Leu Lys Leu Pro
            745                 750                 755

Thr Glu Val Lys Gly Val Val Ile Ala Asp Ile Thr Asp Pro Glu Gly
        760                 765                 770

Asp Asp His Gly Pro Gly Asn Tyr Thr Tyr Pro Thr Asp Lys Val Phe
    775                 780                 785

Lys Pro Gly Val Phe Asp Leu Leu Arg Phe Arg Met Leu Glu Gln Thr
790                 795                 800                 805

Glu Ser Tyr Val Met Glu Phe Tyr Phe Lys Asp Leu Gly Gly Asn Pro
                810                 815                 820
```

Trp Asn Gly Pro Asn Gly Phe Ser Leu Gln Ile Ile Glu Val Tyr Leu
                825                 830                 835

Asp Phe Lys Asp Gly Gly Asn Ser Ser Ala Ile Lys Met Phe Pro Asp
        840                 845                 850

Gly Pro Gly Ala Asn Val Asn Leu Asp Pro Glu His Pro Trp Asp Val
    855                 860                 865

Ala Phe Arg Ile Ala Gly Trp Asp Tyr Gly Asn Leu Ile Ile Leu Pro
870                 875                 880                 885

Asn Gly Thr Ala Ile Gln Gly Glu Met Gln Ile Ser Ala Asp Pro Val
            890                 895                 900

Lys Asn Ala Ile Ile Val Lys Val Pro Lys Lys Tyr Ile Ala Ile Asn
            905                 910                 915

Glu Asp Tyr Gly Leu Trp Gly Asp Val Leu Val Gly Ser Gln Asp Gly
            920                 925                 930

Tyr Gly Pro Asp Lys Trp Arg Thr Ala Val Asp Ala Glu Gln Trp
        935                 940                 945

Lys Leu Gly Gly Ala Asp Pro Gln Ala Val Ile Asn Gly Val Ala Pro
950                 955                 960                 965

Arg Val Ile Asp Glu Leu Val Pro Gln Gly Phe Glu Pro Thr Gln Glu
            970                 975                 980

Glu Gln Leu Ser Ser Tyr Asp Ala Asn Asp Met Lys Leu Ala Thr Val
            985                 990                 995

Lys Ala Leu Leu Leu Leu Lys Gln Gly Ile Val Val Thr Asp Pro
        1000                1005                1010

Glu Gly Asp Asp His Gly Pro Gly Thr Tyr Thr Tyr Pro Thr Asp
        1015                1020                1025

Lys Val Phe Lys Pro Gly Val Phe Asp Leu Leu Lys Phe Lys Val
        1030                1035                1040

Thr Glu Gly Ser Asp Asp Trp Thr Leu Glu Phe His Phe Lys Asp
        1045                1050                1055

Leu Gly Gly Asn Pro Trp Asn Gly Pro Asn Gly Phe Ser Leu Gln
        1060                1065                1070

Ile Ile Glu Val Tyr Phe Asp Phe Lys Glu Gly Gly Asn Val Ser
        1075                1080                1085

Ala Ile Lys Met Phe Pro Asp Gly Pro Gly Ser Asn Val Arg Leu
        1090                1095                1100

Asp Pro Asn His Pro Trp Asp Leu Ala Leu Arg Ile Ala Gly Trp
        1105                1110                1115

Asp Tyr Gly Asn Leu Ile Ile Leu Pro Asp Gly Thr Ala Tyr Gln
        1120                1125                1130

Gly Glu Met Gln Ile Ser Ala Asp Pro Val Lys Asn Ala Ile Ile
        1135                1140                1145

Val Lys Val Pro Lys Lys Tyr Leu Asn Ile Ser Asp Tyr Gly Leu
        1150                1155                1160

Tyr Thr Ala Val Ile Val Gly Ser Gln Asp Gly Tyr Gly Pro Asp
        1165                1170                1175

Lys Trp Arg Pro Val Ala Ala Glu Ala Glu Gln Trp Lys Leu Gly
        1180                1185                1190

Gly Ala Asp Pro Gln Ala Val Ile Asp Asn Leu Val Pro Arg Val
        1195                1200                1205

Val Asp Glu Leu Val Pro Glu Gly Phe Lys Pro Thr Gln Glu Glu
        1210                1215                1220

Gln Leu Ser Ser Tyr Asp Leu Glu Lys Lys Thr Leu Ala Thr Val

```
                    1225                1230                1235

Leu Met Val Pro Leu Val Asn Gly Thr Gly Gly Glu Glu Pro Thr
        1240                1245                1250

Pro Thr Glu Ser Pro Thr Glu Thr Thr Thr Thr Pro Ser Glu
        1255                1260                1265

Thr Thr Thr Thr Thr Ser Thr Thr Thr Gly Pro Ser Ser Thr Thr
        1270                1275                1280

Thr Ser Thr Pro Gly Gly Gly Ile Cys Gly Pro Gly Ile Ile Ala
        1285                1290                1295

Gly Leu Ala Leu Ile Pro Leu Leu Leu Lys Arg Arg Asn
        1300                1305                1310

<210> SEQ ID NO 12
<211> LENGTH: 809
<212> TYPE: PRT
<213> ORGANISM: Artificial Sequence
<220> FEATURE:
<223> OTHER INFORMATION: Hybrid pullulanase of Thermoccus hydrothermalis
      and Thermococcus litoralis
<220> FEATURE:
<221> NAME/KEY: SIGNAL
<222> LOCATION: (1)..(27)
<220> FEATURE:
<221> NAME/KEY: mat_peptide
<222> LOCATION: (28)..(809)

<400> SEQUENCE: 12

Met Lys Lys Pro Leu Gly Lys Ile Val Ala Ser Thr Ala Leu Leu Ile
        -25                 -20                 -15

Ser Val Ala Phe Ser Ser Ser Ile Ala Ser Ala Glu Glu Pro Lys Pro
        -10                  -5                  -1   1              5

Leu Asn Val Ile Ile Val Trp His Gln His Gln Pro Tyr Tyr Tyr Asp
                10                  15                  20

Pro Ile Gln Asp Ile Tyr Thr Arg Pro Trp Val Arg Leu His Ala Ala
                25                  30                  35

Asn Asn Tyr Trp Lys Met Ala Asn Tyr Leu Ser Lys Tyr Pro Asp Val
                40                  45                  50

His Val Ala Ile Asp Leu Ser Gly Ser Leu Ile Ala Gln Leu Ala Asp
55                  60                  65

Tyr Met Asn Gly Lys Lys Asp Thr Tyr Gln Ile Val Thr Glu Lys Ile
70                  75                  80                  85

Ala Asn Gly Glu Pro Leu Thr Leu Glu Asp Lys Trp Phe Met Leu Gln
                90                  95                  100

Ala Pro Gly Gly Phe Phe Asp His Thr Ile Pro Trp Asn Gly Glu Pro
                105                 110                 115

Val Ala Asp Glu Asn Gly Asn Pro Tyr Arg Glu Gln Trp Asp Arg Tyr
                120                 125                 130

Ala Glu Leu Lys Asp Lys Arg Asn Asn Ala Phe Lys Lys Tyr Ala Asn
                135                 140                 145

Leu Pro Leu Asn Glu Gln Lys Val Lys Ile Thr Ala Glu Phe Thr Glu
150                 155                 160                 165

Gln Asp Tyr Ile Asp Leu Ala Val Leu Phe Asn Leu Ala Trp Ile Asp
                170                 175                 180

Tyr Asn Tyr Ile Ile Asn Thr Pro Glu Leu Lys Ala Leu Tyr Asp Lys
                185                 190                 195

Val Asp Val Gly Gly Tyr Thr Lys Glu Asp Val Ala Thr Val Leu Lys
                200                 205                 210
```

His Gln Met Trp Leu Leu Asn His Thr Phe Glu Glu His Glu Lys Ile
    215                 220                 225

Asn Tyr Leu Leu Gly Asn Gly Asn Val Glu Val Thr Val Val Pro Tyr
230                 235                 240                 245

Ala His Pro Ile Gly Pro Leu Leu Asn Asp Phe Gly Trp Tyr Glu Asp
                250                 255                 260

Phe Asp Ala His Val Lys Lys Ala His Glu Leu Tyr Lys Lys Tyr Leu
            265                 270                 275

Gly Asp Asn Arg Val Glu Pro Gln Gly Gly Trp Ala Ala Glu Ser Ala
        280                 285                 290

Leu Asn Asp Lys Thr Leu Glu Ile Leu Thr Asn Asn Gly Trp Lys Trp
    295                 300                 305

Val Met Thr Asp Gln Met Val Leu Asp Ile Leu Gly Ile Pro Asn Thr
310                 315                 320                 325

Val Glu Asn Tyr Tyr Lys Pro Trp Val Ala Glu Phe Asn Gly Lys Lys
                330                 335                 340

Ile Tyr Leu Phe Pro Arg Asn His Asp Leu Ser Asp Arg Val Gly Phe
            345                 350                 355

Arg Tyr Ser Gly Met Asn Gln Tyr Gln Ala Val Glu Asp Phe Val Asn
        360                 365                 370

Glu Leu Leu Lys Val Gln Lys Glu Asn Tyr Asp Gly Ser Leu Val Tyr
    375                 380                 385

Val Val Thr Leu Asp Gly Glu Asn Pro Trp Glu His Tyr Pro Phe Asp
390                 395                 400                 405

Gly Lys Ile Phe Leu Glu Glu Leu Tyr Lys Lys Leu Thr Glu Leu Gln
                410                 415                 420

Lys Gln Gly Leu Ile Arg Thr Val Thr Pro Ser Glu Tyr Ile Gln Met
            425                 430                 435

Tyr Gly Asp Lys Ala Asn Lys Leu Thr Pro Arg Met Met Glu Arg Leu
        440                 445                 450

Asp Leu Thr Gly Asp Asn Val Asn Ala Leu Leu Lys Ala Gln Ser Leu
    455                 460                 465

Gly Glu Leu Tyr Asp Met Thr Gly Val Lys Glu Glu Met Gln Trp Pro
470                 475                 480                 485

Glu Ser Ser Trp Ile Asp Gly Thr Leu Ser Thr Trp Ile Gly Glu Pro
                490                 495                 500

Gln Glu Asn Tyr Gly Trp Tyr Trp Leu Tyr Met Ala Arg Lys Ala Leu
            505                 510                 515

Met Glu Asn Lys Asp Lys Met Ser Gln Ala Asp Trp Glu Lys Ala Tyr
        520                 525                 530

Glu Tyr Leu Leu Arg Ala Glu Ala Ser Asp Trp Phe Trp Trp Tyr Gly
    535                 540                 545

Ser Asp Gln Asp Ser Gly Gln Asp Tyr Thr Phe Asp Arg Tyr Leu Lys
550                 555                 560                 565

Thr Tyr Leu Tyr Glu Met Tyr Lys Leu Ala Gly Val Glu Pro Pro Ser
                570                 575                 580

Tyr Leu Phe Gly Asn Tyr Phe Pro Asp Gly Glu Pro Tyr Thr Thr Arg
            585                 590                 595

Gly Leu Val Gly Leu Lys Asp Gly Glu Met Lys Asn Phe Ser Ser Met
        600                 605                 610

Ser Pro Leu Ala Lys Gly Val Ser Val Tyr Phe Asp Gly Glu Gly Ile
    615                 620                 625

His Phe Ile Val Lys Gly Asn Leu Asp Arg Phe Glu Val Ser Ile Trp

```
                630                 635                 640                 645
            Glu Lys Asp Glu Arg Val Gly Asn Thr Phe Thr Arg Leu Gln Glu Lys
                            650                 655                 660

Pro Asp Glu Leu Ser Tyr Phe Met Phe Pro Phe Ser Arg Asp Ser Val
                            665                 670                 675

Gly Leu Leu Ile Thr Lys His Val Val Tyr Glu Asn Gly Lys Ala Glu
                            680                 685                 690

Ile Tyr Gly Ala Thr Asp Tyr Glu Lys Ser Lys Leu Gly Glu Ala
                695                 700                 705

Thr Val Lys Asn Thr Ser Glu Gly Ile Glu Val Val Leu Pro Phe Asp
            710                 715                 720                 725

Tyr Ile Glu Asn Pro Ser Asp Phe Tyr Phe Ala Val Ser Thr Val Lys
                            730                 735                 740

Asp Gly Asp Leu Glu Val Ile Ser Thr Pro Val Glu Leu Lys Leu Pro
                            745                 750                 755

Thr Glu Val Lys Gly Val Val Ile Ala Asp Ile Thr Asp Pro Glu Gly
                            760                 765                 770

Asp Asp His Gly Pro Gly Asn Tyr Thr
            775                 780

<210> SEQ ID NO 13
<211> LENGTH: 412
<212> TYPE: PRT
<213> ORGANISM: Pyrococcus furiosus
<220> FEATURE:
<221> NAME/KEY: mat_peptide
<222> LOCATION: (1)..(412)
<223> OTHER INFORMATION: Pyrococcus furiosus protease (Pfu)

<400> SEQUENCE: 13

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
                20                  25                  30

Ile Asp Thr Gly Ile Asp Ala Ser His Pro Asp Leu Gln Gly Lys Val
            35                  40                  45

Ile Gly Trp Val Asp Phe Val Asn Gly Arg Ser Tyr Pro Tyr Asp Asp
        50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
    130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205
```

-continued

```
Arg Leu Lys Pro Glu Val Val Ala Pro Gly Asn Trp Ile Ile Ala Ala
        210                 215                 220
Arg Ala Ser Gly Thr Ser Met Gly Gln Pro Ile Asn Asp Tyr Tyr Thr
225                 230                 235                 240
Ala Ala Pro Gly Thr Ser Met Ala Thr Pro His Val Ala Gly Ile Ala
                245                 250                 255
Ala Leu Leu Leu Gln Ala His Pro Ser Trp Thr Pro Asp Lys Val Lys
                260                 265                 270
Thr Ala Leu Ile Glu Thr Ala Asp Ile Val Lys Pro Asp Glu Ile Ala
            275                 280                 285
Asp Ile Ala Tyr Gly Ala Gly Arg Val Asn Ala Tyr Lys Ala Ile Asn
        290                 295                 300
Tyr Asp Asn Tyr Ala Lys Leu Val Phe Thr Gly Tyr Val Ala Asn Lys
305                 310                 315                 320
Gly Ser Gln Thr His Gln Phe Val Ile Ser Gly Ala Ser Phe Val Thr
                325                 330                 335
Ala Thr Leu Tyr Trp Asp Asn Ala Asn Ser Asp Leu Asp Leu Tyr Leu
                340                 345                 350
Tyr Asp Pro Asn Gly Asn Gln Val Asp Tyr Ser Tyr Thr Ala Tyr Tyr
            355                 360                 365
Gly Phe Glu Lys Val Gly Tyr Tyr Asn Pro Thr Asp Gly Thr Trp Thr
        370                 375                 380
Ile Lys Val Val Ser Tyr Ser Gly Ser Ala Asn Tyr Gln Val Asp Val
385                 390                 395                 400
Val Ser Asp Gly Ser Leu Ser Gln Pro Gly Ser Ser
                405                 410

<210> SEQ ID NO 14
<211> LENGTH: 595
<212> TYPE: PRT
<213> ORGANISM: Penicillium oxalicum
<220> FEATURE:
<221> NAME/KEY: mat_peptide
<222> LOCATION: (1)..(595)
<223> OTHER INFORMATION: mature Penicillium oxalicum glucoamylase
      sequence

<400> SEQUENCE: 14

Arg Pro Asp Pro Lys Gly Gly Asn Leu Thr Pro Phe Ile His Lys Glu
1               5                   10                  15
Gly Glu Arg Ser Leu Gln Gly Ile Leu Asp Asn Leu Gly Gly Arg Gly
            20                  25                  30
Lys Lys Thr Pro Gly Thr Ala Ala Gly Leu Phe Ile Ala Ser Pro Asn
        35                  40                  45
Thr Glu Asn Pro Asn Tyr Tyr Tyr Thr Trp Thr Arg Asp Ser Ala Leu
    50                  55                  60
Thr Ala Lys Cys Leu Ile Asp Leu Phe Glu Asp Ser Arg Ala Lys Phe
65                  70                  75                  80
Pro Ile Asp Arg Lys Tyr Leu Glu Thr Gly Ile Arg Asp Tyr Lys Ser
                85                  90                  95
Ser Gln Ala Ile Leu Gln Ser Val Ser Asn Pro Ser Gly Thr Leu Lys
            100                 105                 110
Asp Gly Ser Gly Leu Gly Glu Pro Lys Phe Glu Ile Asp Leu Asn Pro
        115                 120                 125
Phe Ser Gly Ala Trp Gly Arg Pro Gln Arg Asp Gly Pro Ala Leu Arg
    130                 135                 140
```

```
Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
        195                 200                 205

Leu Val Glu Gly Ser Gln Leu Ala Lys Lys Leu Gly Lys Ser Cys Asp
    210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
    290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
            340                 345                 350

Leu Gly Lys Leu Glu Val Ser Glu Thr Ser Leu Ser Phe Phe Lys Asp
        355                 360                 365

Phe Asp Ala Thr Val Lys Ile Gly Ser Tyr Ser Arg Asn Ser Lys Thr
    370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415

Tyr Asp Arg Asn Thr Ala Ala Pro Leu Ser Ala Asn Asp Leu Thr Trp
            420                 425                 430

Ser Phe Ala Ser Phe Leu Thr Ala Thr Gln Arg Arg Asp Ala Val Val
        435                 440                 445

Pro Pro Ser Trp Gly Ala Lys Ser Ala Asn Lys Val Pro Thr Thr Cys
    450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                485                 490                 495

Phe Tyr Leu Ile Glu Asn Thr Tyr Tyr Gly Glu Asn Val Phe Met Ser
            500                 505                 510

Gly Asn Ile Thr Ala Leu Gly Asn Trp Asp Ala Lys Lys Gly Phe Pro
        515                 520                 525

Leu Thr Ala Asn Leu Tyr Thr Gln Asp Gln Asn Leu Trp Phe Ala Ser
    530                 535                 540

Val Glu Phe Ile Pro Ala Gly Thr Pro Phe Glu Tyr Lys Tyr Tyr Lys
545                 550                 555                 560
```

```
Val Glu Pro Asn Gly Asp Ile Thr Trp Glu Lys Gly Pro Asn Arg Val
            565                 570                 575

Phe Val Ala Pro Thr Gly Cys Pro Val Gln Pro His Ser Asn Asp Val
            580                 585                 590

Trp Gln Phe
        595

<210> SEQ ID NO 15
<211> LENGTH: 573
<212> TYPE: PRT
<213> ORGANISM: Gloeophyllum sepiarium

<400> SEQUENCE: 15

Met Tyr Arg Phe Leu Val Cys Ala Leu Gly Leu Ala Ala Ser Val Leu
1               5                   10                  15

Ala Gln Ser Val Asp Ser Tyr Val Ser Glu Gly Pro Ile Ala Lys
            20                  25                  30

Ala Gly Val Leu Ala Asn Ile Gly Pro Asn Gly Ser Lys Ala Ser Gly
            35                  40                  45

Ala Ser Ala Gly Val Val Ala Ser Pro Ser Thr Ser Asp Pro Asp
 50                  55                  60

Tyr Trp Tyr Thr Trp Thr Arg Asp Ser Ser Leu Val Phe Lys Ser Leu
 65                  70                  75                  80

Ile Asp Gln Tyr Thr Thr Gly Ile Asp Ser Thr Ser Ser Leu Arg Thr
                85                  90                  95

Leu Ile Asp Asp Phe Val Thr Ala Glu Ala Asn Leu Gln Gln Val Ser
            100                 105                 110

Asn Pro Ser Gly Thr Leu Thr Thr Gly Gly Leu Gly Glu Pro Lys Phe
            115                 120                 125

Asn Val Asp Glu Thr Ala Phe Thr Gly Ala Trp Gly Arg Pro Gln Arg
            130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
                165                 170                 175

Ile Ile Gln Asn Asp Leu Gly Tyr Val Val Ser Tyr Trp Asn Gln Ser
            180                 185                 190

Thr Tyr Asp Leu Trp Glu Glu Val Asp Ser Ser Phe Phe Thr Thr
            195                 200                 205

Ala Val Gln His Arg Ala Leu Arg Glu Gly Ala Ala Phe Ala Thr Ala
210                 215                 220

Ile Gly Gln Thr Ser Gln Val Ser Ser Tyr Thr Thr Gln Ala Asp Asn
225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Ala
            275                 280                 285

Thr Phe Gln Pro Cys Ser Asp Lys Ala Leu Ser Asn Leu Lys Val Tyr
            290                 295                 300

Val Asp Ser Phe Arg Ser Val Tyr Ser Ile Asn Ser Gly Val Ala Ser
305                 310                 315                 320

Asn Ala Ala Val Ala Thr Gly Arg Tyr Pro Glu Asp Ser Tyr Gln Gly
                325                 330                 335
```

```
Gly Asn Pro Trp Tyr Leu Thr Thr Phe Ala Val Ala Glu Gln Leu Tyr
            340                 345                 350

Asp Ala Leu Asn Val Trp Glu Ser Gln Gly Ser Leu Glu Val Thr Ser
            355                 360                 365

Thr Ser Leu Ala Phe Phe Gln Gln Phe Ser Ser Gly Val Thr Ala Gly
        370                 375                 380

Thr Tyr Ser Ser Ser Ser Ser Thr Tyr Ser Thr Leu Thr Ser Ala Ile
385                 390                 395                 400

Lys Asn Phe Ala Asp Gly Phe Val Ala Ile Asn Ala Lys Tyr Thr Pro
                405                 410                 415

Ser Asn Gly Gly Leu Ala Glu Gln Tyr Ser Lys Ser Asp Gly Ser Pro
            420                 425                 430

Leu Ser Ala Val Asp Leu Thr Trp Ser Tyr Ala Ser Ala Leu Thr Ala
        435                 440                 445

Phe Glu Ala Arg Asn Asn Thr Gln Phe Ala Gly Trp Gly Ala Ala Gly
    450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
            500                 505                 510

Ala Leu Leu Leu Ser Ser Ala Asn Tyr Pro Thr Trp Ser Ile Thr Val
        515                 520                 525

Asn Leu Pro Ala Ser Thr Ala Ile Glu Tyr Lys Tyr Ile Arg Lys Asn
    530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570

<210> SEQ ID NO 16
<211> LENGTH: 583
<212> TYPE: PRT
<213> ORGANISM: Rhizomucor pusillus

<400> SEQUENCE: 16

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
```

```
              130                 135                 140
Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
                180                 185                 190

His Ile Arg Lys Asp Phe Trp Thr Gly Tyr Ala Glu Ala Ala Gly Val
            195                 200                 205

Phe Ala Thr Gly Glu Val Phe Asn Gly Asp Pro Ala Tyr Val Gly Pro
        210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
                260                 265                 270

Thr Thr Phe Val Asp Asn His Asp Asn Pro Arg Phe Leu Asn Ser Gln
            275                 280                 285

Ser Asp Lys Ala Leu Phe Lys Asn Ala Leu Thr Tyr Val Leu Leu Gly
        290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
                340                 345                 350

Met Lys Ser Asn Lys Ala Val Tyr Met Asp Ile Tyr Val Gly Asp Asn
            355                 360                 365

Ala Tyr Ala Phe Lys His Gly Asp Ala Leu Val Val Leu Asn Asn Tyr
        370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
                420                 425                 430

Ala Ile Phe Thr Ser Ala Thr Gly Gly Thr Thr Thr Ala Thr Pro
            435                 440                 445

Thr Gly Ser Gly Ser Val Thr Ser Thr Ser Lys Thr Thr Ala Thr Ala
        450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
                500                 505                 510

Ser Asp Gly Ile Ala Leu Ser Ala Asp Lys Tyr Thr Ser Ser Asp Pro
            515                 520                 525

Leu Trp Tyr Val Thr Val Thr Leu Pro Ala Gly Glu Ser Phe Glu Tyr
        530                 535                 540

Lys Phe Ile Arg Ile Glu Ser Asp Asp Ser Val Glu Trp Glu Ser Asp
545                 550                 555                 560
```

```
Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 17
<211> LENGTH: 576
<212> TYPE: PRT
<213> ORGANISM: Gloephyllum trabeum
<220> FEATURE:
<221> NAME/KEY: SIGNAL
<222> LOCATION: (1)..(17)
<220> FEATURE:
<221> NAME/KEY: mat_peptide
<222> LOCATION: (18)..(576)

<400> SEQUENCE: 17

Met Tyr Arg Phe Leu Val Cys Ala Leu Gly Leu Gly Thr Val Leu
            -15                 -10                  -5

Ala Gln Ser Val Asp Ser Tyr Val Gly Ser Glu Gly Pro Ile Ala Lys
-1   1                   5                  10                  15

Ala Gly Val Leu Ala Asn Ile Gly Pro Asn Gly Ser Lys Ala Ser Gly
                 20                  25                  30

Ala Ala Ala Gly Val Val Ala Ser Pro Ser Lys Ser Asp Pro Asp
             35                  40                  45

Tyr Trp Tyr Thr Trp Thr Arg Asp Ser Ser Leu Val Phe Lys Ser Leu
             50                  55                  60

Ile Asp Gln Tyr Thr Thr Gly Ile Asp Ser Thr Ser Ser Leu Arg Ser
 65                  70                  75

Leu Ile Asp Ser Phe Val Ile Ala Glu Ala Asn Ile Gln Gln Val Ser
 80                  85                  90                  95

Asn Pro Ser Gly Thr Leu Thr Thr Gly Gly Leu Gly Glu Pro Lys Phe
                100                 105                 110

Asn Val Asp Glu Thr Ala Phe Thr Gly Ala Trp Gly Arg Pro Gln Arg
            115                 120                 125

Asp Gly Pro Ala Leu Arg Ala Thr Ala Leu Ile Thr Tyr Gly Asn Trp
        130                 135                 140

Leu Leu Ser Asn Gly Asn Thr Thr Trp Val Thr Ser Thr Leu Trp Pro
145                 150                 155

Ile Ile Gln Asn Asp Leu Asn Tyr Val Val Gln Tyr Trp Asn Gln Thr
160                 165                 170                 175

Thr Phe Asp Leu Trp Glu Glu Val Asn Ser Ser Phe Phe Thr Thr
            180                 185                 190

Ala Val Gln His Arg Ala Leu Arg Glu Gly Ala Ala Phe Ala Thr Lys
            195                 200                 205

Ile Gly Gln Thr Ser Ser Val Ser Ser Tyr Thr Thr Gln Ala Ala Asn
        210                 215                 220

Leu Leu Cys Phe Leu Gln Ser Tyr Trp Asn Pro Thr Ser Gly Tyr Ile
225                 230                 235

Thr Ala Asn Thr Gly Gly Gly Arg Ser Gly Lys Asp Ala Asn Thr Leu
240                 245                 250                 255

Leu Ala Ser Ile His Thr Tyr Asp Pro Ser Ala Gly Cys Asp Ala Thr
            260                 265                 270

Thr Phe Gln Pro Cys Ser Asp Lys Ala Leu Ser Asn Leu Lys Val Tyr
            275                 280                 285

Val Asp Ser Phe Arg Ser Val Tyr Ser Ile Asn Ser Gly Ile Ala Ser
```

```
            290                 295                 300
Asn Ala Ala Val Ala Thr Gly Arg Tyr Pro Glu Asp Ser Tyr Gln Gly
    305                 310                 315

Gly Asn Pro Trp Tyr Leu Thr Thr Phe Ala Val Ala Glu Gln Leu Tyr
320                 325                 330                 335

Asp Ala Leu Asn Val Trp Ala Ala Gln Gly Ser Leu Asn Val Thr Ser
                340                 345                 350

Ile Ser Leu Pro Phe Phe Gln Gln Phe Ser Ser Val Thr Ala Gly
            355                 360                 365

Thr Tyr Ala Ser Ser Ser Thr Thr Tyr Thr Thr Leu Thr Ser Ala Ile
        370                 375                 380

Lys Ser Phe Ala Asp Gly Phe Val Ala Ile Asn Ala Gln Tyr Thr Pro
            385                 390                 395

Ser Asn Gly Gly Leu Ala Glu Gln Phe Ser Arg Ser Asn Gly Ala Pro
400                 405                 410                 415

Val Ser Ala Val Asp Leu Thr Trp Ser Tyr Ala Ser Ala Leu Thr Ala
                420                 425                 430

Phe Glu Ala Arg Asn Asn Thr Gln Phe Ala Gly Trp Gly Ala Val Gly
            435                 440                 445

Leu Thr Val Pro Thr Ser Cys Ser Ser Asn Ser Gly Gly Gly Gly
            450                 455                 460

Ser Thr Val Ala Val Thr Phe Asn Val Asn Ala Gln Thr Val Trp Gly
465                 470                 475

Glu Asn Ile Tyr Ile Thr Gly Ser Val Asp Ala Leu Ser Asn Trp Ser
480                 485                 490                 495

Pro Asp Asn Ala Leu Leu Leu Ser Ser Ala Asn Tyr Pro Thr Trp Ser
                500                 505                 510

Ile Thr Val Asn Leu Pro Ala Ser Thr Ala Ile Gln Tyr Lys Tyr Ile
            515                 520                 525

Arg Lys Asn Asn Gly Ala Val Thr Trp Glu Ser Asp Pro Asn Asn Ser
            530                 535                 540

Ile Thr Thr Pro Ala Ser Gly Ser Val Thr Glu Asn Asp Thr Trp Arg
            545                 550                 555

<210> SEQ ID NO 18
<211> LENGTH: 573
<212> TYPE: PRT
<213> ORGANISM: Pycnoporus sanguineus

<400> SEQUENCE: 18

Met Arg Phe Thr Leu Leu Ala Ser Leu Ile Gly Leu Ala Val Gly Ala
1               5                   10                  15

Phe Ala Gln Ser Ser Ala Val Asp Ala Tyr Val Ala Ser Glu Ser Pro
            20                  25                  30

Ile Ala Lys Gln Gly Val Leu Asn Asn Ile Gly Pro Asn Gly Ser Lys
        35                  40                  45

Ala His Gly Ala Lys Ala Gly Ile Val Val Ala Ser Pro Ser Thr Glu
    50                  55                  60

Asn Pro Asp Tyr Leu Tyr Thr Trp Thr Arg Asp Ser Ser Leu Val Phe
65                  70                  75                  80

Lys Leu Leu Ile Asp Gln Phe Thr Ser Gly Asp Asp Thr Ser Leu Arg
                85                  90                  95

Gly Leu Ile Asp Asp Phe Thr Ser Ala Glu Ala Ile Leu Gln Gln Val
            100                 105                 110
```

```
Ser Asn Pro Ser Gly Thr Val Ser Thr Gly Gly Leu Gly Glu Pro Lys
            115                 120                 125

Phe Asn Ile Asp Glu Thr Ala Phe Thr Gly Ala Trp Gly Arg Pro Gln
        130                 135                 140

Arg Asp Gly Pro Ala Leu Arg Ala Thr Ser Ile Ile Arg Tyr Ala Asn
145                 150                 155                 160

Trp Leu Leu Asp Asn Gly Asn Thr Thr Tyr Val Ser Asn Thr Leu Trp
                165                 170                 175

Pro Val Ile Gln Leu Asp Leu Asp Tyr Val Ala Asp Asn Trp Asn Gln
            180                 185                 190

Ser Thr Phe Asp Leu Trp Glu Glu Val Asp Ser Ser Phe Phe Thr
        195                 200                 205

Thr Ala Val Gln His Arg Ala Leu Arg Glu Gly Ala Thr Phe Ala Ser
    210                 215                 220

Arg Ile Gly Gln Ser Ser Val Val Ser Gly Tyr Thr Thr Gln Ala Asp
225                 230                 235                 240

Asn Leu Leu Cys Phe Leu Gln Ser Tyr Trp Asn Pro Ser Gly Gly Tyr
                245                 250                 255

Val Thr Ala Asn Thr Gly Gly Gly Arg Ser Gly Lys Asp Ser Asn Thr
            260                 265                 270

Val Leu Thr Ser Ile His Thr Phe Asp Pro Ala Ala Gly Cys Asp Ala
        275                 280                 285

Ala Thr Phe Gln Pro Cys Ser Asp Lys Ala Leu Ser Asn Leu Lys Val
    290                 295                 300

Tyr Val Asp Ala Phe Arg Ser Ile Tyr Thr Ile Asn Asn Gly Ile Ala
305                 310                 315                 320

Ser Asn Ala Ala Val Ala Thr Gly Arg Tyr Pro Glu Asp Ser Tyr Met
                325                 330                 335

Gly Gly Asn Pro Trp Tyr Leu Thr Thr Ser Ala Val Ala Glu Gln Leu
            340                 345                 350

Tyr Asp Ala Leu Tyr Val Trp Asp Gln Leu Gly Gly Leu Asn Val Thr
        355                 360                 365

Ser Thr Ser Leu Ala Phe Phe Gln Gln Phe Ala Ser Gly Leu Ser Thr
    370                 375                 380

Gly Thr Tyr Ser Ala Ser Ser Thr Tyr Ala Thr Leu Thr Ser Ala
385                 390                 395                 400

Ile Arg Ser Phe Ala Asp Gly Phe Leu Ala Ile Asn Ala Lys Tyr Thr
                405                 410                 415

Pro Ala Asp Gly Gly Leu Ala Glu Gln Tyr Ser Arg Asn Asp Gly Thr
            420                 425                 430

Pro Leu Ser Ala Val Asp Leu Thr Trp Ser Tyr Ala Ala Ala Leu Thr
        435                 440                 445

Ala Phe Ala Ala Arg Glu Gly Lys Thr Tyr Gly Ser Trp Gly Ala Ala
    450                 455                 460

Gly Leu Thr Val Pro Ala Ser Cys Ser Gly Gly Gly Ala Thr Val
465                 470                 475                 480

Ala Val Thr Phe Asn Val Gln Ala Thr Val Phe Gly Glu Asn Ile
                485                 490                 495

Tyr Ile Thr Gly Ser Val Ala Ala Leu Gln Asn Trp Ser Pro Asp Asn
            500                 505                 510

Ala Leu Ile Leu Ser Ala Ala Asn Tyr Pro Thr Trp Ser Ile Thr Val
        515                 520                 525

Asn Leu Pro Ala Asn Thr Val Val Gln Tyr Lys Tyr Ile Arg Lys Phe
```

```
                530             535             540
Asn Gly Gln Val Thr Trp Glu Ser Asp Pro Asn Asn Gln Ile Thr Thr
545                 550                 555                 560

Pro Ser Gly Gly Ser Phe Thr Gln Asn Asp Val Trp Arg
                565                 570

<210> SEQ ID NO 19
<211> LENGTH: 618
<212> TYPE: PRT
<213> ORGANISM: Talaromyces emersonii

<400> SEQUENCE: 19

Met Ala Ser Leu Val Ala Gly Ala Leu Cys Ile Leu Gly Leu Thr Pro
1               5                   10                  15

Ala Ala Phe Ala Arg Ala Pro Val Ala Ala Arg Ala Thr Gly Ser Leu
                20                  25                  30

Asp Ser Phe Leu Ala Thr Glu Thr Pro Ile Ala Leu Gln Gly Val Leu
            35                  40                  45

Asn Asn Ile Gly Pro Asn Gly Ala Asp Val Ala Gly Ala Ser Ala Gly
        50                  55                  60

Ile Val Val Ala Ser Pro Ser Arg Ser Asp Pro Asn Tyr Phe Tyr Ser
65                  70                  75                  80

Trp Thr Arg Asp Ala Ala Leu Thr Ala Lys Tyr Leu Val Asp Ala Phe
                85                  90                  95

Ile Ala Gly Asn Lys Asp Leu Glu Gln Thr Ile Gln Gln Tyr Ile Ser
                100                 105                 110

Ala Gln Ala Lys Val Gln Thr Ile Ser Asn Pro Ser Gly Asp Leu Ser
            115                 120                 125

Thr Gly Gly Leu Gly Glu Pro Lys Phe Asn Val Asn Glu Thr Ala Phe
130                 135                 140

Thr Gly Pro Trp Gly Arg Pro Gln Arg Asp Gly Pro Ala Leu Arg Ala
145                 150                 155                 160

Thr Ala Leu Ile Ala Tyr Ala Asn Tyr Leu Ile Asp Asn Gly Glu Ala
                165                 170                 175

Ser Thr Ala Asp Glu Ile Ile Trp Pro Ile Val Gln Asn Asp Leu Ser
            180                 185                 190

Tyr Ile Thr Gln Tyr Trp Asn Ser Ser Thr Phe Asp Leu Trp Glu Glu
            195                 200                 205

Val Glu Gly Ser Ser Phe Phe Thr Thr Ala Val Gln His Arg Ala Leu
210                 215                 220

Val Glu Gly Asn Ala Leu Ala Thr Arg Leu Asn His Thr Cys Ser Asn
225                 230                 235                 240

Cys Val Ser Gln Ala Pro Gln Val Leu Cys Phe Leu Gln Ser Tyr Trp
                245                 250                 255

Thr Gly Ser Tyr Val Leu Ala Asn Phe Gly Gly Ser Gly Arg Ser Gly
                260                 265                 270

Lys Asp Val Asn Ser Ile Leu Gly Ser Ile His Thr Phe Asp Pro Ala
            275                 280                 285

Gly Gly Cys Asp Asp Ser Thr Phe Gln Pro Cys Ser Ala Arg Ala Leu
        290                 295                 300

Ala Asn His Lys Val Val Thr Asp Ser Phe Arg Ser Ile Tyr Ala Ile
305                 310                 315                 320

Asn Ser Gly Ile Ala Glu Gly Ser Ala Val Ala Val Gly Arg Tyr Pro
                325                 330                 335
```

Glu Asp Val Tyr Gln Gly Gly Asn Pro Trp Tyr Leu Ala Thr Ala Ala
            340                 345                 350

Ala Ala Glu Gln Leu Tyr Asp Ala Ile Tyr Gln Trp Lys Lys Ile Gly
                355                 360                 365

Ser Ile Ser Ile Thr Asp Val Ser Leu Pro Phe Phe Gln Asp Ile Tyr
            370                 375                 380

Pro Ser Ala Ala Val Gly Thr Tyr Asn Ser Gly Ser Thr Thr Phe Asn
385                 390                 395                 400

Asp Ile Ile Ser Ala Val Gln Thr Tyr Gly Asp Gly Tyr Leu Ser Ile
                405                 410                 415

Val Glu Lys Tyr Thr Pro Ser Asp Gly Ser Leu Thr Glu Gln Phe Ser
            420                 425                 430

Arg Thr Asp Gly Thr Pro Leu Ser Ala Ser Ala Leu Thr Trp Ser Tyr
            435                 440                 445

Ala Ser Leu Leu Thr Ala Ser Ala Arg Arg Gln Ser Val Val Pro Ala
            450                 455                 460

Ser Trp Gly Glu Ser Ser Ala Ser Ser Val Pro Ala Val Cys Ser Ala
465                 470                 475                 480

Thr Ser Ala Thr Gly Pro Tyr Ser Thr Ala Thr Asn Thr Val Trp Pro
                485                 490                 495

Ser Ser Gly Ser Gly Ser Ser Thr Thr Thr Ser Ser Ala Pro Cys Thr
            500                 505                 510

Thr Pro Thr Ser Val Ala Val Thr Phe Asp Glu Ile Val Ser Thr Ser
            515                 520                 525

Tyr Gly Glu Thr Ile Tyr Leu Ala Gly Ser Ile Pro Glu Leu Gly Asn
            530                 535                 540

Trp Ser Thr Ala Ser Ala Ile Pro Leu Arg Ala Asp Ala Tyr Thr Asn
545                 550                 555                 560

Ser Asn Pro Leu Trp Tyr Val Thr Val Asn Leu Pro Pro Gly Thr Ser
                565                 570                 575

Phe Glu Tyr Lys Phe Phe Lys Asn Gln Thr Asp Gly Thr Ile Val Trp
            580                 585                 590

Glu Asp Asp Pro Asn Arg Ser Tyr Thr Val Pro Ala Tyr Cys Gly Gln
            595                 600                 605

Thr Thr Ala Ile Leu Asp Asp Ser Trp Gln
            610                 615

<210> SEQ ID NO 20
<211> LENGTH: 574
<212> TYPE: PRT
<213> ORGANISM: Trametes cingulata

<400> SEQUENCE: 20

Met Arg Phe Thr Leu Leu Thr Ser Leu Leu Gly Leu Ala Leu Gly Ala
1               5                   10                  15

Phe Ala Gln Ser Ser Ala Ala Asp Ala Tyr Val Ala Ser Glu Ser Pro
                20                  25                  30

Ile Ala Lys Ala Gly Val Leu Ala Asn Ile Gly Pro Ser Gly Ser Lys
            35                  40                  45

Ser Asn Gly Ala Lys Ala Gly Ile Val Ile Ala Ser Pro Ser Thr Ser
        50                  55                  60

Asn Pro Asn Tyr Leu Tyr Thr Trp Thr Arg Asp Ser Ser Leu Val Phe
65                  70                  75                  80

Lys Ala Leu Ile Asp Gln Phe Thr Gly Glu Asp Thr Ser Leu Arg
                85                  90                  95

```
Thr Leu Ile Asp Glu Phe Thr Ser Ala Glu Ala Ile Leu Gln Gln Val
            100                 105                 110

Pro Asn Pro Ser Gly Thr Val Ser Thr Gly Gly Leu Gly Glu Pro Lys
            115                 120                 125

Phe Asn Ile Asp Glu Thr Ala Phe Thr Asp Ala Trp Gly Arg Pro Gln
            130                 135                 140

Arg Asp Gly Pro Ala Leu Arg Ala Thr Ala Ile Ile Thr Tyr Ala Asn
145                 150                 155                 160

Trp Leu Leu Asp Asn Lys Asn Thr Thr Tyr Val Thr Asn Thr Leu Trp
                165                 170                 175

Pro Ile Ile Lys Leu Asp Leu Asp Tyr Val Ala Ser Asn Trp Asn Gln
            180                 185                 190

Ser Thr Phe Asp Leu Trp Glu Glu Ile Asn Ser Ser Ser Phe Phe Thr
            195                 200                 205

Thr Ala Val Gln His Arg Ala Leu Arg Glu Gly Ala Thr Phe Ala Asn
            210                 215                 220

Arg Ile Gly Gln Thr Ser Val Val Ser Gly Tyr Thr Thr Gln Ala Asn
225                 230                 235                 240

Asn Leu Leu Cys Phe Leu Gln Ser Tyr Trp Asn Pro Thr Gly Gly Tyr
                245                 250                 255

Ile Thr Ala Asn Thr Gly Gly Gly Arg Ser Gly Lys Asp Ala Asn Thr
            260                 265                 270

Val Leu Thr Ser Ile His Thr Phe Asp Pro Ala Ala Gly Cys Asp Ala
            275                 280                 285

Val Thr Phe Gln Pro Cys Ser Asp Lys Ala Leu Ser Asn Leu Lys Val
            290                 295                 300

Tyr Val Asp Ala Phe Arg Ser Ile Tyr Ser Ile Asn Ser Gly Ile Ala
305                 310                 315                 320

Ser Asn Ala Ala Val Ala Thr Gly Arg Tyr Pro Glu Asp Ser Tyr Met
                325                 330                 335

Gly Gly Asn Pro Trp Tyr Leu Thr Thr Ser Ala Val Ala Glu Gln Leu
            340                 345                 350

Tyr Asp Ala Leu Ile Val Trp Asn Lys Leu Gly Ala Leu Asn Val Thr
            355                 360                 365

Ser Thr Ser Leu Pro Phe Phe Gln Gln Phe Ser Ser Gly Val Thr Val
            370                 375                 380

Gly Thr Tyr Ala Ser Ser Ser Thr Phe Lys Thr Leu Thr Ser Ala
385                 390                 395                 400

Ile Lys Thr Phe Ala Asp Gly Phe Leu Ala Val Asn Ala Lys Tyr Thr
            405                 410                 415

Pro Ser Asn Gly Gly Leu Ala Glu Gln Tyr Ser Arg Ser Asn Gly Ser
            420                 425                 430

Pro Val Ser Ala Val Asp Leu Thr Trp Ser Tyr Ala Ala Ala Leu Thr
            435                 440                 445

Ser Phe Ala Ala Arg Ser Gly Lys Thr Tyr Ala Ser Trp Gly Ala Ala
            450                 455                 460

Gly Leu Thr Val Pro Thr Thr Cys Ser Gly Ser Gly Gly Ala Gly Thr
465                 470                 475                 480

Val Ala Val Thr Phe Asn Val Gln Ala Thr Thr Val Phe Gly Glu Asn
                485                 490                 495

Ile Tyr Ile Thr Gly Ser Val Pro Ala Leu Gln Asn Trp Ser Pro Asp
            500                 505                 510
```

```
Asn Ala Leu Ile Leu Ser Ala Asn Tyr Pro Thr Trp Ser Ile Thr
            515                 520                 525
Val Asn Leu Pro Ala Ser Thr Thr Ile Glu Tyr Lys Tyr Ile Arg Lys
530                 535                 540
Phe Asn Gly Ala Val Thr Trp Glu Ser Asp Pro Asn Asn Ser Ile Thr
545                 550                 555                 560
Thr Pro Ala Ser Gly Thr Phe Thr Gln Asn Asp Thr Trp Arg
                565                 570
```

<210> SEQ ID NO 21
<211> LENGTH: 483
<212> TYPE: PRT
<213> ORGANISM: Bacillus licheniformis

<400> SEQUENCE: 21

```
Ala Asn Leu Asn Gly Thr Leu Met Gln Tyr Phe Glu Trp Tyr Met Pro
1               5                   10                  15
Asn Asp Gly Gln His Trp Arg Arg Leu Gln Asn Asp Ser Ala Tyr Leu
            20                  25                  30
Ala Glu His Gly Ile Thr Ala Val Trp Ile Pro Pro Ala Tyr Lys Gly
        35                  40                  45
Thr Ser Gln Ala Asp Val Gly Tyr Gly Ala Tyr Asp Leu Tyr Asp Leu
    50                  55                  60
Gly Glu Phe His Gln Lys Gly Thr Val Arg Thr Lys Tyr Gly Thr Lys
65                  70                  75                  80
Gly Glu Leu Gln Ser Ala Ile Lys Ser Leu His Ser Arg Asp Ile Asn
                85                  90                  95
Val Tyr Gly Asp Val Val Ile Asn His Lys Gly Gly Ala Asp Ala Thr
            100                 105                 110
Glu Asp Val Thr Ala Val Glu Val Asp Pro Ala Asp Arg Asn Arg Val
        115                 120                 125
Ile Ser Gly Glu His Leu Ile Lys Ala Trp Thr His Phe His Phe Pro
    130                 135                 140
Gly Arg Gly Ser Thr Tyr Ser Asp Phe Lys Trp His Trp Tyr His Phe
145                 150                 155                 160
Asp Gly Thr Asp Trp Asp Glu Ser Arg Lys Leu Asn Arg Ile Tyr Lys
                165                 170                 175
Phe Gln Gly Lys Ala Trp Asp Trp Glu Val Ser Asn Glu Asn Gly Asn
            180                 185                 190
Tyr Asp Tyr Leu Met Tyr Ala Asp Ile Asp Tyr Asp His Pro Asp Val
        195                 200                 205
Ala Ala Glu Ile Lys Arg Trp Gly Thr Trp Tyr Ala Asn Glu Leu Gln
    210                 215                 220
Leu Asp Gly Phe Arg Leu Asp Ala Val Lys His Ile Lys Phe Ser Phe
225                 230                 235                 240
Leu Arg Asp Trp Val Asn His Val Arg Glu Lys Thr Gly Lys Glu Met
                245                 250                 255
Phe Thr Val Ala Glu Tyr Trp Gln Asn Asp Leu Gly Ala Leu Glu Asn
            260                 265                 270
Tyr Leu Asn Lys Thr Asn Phe Asn His Ser Val Phe Asp Val Pro Leu
        275                 280                 285
His Tyr Gln Phe His Ala Ala Ser Thr Gln Gly Gly Gly Tyr Asp Met
    290                 295                 300
Arg Lys Leu Leu Asn Gly Thr Val Val Ser Lys His Pro Leu Lys Ser
305                 310                 315                 320
```

```
Val Thr Phe Val Asp Asn His Asp Thr Gln Pro Gly Gln Ser Leu Glu
            325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
            405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
        450                 455                 460

Glu Gly Trp Gly Glu Phe His Val Asn Gly Gly Ser Val Ser Ile Tyr
465                 470                 475                 480

Val Gln Arg
```